(12) United States Patent
Schweizer et al.

(10) Patent No.: US 7,834,243 B2
(45) Date of Patent: Nov. 16, 2010

(54) PROMOTER FOR EPIDERMIS-SPECIFIC, PATHOGEN-INDUCIBLE TRANSGENIC EXPRESSION IN PLANTS

(75) Inventors: Patrick Schweizer, Ballenstedt (DE); Axel Himmelbach, Thale (DE); Lothar Altschmied, Quedlinburg (DE); Helmut Maucher, Halle (DE)

(73) Assignee: Leibniz-Institut für Pflanzengenetik Und Kulturpflanzenforschung (IPK) (DE)

( * ) Notice: Subject to any disclaimer, the term of this patent is extended or adjusted under 35 U.S.C. 154(b) by 87 days.

(21) Appl. No.: 11/921,456

(22) PCT Filed: May 30, 2006

(86) PCT No.: PCT/EP2006/062747

§ 371 (c)(1),
(2), (4) Date: Apr. 3, 2008

(87) PCT Pub. No.: WO2006/128882

PCT Pub. Date: Dec. 7, 2006

(65) Prior Publication Data

US 2009/0100542 A1    Apr. 16, 2009

(30) Foreign Application Priority Data

Jun. 3, 2005    (DE) .................. 10 2005 025 656

(51) Int. Cl.
 *A01H 5/00*    (2006.01)
 *A01H 5/10*    (2006.01)
 *C12N 15/09*    (2006.01)
 *C12N 15/82*    (2006.01)

(52) U.S. Cl. .................. 800/287; 800/278; 800/279; 800/298; 800/295; 800/320; 800/317; 435/69.1; 435/320.1; 435/468; 536/24.1

(58) Field of Classification Search .................. None
See application file for complete search history.

(56) References Cited

FOREIGN PATENT DOCUMENTS

| EP | 0368137 A1 | 5/1990 |
|---|---|---|
| EP | 0368167 A1 | 5/1990 |
| WO | WO-02/057412 A2 | 7/2002 |
| WO | WO-2005/035766 A1 | 4/2005 |

OTHER PUBLICATIONS

Altpeter, F., et al., "Stable Expression of a Defense-Related Gene in Wheat Epidermis under Transcriptional Control of a Novel Promoter Confers Pathogen Resistance", Plant Molecular Biology, vol. 57, (2006), pp. 271 283.

Berna, A., et al., "Regulation by Biotic and Abiotic Stress of a Wheat Germin Gene Encoding Oxalate Oxidase, a $H_2O_2$-Producing Enzyme", Plant Molecular Biology, vol. 39., No. 3 (1999), pp. 539-549.

Canevascini, S., et al., "Tissue-Specific Expression and Promoter Analysis of the Tobacco *ltp1* Gene", Plant Physiol, Vol. 112, (1996), pp. 513-524.

Christensen, A. B., et al., "The Germinlike Protein GLP4 Exhibits Superoxide Dismutase Activity and is an Important Component of Quantitative Resistance in Wheat and Barley", Molecular Plant-Microbe Interactions, vol. 17, No. 1, (2004), pp. 109-117.

Druka, A., et al., "Physical and Genetic Mapping of Barley (*Hordeum vulgare*) germin-like cDNAs", PNAS, vol. 99, No. 2, (2002), pp. 850-855.

Gjetting, T., et al., "Differential Gene Expression in Individual Papilla-Resistant and Powdery Mildew-Infected Barley Epidermal Cells", Molecular Plant-Microbe Interactions, vol. 17, No. 7, (2004) pp. 729-738.

Wei, Y., et al., "An Epidermis/Papilla-Specific Oxalate Oxidase-Like Protein in the Defence Response of Barley Attacked by the Powdery Mildew Fungus", Plant Molecular Biology, vol. 36, (1998), pp. 101-112.

"H.vulgare mRNA for Oxalate Oxidase-Like Protein", EMBL Database, Accession No. X93171, Nov. 21, 1995.

"Hordeum vulgare germin-like 8 (CL8) gene, complete cds,", EMBL Database, Accession No. AF493980, Apr. 2, 2003.

"Hordeum vulgare germin-like 12 (GL12) gene, complete cds.", EMBL Database, Accession No. AF493981, Apr. 2, 2003.

"Hordeum vulgare partial glp2 gene for germin-like protein 2", EMBL Database, Accession No. AJ310534, Feb. 20, 2001.

*Primary Examiner*—Medina A Ibrahim
(74) *Attorney, Agent, or Firm*—Connolly Bove Lodge & Hutz LLP

(57) ABSTRACT

The invention relates to promoter regions, under the control of which transgenes can be expressed in plants in an epidermis-specific and pathogen-inducible manner. The invention also relates to recombinant nucleic acid molecules, including the promoters, to transgenic plants and plant cells, transformed with said the nucleic acid molecules and to methods for producing the same. The invention also relates to nucleic acid molecules, including a promoter according to the invention, nucleic acid sequences or transgenes, which can convey resistance to pathogens, plants and cell plants, transformed with the nucleic acid molecules and methods for producing the same. The invention also relates to the use of the promoter region according to the invention for analyzing pathogen-induced signal transduction pathways in plant cells.

38 Claims, 8 Drawing Sheets

SEQUENCE LISTING

```
<160> NUMBER OF SEQ ID NOS: 19

<210> SEQ ID NO 1
<211> LENGTH: 3334
<212> TYPE: DNA
<213> ORGANISM: Hordeum vulgare

<400> SEQUENCE: 1
cgtgcgtaaa ttaagggcat gattgagttc ctagatatgc atcctaattt ataaaataaa      60
aggagcatat gtaattgtgt gcctgtaatc agtgaatgta tttctacctt ttaaataatc     120
aaaaatattg tttttttatca cactgatatg atctcacatg cttttttttg gttctactgt    180
gtcgtatttc tcataattga tcaatatttt gggttctttt ccccttattc tgaaataata     240
tatgattagg ttaaaaaaa gaaacaatac aagattattt ggtaatgcag tatttgtttg      300
acgctggtgt tgaacacgta ttattatctg gcaatacatg tgaagtatgc gatgggtgga     360
gcccgattgt gctcaggatt taaatgtgaa tgtggaatgt gcaaaagttg cttcctggac     420
ttgttgttct ggtctctcgc tttctggtgc atgaaattag aaatatacag ttcctccatg     480 taatatttt agcttccttt tggttcaaag ctcttgtaag ttcgattgac ggctgctttg      540
atggaaatcg atgaggtggc tcattttatc taaattctta tgagtagtat ttttgatttt     600
cttaagttgg gaactaaaaa cacgtttttt tactaagttt tggaaactgg gcacaacgga     660
gtcgagattt taaacattag ctccaacata catataaaaa atatgcataa atgtagaaaa     720
taaacttatt accggaagtg cctaatgaca cacctcgagc atgctggcgg aagggagcag     780
atgagaagct ggaccacctt aagactcaac caggaccgat gacgacattc atccacgagc     840
cacctggaag aaaacacctg acttcgtcgt actgtcacct ttgaactaca gttgcatgtc     900
ggagacgacc cgctgcttaa accaagtagt gtcttgacca taccagcaga catgatgaaa     960
ggaggacatt gttgcatgta ctacaagata tgtgcatgca ataccgtgag tcatttgatt    1020
taaggcaggg tcgattggat cgccatacca ttccgaacac accaccgtaa atggagagtg    1080
```

```
ttgattgcac acattctgta gcaacttaaa agaatggaga gtgttagaac tagccgcttg    1140
ccgtagatca gatcgccgtc gtacgccaac acaactataa ccgaaactag aacaaaacct    1200
gcacgctacg agctaaaagc aagcaagctg gctggtggat cgattgttgg gctagctagc    1260
tatggaactg atgtattctg ccgtccggct agataaatct caatcggaac tacaccaaag    1320
tatagcacgc aaacacacga gataatctta caggagagga gatcaagcta agcagacgac    1380
tttgtctgtg tagaaaacga ttgctttaca taacttacat ctctcaactc ctctttgacc    1440
tcgtgtgcat cagttctcac catgaccaag tatacgtata tgatatctaa taaactatga    1500
tgatgggtgg cgacttttca tgaaaccagc gctccatgca ttgtgctgac ttggttgaga    1560
tggataaata attgtaatta ctactcagcc atacatcgga tgatgcatta gcgcttaagc    1620
atattaaaaa gcaaacttga aaagtttatg caaaatacta ttcagaagcc aatagatgat    1680
tatttagtaa tgtgctcaga ggtttcaacg tgcaagttga atgtgcaaac gttgcttcct    1740
tgagtcgttg ttgtggtctg cctttccggg gcatgtaata agtagtttac ggtagttcct    1800
ggagtatagc ccacatactt gggctatact tctctcagtg ataaaacttc tctctgtgta    1860
ccatcacgag tttactcata gatttcttcc gtaactaata gtgtcaagtt atacacttat    1920 atataccttga gttttctcta aaagaaaccg atatacctta cttgatgtcc ttctcttaat    1980
ctagaaaggt gttaattata atatttcca tcttgagtgt ttgtatcctc cgtatatgtt    2040
ttgattacag gctcaaagtt tcaattgaag gttttcttga tgttttttat cccaatacat    2100
ctgggactcc aacgggaata tttacaactt gcactgagat tcgttgtatt ctctgtctcc    2160
tagaaatttg aggacactgt ttattttgtg aagaaatgaa taagacggac gactctaggg    2220
cggtagttat gttttttatg gggcactgaa cctttcggcc tttctgttgt aattctgaat    2280
atgccttatt tttctcgcaa aaaataaaga atatgccttg ttttatgca gtcgtctagc    2340 tttgaatgtg ttccagtgtc ggttttggag cgagtaaata actttctgaa tgtaagcact    2400
tgaacttgag ctatcttgtc gtgttggctt gaaactgccc agccctggac gagttctcgt    2460
tcccggagaa gacgatggtg gtgctgggca gttaggaggg catcccggtg gacatcatcc    2520
aggaggcggt ggacgtgtgc gtcgagatcc cgcagctggg cgtcgtccgg tcgctcaacg    2580
tccgtgtcag cgccgccatc gccatctggg actacacccg ccagcagcgg gcccgctcct    2640
cctcctcgcg gtaggtagct tcccgctctt ccttgttgga gtgtaaatca gccatgcttg    2700
ttgttgtaag atgcatggac ctgaacatcc atggcaaaaa ctagtcatga accttagtca    2760
ggactagatt gttagattta tgaactgaat tggtcatgac gaaaattctt tggcaagaaa    2820
attttaactg ctcttgctct ccatcgtcca ttaattaatg tcgttgcttc ttccttcaag    2880
tactcaacca tttggagaga aatttgacca ggcaactgta tatctggttg acgtaatcat    2940
atgatacgta ttaggtgcgt taatgcatgg atcgacgcgc catgatttct tccttgtttg    3000
acacaatcaa aactattgct catagaaatt gttactaaga ggtctacatc acatggagta    3060
ccttaatttg cttctctatt tattaaaggg aaaaacgtgt atcaaagatt tgaatatggc    3120
tgaccacatc tcaaaagttt atgcagacta atctagtcgg cagccaaaga ccatttctat    3180
ccgttgggcg gttccacttg actatgtcca ttactcatga gttccacctg ctcgccatgc    3240
ctatataaaa acatcatcc ccagcatgtt ccaaccatca ctcacccaac aaacatctca    3300
ggaatatagg agaaaacaag acccaaagga gctg                               3334
```

<210> SEQ ID NO 2
<211> LENGTH: 114

<212> TYPE: DNA
<213> ORGANISM: Triticum sp.

<400> SEQUENCE: 2

```
gtcagtcgtc ggacggtgtc cgttcatttc ctccccatt ttgtaattga ttaacttgtt     60
atacatgctg acctcgacct gctgaataac gtccgtccat ggtttcccgt ccag         114
```

<210> SEQ ID NO 3
<211> LENGTH: 3497
<212> TYPE: DNA
<213> ORGANISM: Artificial Sequence
<220> FEATURE:
<223> OTHER INFORMATION: GLP4 Promotor + WIR1a Exon/Intron

<400> SEQUENCE: 3

```
cgtgcgtaaa ttaagggcat gattgagttc ctagatatgc atcctaattt ataaaataaa     60
aggagcatat gtaattgtgt gcctgtaatc agtgaatgta tttctacctt ttaaataatc    120
aaaaatattg tttttatca cactgatatg atctcacatg ctttttttg gttctactgt     180
gtcgtatttc tcataattga tcaatatttt gggttctttt ccccttattc tgaaataata    240
tatgattagg ttaaaaaaa gaaacaatac aagattattt ggtaatgcag tatttgtttg    300
acgctggtgt tgaacacgta ttattatctg gcaatacatg tgaagtatgc gatgggtgga    360
gcccgattgt gctcaggatt taaatgtgaa tgtggaatgt gcaaagttg cttcctggac    420
ttgttgttct ggtctctcgc tttctggtgc atgaaattag aaatatacag ttcctccatg    480
taatatttt agcttccttt tggttcaaag ctcttgtaag ttcgattgac ggctgctttg    540
atggaaatcg atgaggtggc tcatttatc taaattctta tgagtagtat ttttgatttt    600
cttaagttgg gaactaaaaa cacgttttt tactaagttt tggaaactgg gcacaacgga    660
gtcgagattt taaacattag ctccaacata catataaaaa atatgcataa atgtagaaaa    720
taaacttatt accggaagtg cctaatgaca cacctcgagc atgctggcgg aagggagcag    780
atgagaagct ggaccacctt aagactcaac caggaccgat gacgacattc atccacgagc    840
cacctggaag aaaacacctg acttcgtcgt actgtcacct ttgaactaca gttgcatgtc    900
ggagacgacc cgctgcttaa accaagtagt gtcttgacca taccagcaga catgatgaaa    960
ggaggacatt gttgcatgta ctacaagata tgtgcatgca ataccgtgag tcatttgatt   1020
taaggcaggg tcgattggat cgccatacca ttccgaacac accaccgtaa atggagagtg   1080
ttgattgcac acattctgta gcaacttaaa agaatggaga gtgttagaac tagccgcttg   1140
ccgtagatca gatcgccgtc gtacgccaac acaactataa ccgaaactag aacaaaacct   1200
gcacgctacg agctaaaagc aagcaagctg gctggtggat cgattgttgg gctagctagc   1260
tatggaactg atgtattctg ccgtccggct agataaatct caatcggaac tacaccaaag   1320
tatagcacgc aaacacacga gataatctta caggagagga gatcaagcta agcagacgac   1380
tttgtctgtg tagaaaacga ttgctttaca taacttacat ctctcaactc ctctttgacc   1440
tcgtgtgcat cagttctcac catgaccaag tatacgtata tgatatctaa taaactatga   1500
tgatgggtgg cgacttttca tgaaaccagc gctccatgca ttgtgctgac ttggttgaga   1560
tggataaata attgtaatta ctactcagcc atacatcgga tgatgcatta gcgcttaagc   1620
atattaaaaa gcaaacttga aaagtttatg caaaatacta ttcagaagcc aatagatgat   1680
tatttagtaa tgtgctcaga ggtttcaacg tgcaagttga atgtgcaaac gttgcttcct   1740
tgagtcgttg ttgtggtctg cctttccggg gcatgtaata agtagtttac ggtagttcct   1800
```

-continued

```
ggagtatagc ccacatactt gggctatact tctctcagtg ataaaacttc tctctgtgta   1860
ccatcacgag tttactcata gatttcttcc gtaactaata gtgtcaagtt atacacttat   1920 atataccttaa gttttctcta aaagaaaccg atatacctta cttgatgtcc ttctcttaat   1980
ctagaaaggt gttaattata aatatttcca tcttgagtgt ttgtatcctc cgtatatgtt   2040
ttgattacag gctcaaagtt tcaattgaag gttttcttga tgtttttat cccaatacat   2100 ctgggactcc aacgggaata tttacaactt gcactgagat tcgttgtatt ctctgtctcc   2160
tagaaatttg aggacactgt ttattttgtg aagaaatgaa taagacggac gactctaggg   2220
cggtagttat gtttttatg gggcactgaa cctttcggcc tttctgttgt aattctgaat   2280
atgccttatt tttctcgcaa aaataaaga atatgccttg tttttatgca gtcgtctagc   2340
tttgaatgtg ttccagtgtc ggttttggag cgagtaaata actttctgaa tgtaagcact   2400
tgaacttgag ctatcttgtc gtgttggctt gaaactgccc agccctggac gagttctcgt   2460
tcccggagaa gacgatggtg gtgctgggca gttaggaggg catcccggtg gacatcatcc   2520
aggaggcggt ggacgtgtgc gtcgagatcc cgcagctggg cgtcgtccgg tcgctcaacg   2580
tccgtgtcag cgccgccatc gccatctggg actacacccg ccagcagcgg gcccgctcct   2640
cctcctcgcg gtaggtagct tcccgctctt ccttgttgga gtgtaaatca gccatgcttg   2700
ttgttgtaag atgcatggac ctgaacatcc atggcaaaaa ctagtcatga accttagtca   2760
ggactagatt gttagattta tgaactgaat tggtcatgac gaaaattctt tggcaagaaa   2820
attttaactg ctcttgctct ccatcgtcca ttaattaatg tcgttgcttc ttccttcaag   2880
tactcaacca tttggagaga aatttgacca ggcaactgta tatctggttg acgtaatcat   2940
atgatacgta ttaggtgcgt taatgcatgg atcgacgcgc catgatttct tccttgtttg   3000
acacaatcaa aactattgct catagaaatt gttactaaga ggtctacatc acatggagta   3060
ccttaatttg cttctctatt tattaaaggg aaaaacgtgt atcaaagatt tgaatatggc   3120
tgaccacatc tcaaaagttt atgcagacta atctagtcgg cagccaaaga ccatttctat   3180
ccgttgggcg gttccacttg actatgtcca ttactcatga gttccacctg ctcgccatgc   3240
ctatataaaa acatacatcc ccagcatgtt ccaaccatca ctcacccaac aaacatctca   3300
ggaatatagg agaaaacaag acccaaagga gctgatcgaa ttcctgcagg gagccacggc   3360
cgtccacgac gccgccgcct caggtcagtc gtcggacggt gtccgttcat ttcctcccca   3420
tttttgtaat tgattaactt gttatacatg ctgacctcga cctgctgaat aacgtccgtc   3480
catggtttcc cgtccag                                                  3497
```

<210> SEQ ID NO 4
<211> LENGTH: 8841
<212> TYPE: DNA
<213> ORGANISM: Artificial Sequence
<220> FEATURE:
<223> OTHER INFORMATION: pGLP4GUS
<220> FEATURE:
<221> NAME/KEY: promoter
<222> LOCATION: (692)..(4025)
<223> OTHER INFORMATION: GLP4 promoter
<220> FEATURE:
<221> NAME/KEY: gene
<222> LOCATION: (4060)..(5871)
<223> OTHER INFORMATION: GUS
<220> FEATURE:
<221> NAME/KEY: terminator
<222> LOCATION: (5872)..(6612)
<223> OTHER INFORMATION: GstA1 terminator

<400> SEQUENCE: 4

```
ctaaattgta agcgttaata tttttgttaaa attcgcgtta aattttttgtt aaatcagctc    60
attttttaac caataggccg aaatcggcaa aatcccttat aaatcaaaag aatagaccga   120
gataggggttg agtgttgttc cagtttggaa caagagtcca ctattaaaga acgtggactc   180
caacgtcaaa gggcgaaaaa ccgtctatca gggcgatggc ccactacgtg aaccatcacc   240
ctaatcaagt tttttggggt cgaggtgccg taaagcacta atcggaacc  ctaaagggag   300
cccccgattt agagcttgac ggggaaagcc ggcgaacgtg gcgagaaagg aagggaagaa   360
agcgaaagga gcgggcgcta gggcgctggc aagtgtagcg gtcacgctgc gcgtaaccac   420
cacacccgcc gcgcttaatg cgccgctaca gggcgcgtcc cattcgccat tcaggctgcg   480
caactgttgg gaagggcgat cggtgcgggc ctcttcgcta ttacgccagc tggcgaaagg   540
gggatgtgct gcaaggcgat taagttgggt aacgccaggg ttttcccagt cacgacgttg   600
taaaacgacg ccagtgagc  gcgcgtaata cgactcacta tagggcgaat tgggtaccgg   660
gccccccctc gacggtatcg ataagcttga tcgtgcgtaa attaagggca tgattgagtt   720
cctagatatg catcctaatt tataaaataa aaggagcata tgtaattgtg tgcctgtaat   780
cagtgaatgt atttctacct tttaaataat caaaaatatt gttttttatc acactgatat   840
gatctcacat gcttttttt  ggttctactg tgtcgtattt ctcataattg atcaatattt   900
tgggttcttt tccccttatt ctgaaataat atatgattag gttaaaaaaa agaaacaata   960
caagattatt tggtaatgca gtatttgttt gacgctggtg ttgaacacgt attattatct  1020
ggcaatacat gtgaagtatg cgatgggtgg agcccgattg tgctcaggat ttaaatgtga  1080
atgtggaatg tgcaaaagtt gcttcctgga cttgttgttc tggtctctcg ctttctggtg  1140
catgaaatta gaaatataca gttcctccat gtaaattttt tagcttcctt ttggttcaaa  1200
gctcttgtaa gttcgattga cggctgcttt gatggaaatc gatgaggtgg ctcattttat  1260
ctaaattctt atgagtagta ttttgatt  tcttaagttg ggaactaaaa acacgttttt  1320
ttactaagtt ttggaaactg ggcacaacgg agtcgagatt ttaaacatta gctccaacat  1380
acatataaaa aatatgcata aatgtagaaa ataaacttat taccggaagt gcctaatgac  1440
acacctcgag catgctggcg gaagggagca gatgagaagc tggaccacct taagactcaa  1500
ccaggaccga tgacgacatt catccacgag ccacctggaa gaaaacacct gacttcgtcg  1560
tactgtcacc tttgaactac agttgcatgt cggagacgac ccgctgctta aaccaagtag  1620
tgtcttgacc ataccagcag acatgatgaa aggaggacat tgttgcatgt actcaaagat  1680
atgtgcatgc aataccgtga gtcatttgat ttaaggcagg gtcgattgga tcgccatacc  1740
attccgaaca caccaccgta aatggagagt gttgattgca cacattctgt agcaacttaa  1800
aagaatggag agtgttagaa ctagccgctt gccgtagatc agatcgccgt cgtacgccaa  1860
cacaactata accgaaacta gaacaaaacc tgcacgctac gagctaaaag caagcaagct  1920
ggctggtgga tcgattgttg ggctagctag ctatggaact gatgtattct gccgtccggc  1980
tagataaatc tcaatcggaa ctacaccaaa gtatagcacg caaacacacg agataatctt  2040
acaggagagg agatcaagct aagcagacga ctttgtctgt gtagaaaacg attgctttac  2100
ataacttaca tctctcaact cctctttgac ctcgtgtgca tcagttctca ccatgaccaa  2160
gtatacgtat atgatatcta ataaactatg atgatgggtg gcgactttc  atgaaaccag  2220
cgctccatgc attgtgctga cttggttgag atggataaat aattgtaatt actactcagc  2280
catacatcgg atgatgcatt agcgcttaag catattaaaa agcaaacttg aaaagtttat  2340
```

```
gcaaaatact attcagaagc aatagatga ttatttagta atgtgctcag aggtttcaac    2400
gtgcaagttg aatgtgcaaa cgttgcttcc ttgagtcgtt gttgtggtct gcctttccgg    2460
ggcatgtaat aagtagttta cggtagttcc tggagtatag cccacatact tgggctatac    2520
ttctctcagt gataaaactt ctctctgtgt accatcacga gtttactcat agatttcttc    2580
cgtaactaat agtgtcaagt tatacactta tatataccta agttttctct aaaagaaacc    2640
gatataccta acttgatgtc cttctcttaa tctagaaagg tgttaattat aaatatttcc    2700
atcttgagtg tttgtatcct ccgtatatgt tttgattaca ggctcaaagt ttcaattgaa    2760
ggttttcttg atgttttta tcccaataca tctgggactc caacgggaat atttacaact    2820
tgcactgaga ttcgttgtat tctctgtctc ctagaaattt gaggacactg tttattttgt    2880
gaagaaatga ataagacgga cgactctagg gcggtagtta tgtttttat ggggcactga    2940 acctttcggc ctttctgttg taattctgaa tatgccttat ttttctcgca aaaataaag    3000 aatatgcctt gttttatgc agtcgtctag ctttgaatgt gttccagtgt cggttttgga    3060
gcgagtaaat aactttctga atgtaagcac ttgaacttga gctatcttgt cgtgttggct    3120
tgaaactgcc cagccctgga cgagttctcg ttcccggaga agacgatggt ggtgctgggc    3180
agttaggagg gcatcccggt ggacatcatc caggaggcgg tggacgtgtg cgtcgagatc    3240
ccgcagctgg gcgtcgtccg gtcgctcaac gtccgtgtca cgccgccat cgccatctgg    3300 gactacaccc gccagcagcg ggcccgctcc tcctcctcgc ggtaggtagc ttcccgctct    3360
tccttgttgg agtgtaaatc agccatgctt gttgttgtaa gatgcatgga cctgaacatc    3420
catggcaaaa actagtcatg aaccttagtc aggactagat tgttagattt atgaactgaa    3480
ttggtcatga cgaaaattct ttggcaagaa aattttaact gctcttgctc tccatcgtcc    3540
attaattaat gtcgttgctt cttccttcaa gtactcaacc atttggagag aaatttgacc    3600
aggcaactgt atatctggtt gacgtaatca tatgatacgt attaggtgcg ttaatgcatg    3660
gatcgacgcg ccatgatttc ttccttgttt gacacaatca aaactattgc tcatagaaat    3720
tgttactaag aggtctacat cacatggagt accttaattt gcttctctat ttattaaagg    3780
gaaaaacgtg tatcaaagat ttgaatatgg ctgaccacat ctcaaaagtt tatgcagact    3840
aatctagtcg gcagccaaag accatttcta tccgttgggc ggttccactt gactatgtcc    3900
attactcatg agttccacct gctcgccatg cctatataaa aacatacatc cccagcatgt    3960
tccaaccatc actcacccaa caaacatctc aggaatatag gagaaaacaa gacccaaagg    4020
agctgatcga attcctgcag cccgggtggt cagtccctta tgttacgtcc tgtagaaacc    4080
ccaacccgtg aaatcaaaaa actcgacggc ctgtgggcat tcagtctgga tcgcgaaaac    4140
tgtggaattg atcagcgttg gtgggaaagc gcgttacaag aaagccgggc aattgctgtg    4200
ccaggcagtt ttaacgatca gttcgccgat gcagatattc gtaattatgc gggcaacgtc    4260
tggtatcagc gcgaagtctt tataccgaaa ggttgggcag ccagcgtat cgtgctgcgt    4320 ttcgatgcgg tcactcatta cggcaaagtg tgggtcaata atcaggaagt gatggagcat    4380
cagggcggct atacgccatt tgaagccgat gtcacgccgt atgttattgc cgggaaaagt    4440
gtacgtatca ccgtttgtgt gaacaacgaa ctgaactggc agactatccc gccgggaatg    4500
gtgattaccg acgaaaacgg caagaaaaag cagtcttact ccatgatttt ctttaactat    4560
gccggaatcc atcgcagcgt aatgctctac accacgccga acacctgggt ggacgatatc    4620
accgtggtga cgcatgtcgc gcaagactgt aaccacgcgt ctgttgactg gcaggtggtg    4680
gccaatggtg atgtcagcgt tgaactgcgt gatgcggatc aacaggtggt tgcaactgga    4740
```

```
caaggcacta gcgggacttt gcaagtggtg aatccgcacc tctggcaacc gggtgaaggt    4800
tatctctatg aactgtgcgt cacagccaaa agccagacag agtgtgatat ctacccgctt    4860
cgcgtcggca tccggtcagt ggcagtgaag ggcgaacagt tcctgattaa ccacaaaccg    4920
ttctacttta ctggctttgg tcgtcatgaa gatgcggact tgcgtggcaa aggattcgat    4980
aacgtgctga tggtgcacga ccacgcatta atggactgga ttggggccaa ctcctaccgt    5040
acctcgcatt acccttacgc tgaagagatg ctcgactggg cagatgaaca tggcatcgtg    5100
gtgattgatg aaactgctgc tgtcggcttt aacctctctt taggcattgg tttcgaagcg    5160
ggcaacaagc cgaaagaact gtacagcgaa gaggcagtca acggggaaac tcagcaagcg    5220
cacttacagg cgattaaaga gctgatagcg cgtgacaaaa accacccaag cgtggtgatg    5280
tggagtattg ccaacgaacc ggatacccgt ccgcaaggtg cacgggaata tttcgcgcca    5340
ctggcggaag caacgcgtaa actcgacccg acgcgtccga tcacctgcgt caatgtaatg    5400
ttctgcgacg ctcacaccga taccatcagc gatctctttg atgtgctgtg cctgaaccgt    5460
tattacggat ggtatgtcca aagcggcgat ttggaaacgg cagagaaggt actgaaaaaa    5520
gaacttctgg cctggcagga gaaactgcat cagccgatta tcatcaccga atacggcgtg    5580
gatacgttag ccgggctgca ctcaatgtac accgacatgt ggagtgaaga gtatcagtgt    5640
gcatggctgg atatgtatca ccgcgtcttt gatcgcgtca gcgccgtcgt cggtgaacag    5700
gtatggaatt tcgccgattt tgcgacctcg caaggcatat tgcgcgttgg cggtaacaag    5760
aaagggatct tcactcgcga ccgcaaaccg aagtcggcgg cttttctgct gcaaaaacgc    5820
tggactggca tgaacttcgg tgaaaaaccg cagcagggag gcaaacaatg agagctacta    5880
gtatgcctac cgagtttaag ctaggtgcgc agtactaggg gtttatgcac tccgcgcggg    5940
tgtgtgccgt gccgtgccgt gccgtgccgg tgatgattcc gttcaagaaa agagacctcc    6000
ctcccgtggg tgggtgatca tctgcccgtc tacttccagt agtatacgct tcagtttca    6060 gcagcacgag gagtccgctt gcgcttctgt tcgtgcgctg gattccttgc tttaatttat    6120
gcactagtac tagttagtaa ataaacaacg gactggtcaa tgctgctaat ccgtactgta    6180
cgtcctatat agtagtaccc cactagagat cagtatatat atacatcttg gatacgtgtg    6240
catttgcatg caaatatata tggacaggga taactggcac atgtgtgccc gttaggaaaa    6300
ttacgatcgc tctccttcgg tcggtggccc gctcgctcga tcgagcgttc cttcggtcgg    6360
tgtcccgctc gcccttcggt ccgtggcccg ctcgctcgat cgagcgttcc ttcggtcggt    6420
gtcccgctcg ctcgatcgag cgttgaggcc agttggctcg atcgctccgc tttgatcgag    6480
ttgtgaatgc tttcaccggt tttttttttct tctgattttt attttcagaa cggtctacta    6540
aatagtcact acacccaata accaactcgg ccatcctacc ttgttatcca caatacgtga    6600
acaacggaag ttgaattcta gtctacgcgg ccgcgagctc cagcttttgt tccctttagt    6660
gagggttaat tgcgcgcttg gcgtaatcat ggtcatagct gtttcctgtg tgaaattgtt    6720
atccgctcac aattccacac aacatacgag ccggaagcat aaagtgtaaa gcctggggtg    6780
cctaatgagt gagctaactc acattaattg cgttgcgctc actgcccgct ttccagtcgg    6840
gaaacctgtc gtgccagctg cattaatgaa tcggccaacg cgcggggaga ggcggtttgc    6900
gtattgggcg ctcttccgct tcctcgctca ctgactcgct gcgctcggtc gttcggctgc    6960
ggcgagcggt atcagctcac tcaaaggcgg taatacggtt atccacagaa tcaggggata    7020
acgcaggaaa gaacatgtga gcaaaaggcc agcaaaaggc caggaaccgt aaaaaggccg    7080
```

-continued

```
cgttgctggc gttttttccat aggctccgcc ccctgacga gcatcacaaa aatcgacgct    7140
caagtcagag gtggcgaaac ccgacaggac tataaagata ccaggcgttt ccccctggaa    7200
gctccctcgt gcgctctcct gttccgaccc tgccgcttac cggatacctg tccgcctttc    7260
tcccttcggg aagcgtggcg ctttctcata gctcacgctg taggtatctc agttcggtgt    7320
aggtcgttcg ctccaagctg gctgtgtgc acgaaccccc cgttcagccc gaccgctgcg    7380
ccttatccgg taactatcgt cttgagtcca acccggtaag acacgactta tcgccactgg    7440
cagcagccac tggtaacagg attagcagag cgaggtatgt aggcggtgct acagagttct    7500
tgaagtggtg gcctaactac ggctacacta gaaggacagt atttggtatc tgcgctctgc    7560
tgaagccagt taccttcgga aaaagagttg gtagctcttg atccggcaaa caaaccaccg    7620
ctggtagcgg tggttttttt gtttgcaagc agcagattac gcgcagaaaa aaggatctc    7680
aagaagatcc tttgatcttt tctacggggt ctgacgctca gtggaacgaa aactcacgtt    7740
aagggatttt ggtcatgaga ttatcaaaaa ggatcttcac ctagatcctt ttaaattaaa    7800
aatgaagttt taaatcaatc taaagtatat atgagtaaac ttggtctgac agttaccaat    7860
gcttaatcag tgaggcacct atctcagcga tctgtctatt tcgttcatcc atagttgcct    7920
gactccccgt cgtgtagata actacgatac gggagggctt accatctggc cccagtgctg    7980
caatgatacc gcgagaccca cgctcaccgg ctccagattt atcagcaata aaccagccag    8040
ccggaagggc cgagcgcaga agtggtcctg caactttatc cgcctccatc cagtctatta    8100
attgttgccg ggaagctaga gtaagtagtt cgccagttaa tagtttgcgc aacgttgttg    8160
ccattgctac aggcatcgtg gtgtcacgct cgtcgtttgg tatggcttca ttcagctccg    8220
gttcccaacg atcaaggcga gttacatgat cccccatgtt gtgcaaaaaa gcggttagct    8280
ccttcggtcc tccgatcgtt gtcagaagta agttggccgc agtgttatca ctcatggtta    8340
tggcagcact gcataattct cttactgtca tgccatccgt aagatgcttt tctgtgactg    8400
gtgagtactc aaccaagtca ttctgagaat agtgtatgcg gcgaccgagt tgctcttgcc    8460
cggcgtcaat acgggataat accgcgccac atagcagaac tttaaaagtg ctcatcattg    8520
gaaaacgttc ttcggggcga aaactctcaa ggatcttacc gctgttgaga tccagttcga    8580
tgtaacccac tcgtgcaccc aactgatctt cagcatcttt tactttcacc agcgtttctg    8640
ggtgagcaaa aacaggaagg caaaatgccg caaaaaaggg aataagggcg acacggaaat    8700
gttgaatact catactcttc ctttttcaat attattgaag catttatcag ggttattgtc    8760
tcatgagcgg atacatattt gaatgtattt agaaaaataa acaaataggg gttccgcgca    8820
catttccccg aaaagtgcca c                                              8841
```

<210> SEQ ID NO 5
<211> LENGTH: 8993
<212> TYPE: DNA
<213> ORGANISM: Artificial Sequence
<220> FEATURE:
<223> OTHER INFORMATION: pGLP4IntronGUS
<220> FEATURE:
<221> NAME/KEY: promoter
<222> LOCATION: (692)..(4025)
<223> OTHER INFORMATION: GLP4 promoter
<220> FEATURE:
<221> NAME/KEY: misc_feature
<222> LOCATION: (4040)..(4193)
<223> OTHER INFORMATION: WIR1 part of 5'CDS + intron
<220> FEATURE:
<221> NAME/KEY: gene
<222> LOCATION: (4212)..(6023)
<223> OTHER INFORMATION: GUS

```
<220> FEATURE:
<221> NAME/KEY: terminator
<222> LOCATION: (6024)..(6764)
<223> OTHER INFORMATION: GstA1 terminator

<400> SEQUENCE: 5
```

| | | | | | |
|---|---|---|---|---|---|
| ctaaattgta | agcgttaata | ttttgttaaa | attcgcgtta | aattttttgtt | aaatcagctc | 60 |
| atttttttaac | caataggccg | aaatcggcaa | aatcccttat | aaatcaaaag | aatagaccga | 120 |
| gatagggttg | agtgttgttc | cagtttggaa | caagagtcca | ctattaaaga | acgtggactc | 180 |
| caacgtcaaa | gggcgaaaaa | ccgtctatca | gggcgatggc | ccactacgtg | aaccatcacc | 240 |
| ctaatcaagt | tttttggggt | cgaggtgccg | taaagcacta | aatcggaacc | ctaaagggag | 300 |
| cccccgattt | agagcttgac | ggggaaagcc | ggcgaacgtg | gcgagaaagg | aagggaagaa | 360 |
| agcgaaagga | gcgggcgcta | gggcgctggc | aagtgtagcg | gtcacgctgc | gcgtaaccac | 420 |
| cacacccgcc | gcgcttaatg | cgccgctaca | gggcgcgtcc | cattcgccat | tcaggctgcg | 480 |
| caactgttgg | gaagggcgat | cggtgcgggc | ctcttcgcta | ttacgccagc | tggcgaaagg | 540 |
| gggatgtgct | gcaaggcgat | taagttgggt | aacgccaggg | ttttcccagt | cacgacgttg | 600 |
| taaaacgacg | gccagtgagc | gcgcgtaata | cgactcacta | tagggcgaat | tgggtaccgg | 660 |
| gccccccctc | gacggtatcg | ataagcttga | tcgtgcgtaa | attaagggca | tgattgagtt | 720 |
| cctagatatg | catcctaatt | tataaaataa | aaggagcata | tgtaattgtg | tgcctgtaat | 780 |
| cagtgaatgt | atttctacct | tttaaataat | caaaaatatt | gttttttatc | acactgatat | 840 |
| gatctcacat | gcttttttttt | ggttctactg | tgtcgtattt | ctcataattg | atcaatattt | 900 |
| tgggttctttt | tccccttatt | ctgaaataat | atatgattag | gttaaaaaaa | agaaacaata | 960 |
| caagattatt | tggtaatgca | gtatttgttt | gacgctggtg | ttgaacacgt | attattatct | 1020 |
| ggcaatacat | gtgaagtatg | cgatgggtgg | agcccgattg | tgctcaggat | ttaaatgtga | 1080 |
| atgtggaatg | tgcaaaagtt | gcttcctgga | cttgttgttc | tggtctctcg | ctttctggtg | 1140 |
| catgaaatta | gaaatataca | gttcctccat | gtaatatttt | tagcttcctt | ttggttcaaa | 1200 |
| gctcttgtaa | gttcgattga | cggctgcttt | gatggaaatc | gatgaggtgg | ctcattttat | 1260 |
| ctaaattctt | atgagtagta | ttttgattt | tcttaagttg | ggaactaaaa | acacgttttt | 1320 |
| ttactaagtt | ttggaaactg | ggcacaacgg | agtcagatt | ttaaacatta | gctccaacat | 1380 |
| acatataaaa | aatatgcata | aatgtagaaa | ataaacttat | taccggaagt | gcctaatgac | 1440 |
| acacctcgag | catgctggcg | aagggagca | gatgagaagc | tggaccacct | taagactcaa | 1500 |
| ccaggaccga | tgacgacatt | catccacgag | ccacctggaa | gaaaacacct | gacttcgtcg | 1560 |
| tactgtcacc | tttgaactac | agttgcatgt | cggagacgac | ccgctgctta | aaccaagtag | 1620 |
| tgtcttgacc | ataccagcag | acatgatgaa | aggaggacat | tgttgcatgt | actacaagat | 1680 |
| atgtgcatgc | aataccgtga | gtcatttgat | ttaaggcagg | gtcgattgga | tcgccatacc | 1740 |
| attccgaaca | caccaccgta | aatggagagt | gttgattgca | cacattctgt | agcaacttaa | 1800 |
| aagaatggag | agtgttagaa | ctagccgctt | gccgtagatc | agatcgccgt | cgtacgccaa | 1860 |
| cacaactata | accgaaacta | gaacaaaacc | tgcacgctac | gagctaaaag | caagcaagct | 1920 |
| ggctggtgga | tcgattgttg | ggctagctag | ctatggaact | gatgtattct | gccgtccggc | 1980 |
| tagataaatc | tcaatcggaa | ctacaccaaa | gtatagcacg | caaacacacg | agataatctt | 2040 |
| acaggagagg | agatcaagct | aagcagacga | ctttgtctgt | gtagaaaacg | attgctttac | 2100 |
| ataacttaca | tctctcaact | cctctttgac | ctcgtgtgca | tcagttctca | ccatgaccaa | 2160 |

```
gtatacgtat atgatatcta ataaactatg atgatgggtg gcgacttttc atgaaaccag    2220
cgctccatgc attgtgctga cttggttgag atggataaat aattgtaatt actactcagc    2280
catacatcgg atgatgcatt agcgcttaag catattaaaa agcaaacttg aaaagtttat    2340
gcaaaatact attcagaagc caatagatga ttatttagta atgtgctcag aggtttcaac    2400
gtgcaagttg aatgtgcaaa cgttgcttcc ttgagtcgtt gttgtggtct gcctttccgg    2460
ggcatgtaat aagtagttta cggtagttcc tggagtatag cccacatact tgggctatac    2520
ttctctcagt gataaaactt ctctctgtgt accatcacga gtttactcat agatttcttc    2580
cgtaactaat agtgtcaagt tatacactta tatatacctt agttttctct aaaagaaacc    2640 gatataccttt acttgatgtc cttctcttaa tctagaaagg tgttaattat aaatatttcc    2700
atcttgagtg tttgtatcct ccgtatatgt tttgattaca ggctcaaagt ttcaattgaa    2760
ggttttcttg atgtttttta tcccaataca tctgggactc caacgggaat atttacaact    2820
tgcactgaga ttcgttgtat tctctgtctc ctagaaattt gaggacactg tttattttgt    2880
gaagaaatga ataagacgga cgactctagg gcggtagtta tgttttttat ggggcactga    2940
acctttcggc ctttctgttg taattctgaa tatgccttat ttttctcgca aaaataaag    3000 aatatgcctt gttttatgc agtcgtctag ctttgaatgt gttccagtgt cggttttgga    3060
gcgagtaaat aactttctga atgtaagcac ttgaacttga gctatcttgt cgtgttggct    3120
tgaaactgcc cagccctgga cgagttctcg ttcccggaga agacgatggt ggtgctgggc    3180
agttaggagg gcatcccggt ggacatcatc caggaggcgg tggacgtgtg cgtcgagatc    3240
ccgcagctgg gcgtcgtccg gtcgctcaac gtccgtgtca gcgccgccat cgccatctgg    3300
gactacaccc gccagcagcg ggcccgctcc tcctcctcgc ggtaggtagc ttcccgctct    3360
tccttgttgg agtgtaaatc agccatgctt gttgttgtaa gatgcatgga cctgaacatc    3420
catggcaaaa actagtcatg aaccttagtc aggactagat tgttagattt atgaactgaa    3480
ttggtcatga cgaaaattct ttggcaagaa aattttaact gctcttgctc tccatcgtcc    3540
attaattaat gtcgttgctt cttccttcaa gtactcaacc atttggagag aaatttgacc    3600
aggcaactgt atatctggtt gacgtaatca tatgatacgt attaggtgcg ttaatgcatg    3660
gatcgacgcg ccatgatttc ttccttgttt gacacaatca aaactattgc tcatagaaat    3720
tgttactaag aggtctacat cacatggagt accttaattt gcttctctat ttattaaagg    3780
gaaaaacgtg tatcaaagat ttgaatatgg ctgaccacat ctcaaaagtt tatgcagact    3840
aatctagtcg gcagccaaag accatttcta tccgttgggc ggttccactt gactatgtcc    3900
attactcatg agttccacct gctcgccatg cctatataaa acatacatc cccagcatgt    3960 tccaaccatc actcacccaa caaacatctc aggaatatag gagaaaacaa gacccaaagg    4020
agctgatcga attcctgcag ggagccacgg ccgtccacga cgccgccgcc tcaggtcagt    4080
cgtcggacgg tgtccgttca tttcctcccc atttttgtaa ttgattaact tgttatacat    4140
gctgacctcg acctgctgaa taacgtccgt ccatggtttc ccgtccaggc accccgggtg    4200
gtcagtccct tatgttacgt cctgtagaaa ccccaacccg tgaaatcaaa aaactcgacg    4260
gcctgtgggc attcagtctg gatcgcgaaa actgtggaat tgatcagcgt tggtgggaaa    4320
gcgcgttaca agaaagccgg gcaattgctg tgccaggcag ttttaacgat cagttcgccg    4380
atgcagatat tcgtaattat gcgggcaacg tctggtatca gcgcgaagtc tttataccga    4440
aaggttgggc aggccagcgt atcgtgctgc gtttcgatgc ggtcactcat tacggcaaag    4500
tgtgggtcaa taatcaggaa gtgatggagc atcagggcgg ctatacgcca tttgaagccg    4560
```

```
atgtcacgcc gtatgttatt gccgggaaaa gtgtacgtat caccgtttgt gtgaacaacg    4620
aactgaactg gcagactatc ccgccgggaa tggtgattac cgacgaaaac ggcaagaaaa    4680
agcagtctta cttccatgat ttctttaact atgccggaat ccatcgcagc gtaatgctct    4740
acaccacgcc gaacacctgg gtggacgata tcaccgtggt gacgcatgtc gcgcaagact    4800
gtaaccacgc gtctgttgac tggcaggtgg tggccaatgg tgatgtcagc gttgaactgc    4860
gtgatgcgga tcaacaggtg gttgcaactg gacaaggcac tagcgggact ttgcaagtgg    4920
tgaatccgca cctctggcaa ccgggtgaag gttatctcta tgaactgtgc gtcacagcca    4980
aaagccagac agagtgtgat atctacccgc ttcgcgtcgg catccggtca gtggcagtga    5040
agggcgaaca gttcctgatt aaccacaaac cgttctactt tactggcttt ggtcgtcatg    5100
aagatgcgga cttgcgtggc aaaggattcg ataacgtgct gatggtgcac gaccacgcat    5160
taatggactg gattgggggcc aactcctacc gtacctcgca ttacccttac gctgaagaga    5220
tgctcgactg ggcagatgaa catggcatcg tggtgattga tgaaactgct gctgtcggct    5280
ttaacctctc tttaggcatt ggtttcgaag cgggcaacaa gccgaaagaa ctgtacagcg    5340
aagaggcagt caacggggaa actcagcaag cgcacttaca ggcgattaaa gagctgatag    5400
cgcgtgacaa aaaccaccca agcgtggtga tgtggagtat tgccaacgaa ccggataccc    5460
gtccgcaagg tgcacgggaa tatttcgcgc cactggcgga agcaacgcgt aaactcgacc    5520
cgacgcgtcc gatcacctgc gtcaatgtaa tgttctgcga cgctcacacc gataccatca    5580
gcgatctctt tgatgtgctg tgcctgaacc gttattacgg atggtatgtc caaagcggcg    5640
atttggaaac ggcagagaag gtactggaaa agaacttct ggcctggcag gagaaactgc    5700
atcagccgat tatcatcacc gaatacgcg tggatacgtt agccgggctg cactcaatgt    5760
acaccgacat gtggagtgaa gagtatcagt gtgcatggct ggatatgtat caccgcgtct    5820
ttgatcgcgt cagcgccgtc gtcggtgaac aggtatggaa tttcgccgat tttgcgacct    5880
cgcaaggcat attgcgcgtt ggcggtaaca agaaagggat cttcactcgc gaccgcaaac    5940
cgaagtcggc ggcttttctg ctgcaaaaac gctggactgg catgaacttc ggtgaaaaac    6000
cgcagcaggg aggcaaacaa tgagagctac tagtatgcct accgagttta gctaggtgc    6060 gcagtactag gtgtttatgc actccgcgcg ggtgtgtgcc gtgccgtgcc gtgccgtgcc    6120
ggtgatgatt ccgttcaaga aaagagacct ccctcccgtg ggtgggtgat catctgcccg    6180
tctacttcca gtagtatacg ctttcagttt cagcagcacg aggagtccgc ttgcgcttct    6240
gttcgtgcgc tggattcctt gctttaattt atgcactagt actagttagt aaataaacaa    6300
cggactggtc aatgctgcta atccgtactg tacgtcctat atagtagtac cccactagag    6360
atcagtatat atatacatct tggatacgtg tgcatttgca tgcaaatata tatggacagg    6420
gataactggc acatgtgtgc ccgttaggaa aattacgatc gctctccttc ggtcggtggc    6480
ccgctcgctc gatcgagcgt tccttcggtc ggtgtcccgc tcgcccttcg gtccgtggcc    6540
cgctcgctcg atcgagcgtt ccttcggtcg gtgtcccgct cgctcgatcg agcgttgagg    6600
ccagttggct cgatcgctcc gctttgatcg agttgtgaat gctttcaccg gtttttttt    6660 cttctgattt ttattttcag aacggtctac taaatagtca ctacacccaa taaccaactc    6720
ggccatccta ccttgttatc cacaaatacgt gaacaacgga agttgaattc tagtctacgc    6780
ggccgcgagc tccagctttt gttccctta gtgagggtta attgcgcgct tggcgtaatc    6840
atggtcatag ctgtttcctg tgtgaaattg ttatccgctc acaattccac acaacatacg    6900
```

```
agccggaagc ataaagtgta aagcctgggg tgcctaatga gtgagctaac tcacattaat    6960
tgcgttgcgc tcactgcccg ctttccagtc gggaaacctg tcgtgccagc tgcattaatg    7020
aatcggccaa cgcgcgggga gaggcggttt gcgtattggg cgctcttccg cttcctcgct    7080
cactgactcg ctgcgctcgg tcgttcggct gcggcgagcg gtatcagctc actcaaaggc    7140
ggtaatacgg ttatccacag aatcagggga taacgcagga agaacatgt gagcaaaagg     7200
ccagcaaaag gccaggaacc gtaaaaaggc cgcgttgctg gcgtttttcc ataggctccg    7260
cccccctgac gagcatcaca aaaatcgacg ctcaagtcag aggtggcgaa acccgacagg    7320
actataaaga taccaggcgt ttccccctgg aagctccctc gtgcgctctc ctgttccgac    7380
cctgccgctt accggatacc tgtccgcctt tctcccttcg ggaagcgtgg cgctttctca    7440
tagctcacgc tgtaggtatc tcagttcggt gtaggtcgtt cgctccaagc tgggctgtgt    7500
gcacgaaccc cccgttcagc ccgaccgctg cgccttatcc ggtaactatc gtcttgagtc    7560
caacccggta agacacgact tatcgccact ggcagcagcc actggtaaca ggattagcag    7620
agcgaggtat gtaggcggtg ctacagagtt cttgaagtgg tggcctaact acggctacac    7680
tagaaggaca gtatttggta tctgcgctct gctgaagcca gttaccttcg gaaaaagagt    7740
tggtagctct tgatccggca aacaaaccac cgctggtagc ggtggttttt tgtttgcaa    7800
gcagcagatt acgcgcagaa aaaaaggatc tcaagaagat cctttgatct tttctacggg    7860
gtctgacgct cagtggaacg aaaactcacg ttaagggatt ttggtcatga gattatcaaa    7920
aaggatcttc acctagatcc ttttaaatta aaaatgaagt tttaaatcaa tctaaagtat    7980
atatgagtaa acttggtctg acagttacca atgcttaatc agtgaggcac ctatctcagc    8040
gatctgtcta tttcgttcat ccatagttgc ctgactcccc gtcgtgtaga taactacgat    8100
acgggagggc ttaccatctg gccccagtgc tgcaatgata ccgcgagacc cacgctcacc    8160
ggctccagat ttatcagcaa taaaccagcc agccggaagg gccgagcgca gaagtggtcc    8220
tgcaacttta tccgcctcca tccagtctat taattgttgc cgggaagcta gagtaagtag    8280
ttcgccagtt aatagtttgc gcaacgttgt tgccattgct acaggcatcg tggtgtcacg    8340
ctcgtcgttt ggtatggctt cattcagctc cggttcccaa cgatcaaggc gagttacatg    8400
atcccccatg ttgtgcaaaa aagcggttag ctccttcggt cctccgatcg ttgtcagaag    8460
taagttggcc gcagtgttat cactcatggt tatggcagca ctgcataatt ctcttactgt    8520
catgccatcc gtaagatgct tttctgtgac tggtgagtac tcaaccaagt cattctgaga    8580
atagtgtatg cggcgaccga gttgctcttg cccggcgtca atacgggata ataccgcgcc    8640
acatagcaga actttaaaag tgctcatcat tggaaaacgt tcttcggggc gaaaactctc    8700
aaggatctta ccgctgttga gatccagttc gatgtaaccc actcgtgcac ccaactgatc    8760
ttcagcatct tttactttca ccagcgtttc tgggtgagca aaaacaggaa ggcaaaatgc    8820
cgcaaaaaag ggaataaggg cgacacgaaa atgttgaata ctcatactct tcctttttca    8880
atattattga agcatttatc agggttattg tctcatgagc ggatacatat ttgaatgtat    8940
ttagaaaaat aaacaaatag gggttccgcg cacatttccc cgaaaagtgc cac           8993
```

<210> SEQ ID NO 6  
<211> LENGTH: 5488  
<212> TYPE: DNA  
<213> ORGANISM: Artificial Sequence  
<220> FEATURE:  
<223> OTHER INFORMATION: pGUS  
<220> FEATURE:  
<221> NAME/KEY: gene
<222> LOCATION: (707)..(2518)
<223> OTHER INFORMATION: GUS
<220> FEATURE:
<221> NAME/KEY: terminator
<222> LOCATION: (2519)..(3259)
<223> OTHER INFORMATION: GstA1 terminator

<400> SEQUENCE: 6

```
ctaaattgta agcgttaata ttttgttaaa attcgcgtta aattttttgtt aaatcagctc      60
atttttaac caataggccg aaatcggcaa atcccttat aaatcaaaag aatagaccga        120
gatagggttg agtgttgttc cagtttggaa caagagtcca ctattaaaga acgtggactc      180
caacgtcaaa gggcgaaaaa ccgtctatca gggcgatggc ccactacgtg aaccatcacc      240
ctaatcaagt tttttggggt cgaggtgccg taaagcacta atcggaacc ctaaagggag       300
cccccgattt agagcttgac ggggaaagcc ggcgaacgtg gcgagaaagg aagggaagaa      360
agcgaaagga gcgggcgcta gggcgctggc aagtgtagcg gtcacgctgc gcgtaaccac      420
cacacccgcc gcgcttaatg cgccgctaca gggcgcgtcc cattcgccat tcaggctgcg      480
caactgttgg gaagggcgat cggtgcgggc ctcttcgcta ttacgccagc tggcgaaagg      540
gggatgtgct gcaaggcgat taagttgggt aacgccaggg ttttcccagt cacgacgttg      600
taaaacgacg gccagtgagc gcgcgtaata cgactcacta tagggcgaat tgggtaccgg      660
gccccccctc gagcacattt aaatcaaccc gggtggtcag tcccttatgt tacgtcctgt      720
agaaaccca acccgtgaaa tcaaaaaact cgacggcctg tgggcattca gtctggatcg      780
cgaaaactgt ggaattgatc agcgttgtg ggaaagcgcg ttacaagaaa gccgggcaat      840
tgctgtgcca ggcagttta acgatcagtt cgccgatgca gatattcgta attatgcggg       900
caacgtctgg tatcagcgcg aagtctttat accgaaaggt tgggcaggcc agcgtatcgt      960
gctgcgtttc gatgcggtca ctcattacgg caaagtgtgg gtcaataatc aggaagtgat     1020
ggagcatcag ggcggctata cgccatttga agccgatgtc acgccgtatg ttattgccgg     1080
gaaaagtgta cgtatcaccg tttgtgtgaa caacgaactg aactggcaga ctatcccgcc     1140
gggaatggtg attaccgacg aaaacggcaa gaaaaagcag tcttacttcc atgatttctt     1200
taactatgcc ggaatccatc gcagcgtaat gctctacacc acgccgaaca cctgggtgga     1260
cgatatcacc gtggtgacgc atgtcgcgca agactgtaac cacgcgtctg ttgactggca     1320
ggtggtggcc aatggtgatg tcagcgttga actgcgtgat gcggatcaac aggtggttgc     1380
aactggacaa ggcactagcg ggactttgca agtggtgaat ccgcacctct ggcaaccggg     1440
tgaaggttat ctctatgaac tgtgcgtcac agccaaaagc cagacagagt gtgatatcta     1500
cccgcttcgc gtcggcatcc ggtcagtggc agtgaagggc gaacagttcc tgattaacca     1560
caaaccgttc tactttactg gctttggtcg tcatgaagat gcggacttgc gtggcaaagg     1620
attcgataac gtgctgatgg tgcacgacca cgcattaatg gactggattg ggccaactc      1680
ctaccgtacc tcgcattacc cttacgctga agagatgctc gactgggcag atgaacatgg     1740
catcgtggtg attgatgaaa ctgctgctgt cggctttaac ctctctttag gcattggttt     1800
cgaagcgggc aacaagccga agaactgta cagcgaagag gcagtcaacg ggaaactca      1860
gcaagcgcac ttacaggcga ttaaagagct gatagcgcgt gacaaaaacc acccaagcgt     1920
ggtgatgtgg agtattgcca acgaaccgga tacccgtccg caaggtgcac gggaatattt     1980
cgcgccactg gcggaagcaa cgcgtaaact cgacccgacg cgtccgatca cctgcgtcaa     2040
tgtaatgttc tgcgacgctc acaccgatac catcagcgat ctctttgatg tgctgtgcct     2100
```

```
gaaccgttat tacgyatggt atgtccaaag cggcgatttg gaaacggcag agaaggtact    2160
ggaaaaagaa cttctggcct ggcaggagaa actgcatcag ccgattatca tcaccgaata    2220
cggcgtggat acgttagccg ggctgcactc aatgtacacc gacatgtgga gtgaagagta    2280
tcagtgtgca tggctggata tgtatcaccg cgtctttgat cgcgtcagcg ccgtcgtcgg    2340
tgaacaggta tggaatttcg ccgattttgc gacctcgcaa ggcatattgc gcgttggcgg    2400
taacaagaaa gggatcttca ctcgcgaccg caaaccgaag tcggcggctt ttctgctgca    2460
aaaacgctgg actggcatga acttcggtga aaaaccgcag cagggaggca aacaatgaga    2520
gctactagta tgcctaccga gtttaagcta ggtgcgcagt actaggtgtt tatgcactcc    2580
gcgcgggtgt gtgccgtgcc gtgccgtgcc gtgccggtga tgattccgtt caagaaaaga    2640
gacctccctc ccgtgggtgg gtgatcatct gcccgtctac ttccagtagt atacgctttc    2700
agtttcagca gcacgaggag tccgcttgcg cttctgttcg tgcgctggat tccttgcttt    2760
aatttatgca ctagtactag ttagtaaata acaacggac tggtcaatgc tgctaatccg    2820
tactgtacgt cctatatagt agtaccccac tagagatcag tatatatata catcttggat    2880
acgtgtgcat ttgcatgcaa atatatatgg acagggataa ctggcacatg tgtgcccgtt    2940
aggaaaatta cgatcgctct ccttcggtcg gtggcccgct cgctcgatcg agcgttcctt    3000
cggtcggtgt cccgctcgcc cttcggtccg tggcccgctc gctcgatcga gcgttccttc    3060
ggtcggtgtc ccgctcgctc gatcgagcgt tgaggccagt tggctcgatc gctccgcttt    3120
gatcgagttg tgaatgcttt caccggtttt ttttcttct gatttttatt ttcagaacgg    3180
tctactaaat agtcactaca cccaataacc aactcggcca tcctaccttg ttatccacaa    3240
tacgtgaaca acgaagttg aattctagtc tacgcggccg cgagctccag cttttgttcc    3300
ctttagtgag ggttaattgc gcgcttggcg taatcatggt catagctgtt tcctgtgtga    3360
aattgttatc cgctcacaat tccacacaac atacgagccg gaagcataaa gtgtaaagcc    3420
tgggtgcct aatgagtgag ctaactcaca ttaattgcgt tgcgctcact gcccgctttc    3480
cagtcgggaa acctgtcgtg ccagctgcat taatgaatcg gccaacgcgc ggggagaggc    3540
ggtttgcgta ttgggcgctc ttccgcttcc tcgctcactg actcgctgcg ctcggtcgtt    3600
cggctgcggc gagcggtatc agctcactca aaggcggtaa tacggttatc cacagaatca    3660
ggggataacg caggaaagaa catgtgagca aaaggccagc aaaaggccag gaaccgtaaa    3720
aaggccgcgt tgctggcgtt tttccatagg ctccgccccc ctgacgagca tcacaaaaat    3780
cgacgctcaa gtcagaggtg gcgaaacccg acaggactat aaagatacca ggcgtttccc    3840
cctggaagct ccctcgtgcg ctctcctgtt ccgaccctgc cgcttaccgg atacctgtcc    3900
gcctttctcc cttcgggaag cgtggcgctt tctcatagct cacgctgtag gtatctcagt    3960
tcggtgtagg tcgttcgctc caagctgggc tgtgtgcacg aacccccgt tcagcccgac    4020
cgctgcgcct tatccggtaa ctatcgtctt gagtccaacc cggtaagaca cgacttatcg    4080
ccactggcag cagccactgg taacaggatt agcagagcga ggtatgtagg cggtgctaca    4140
gagttcttga agtggtggcc taactacggc tacactagaa ggacagtatt tggtatctgc    4200
gctctgctga agccagttac cttcggaaaa agagttggta gctcttgatc cggcaaacaa    4260
accaccgctg gtagcggtgg ttttttgtt tgcaagcagc agattacgcg cagaaaaaaa    4320
ggatctcaag aagatccttt gatcttttct acggggtctg acgctcagtg gaacgaaaac    4380
tcacgttaag ggattttggt catgagatta tcaaaaagga tcttcaccta gatcctttta    4440
aattaaaaat gaagttttaa atcaatctaa agtatatatg agtaaacttg gtctgacagt    4500
```

```
taccaatgct taatcagtga ggcacctatc tcagcgatct gtctatttcg ttcatccata    4560
gttgcctgac tccccgtcgt gtagataact acgatacggg agggcttacc atctggcccc    4620
agtgctgcaa tgataccgcg agacccacgc tcaccggctc cagatttatc agcaataaac    4680
cagccagccg gaagggccga gcgcagaagt ggtcctgcaa ctttatccgc ctccatccag    4740
tctattaatt gttgccggga agctagagta agtagttcgc cagttaatag tttgcgcaac    4800
gttgttgcca ttgctacagg catcgtggtg tcacgctcgt cgtttggtat ggcttcattc    4860
agctccggtt cccaacgatc aaggcgagtt acatgatccc ccatgttgtg caaaaaagcg    4920
gttagctcct tcggtcctcc gatcgttgtc agaagtaagt tggccgcagt gttatcactc    4980
atggttatgg cagcactgca taattctctt actgtcatgc catccgtaag atgcttttct    5040
gtgactggtg agtactcaac caagtcattc tgagaatagt gtatgcggcg accgagttgc    5100
tcttgcccgg cgtcaatacg ggataatacc gcgccacata gcagaacttt aaaagtgctc    5160
atcattggaa aacgttcttc ggggcgaaaa ctctcaagga tcttaccgct gttgagatcc    5220
agttcgatgt aacccactcg tgcacccaac tgatcttcag catcttttac tttcaccagc    5280
gtttctgggt gagcaaaaac aggaaggcaa aatgccgcaa aaaagggaat aagggcgaca    5340
cggaaatgtt gaatactcat actcttcctt tttcaatatt attgaagcat ttatcagggt    5400
tattgtctca tgagcggata catatttgaa tgtatttaga aaaataaaca atagggggtt    5460
ccgcgcacat ttccccgaaa agtgccac                                       5488

<210> SEQ ID NO 7
<211> LENGTH: 5646
<212> TYPE: DNA
<213> ORGANISM: Artificial Sequence
<220> FEATURE:
<223> OTHER INFORMATION: pIntronGUS
<220> FEATURE:
<221> NAME/KEY: misc_feature
<222> LOCATION: (694)..(846)
<223> OTHER INFORMATION: WIR1 part of 5'CDS + intron
<220> FEATURE:
<221> NAME/KEY: gene
<222> LOCATION: (865)..(2676)
<223> OTHER INFORMATION: GUS
<220> FEATURE:
<221> NAME/KEY: terminator
<222> LOCATION: (2677)..(3417)
<223> OTHER INFORMATION: GstA1 terminator

<400> SEQUENCE: 7
ctaaattgta agcgttaata ttttgttaaa attcgcgtta aatttttgtt aaatcagctc      60
attttttaac caataggccg aaatcggcaa aatcccttat aaatcaaaag aatagaccga    120
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt ttttttgggt cgaggtgccg taaagcacta aatcggaacc ctaaagggag    300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat tgggtaccgg    660
```

```
gcccccctc gagctcattt aaatcctctg cagggagcca cggccgtcca cgacgccgcc        720
gcctcaggtc agtcgtcgga cggtgtccgt tcatttcctc cccattttg taattgatta        780 acttgttata catgctgacc tcgacctgct gaataacgtc cgtccatggt ttcccgtcca        840
ggcaccccgg gtggtcagtc ccttatgtta cgtcctgtag aaaccccaac ccgtgaaatc       900
aaaaaactcg acggcctgtg gcattcagt ctggatcgcg aaaactgtgg aattgatcag        960
cgttggtggg aaagcgcgtt acaagaaagc cgggcaattg ctgtgccagg cagttttaac      1020
gatcagttcg ccgatgcaga tattcgtaat tatgcgggca acgtctggta tcagcgcgaa      1080
gtctttatac cgaaaggttg gcaggccag cgtatcgtgc tgcgtttcga tgcggtcact       1140
cattacggca aagtgtgggt caataatcag gaagtgatgg agcatcaggg cggctatacg      1200
ccatttgaag ccgatgtcac gccgtatgtt attgccggga aaagtgtacg tatcaccgtt      1260
tgtgtgaaca cgaactgaa ctggcagact atcccgccgg gaatggtgat taccgacgaa       1320
aacggcaaga aaaagcagtc ttacttccat gatttcttta actatgccgg aatccatcgc      1380
agcgtaatgc tctacaccac gccgaacacc tgggtggacg atatcaccgt ggtgacgcat      1440
gtcgcgcaag actgtaacca cgcgtctgtt gactggcagg tggtggccaa tggtgatgtc      1500
agcgttgaac tgcgtgatgc ggatcaacag gtggttgcaa ctggacaagg cactagcggg      1560
actttgcaag tggtgaatcc gcacctctgg caacccgggtg aaggttatct ctatgaactg     1620
tgcgtcacag ccaaaagcca gacagagtgt gatatctacc cgcttcgcgt cggcatccgg     1680
tcagtggcag tgaagggcga acagttcctg attaaccaca aaccgttcta ctttactggc      1740
tttggtcgtc atgaagatgc ggacttgcgt ggcaaaggat tcgataacgt gctgatggtg      1800
cacgaccacg cattaatgga ctggattggg gccaactcct accgtacctc gcattaccct      1860
tacgctgaag agatgctcga ctgggcagat gaacatggca tcgtggtgat tgatgaaact      1920
gctgctgtcg gctttaacct ctctttaggc attggtttcg aagcgggcaa caagccgaaa      1980
gaactgtaca gcgaagaggc agtcaacggg gaaactcagc aagcgcactt acaggcgatt      2040
aaagagctga tagcgcgtga caaaaaccac ccaagcgtgg tgatgtggag tattgccaac      2100
gaaccggata cccgtccgca aggtgcacgg gaatatttcg cgccactggc ggaagcaacg      2160
cgtaaactcg acccgacgcg tccgatcacc tgcgtcaatg taatgttctg cgacgctcac      2220
accgatacca tcagcgatct cttttgatgtg ctgtgcctga accgttatta cggatggtat    2280
gtccaaagcg gcgatttgga aacggcagag aaggtactgg aaaaagaact tctggcctgg     2340
caggagaaac tgcatcagcc gattatcatc accgaatacg gcgtggatac gttagccggg     2400
ctgcactcaa tgtacaccga catgtggagt gaagagtatc agtgtgcatg gctggatatg     2460
tatcaccgcg tctttgatcg cgtcagcgcc gtcgtcggtg aacaggtatg gaatttcgcc     2520
gattttgcga cctcgcaagg catattgcgc gttggcggta acaagaaagg gatcttcact     2580
cgcgaccgca aaccgaagtc ggcggctttt ctgctgcaaa aacgctggac tggcatgaac     2640
ttcggtgaaa aaccgcagca gggaggcaaa caatgagagc tactagtatg cctaccgagt     2700
ttaagctagg tgcgcagtac taggtgttta tgcactccgc gcgggtgtgt gccgtgccgt    2760
gccgtgccgt gccggtgatg attccgttca agaaaagaga cctccctccc gtgggtgggt     2820
gatcatctgc ccgtctactt ccagtagtat acgctttcag tttcagcagc acgaggagtc     2880
cgcttgcgct tctgttcgtg cgctggattc cttgctttaa tttatgcact agtactagtt     2940
agtaaataaa caacgactg gtcaatgctg ctaatccgta ctgtacgtcc tatatagtag     3000
taccccacta gagatcagta tatatataca tcttggatac gtgtgcattt gcatgcaaat    3060
```

```
atatatggac agggataact ggcacatgtg tgcccgttag gaaaattacg atcgctctcc    3120
ttcggtcggt ggcccgctcg ctcgatcgag cgttccttcg gtcggtgtcc cgctcgccct    3180
tcggtccgtg gcccgctcgc tcgatcgagc gttccttcgg tcggtgtccc gctcgctcga    3240
tcgagcgttg aggccagttg gctcgatcgc tccgctttga tcgagttgtg aatgctttca    3300
ccggtttttt tttcttctga ttttattttt cagaacggtc tactaaatag tcactcacc     3360 caataaccaa ctcggccatc ctaccttgtt atccacaata cgtgaacaac ggaagttgaa    3420
ttctagtcta cgcggccgcg agctccagct tttgttccct ttagtgaggg ttaattgcgc    3480
gcttggcgta atcatggtca tagctgtttc ctgtgtgaaa ttgttatccg ctcacaattc    3540
cacacaacat acgagccgga agcataaagt gtaaagcctg gggtgcctaa tgagtgagct    3600
aactcacatt aattgcgttg cgctcactgc ccgctttcca gtcgggaaac ctgtcgtgcc    3660
agctgcatta atgaatcggc caacgcgcgg ggagaggcgg tttgcgtatt gggcgctctt    3720
ccgcttcctc gctcactgac tcgctgcgct cggtcgttcg gctgcggcga gcggtatcag    3780
ctcactcaaa ggcggtaata cggttatcca cagaatcagg ggataacgca ggaaagaaca    3840
tgtgagcaaa aggccagcaa aaggccagga accgtaaaaa ggccgcgttg ctggcgtttt    3900
tccataggct ccgcccccct gacgagcatc acaaaaatcg acgctcaagt cagaggtggc    3960
gaaacccgac aggactataa agataccagg cgtttccccc tggaagctcc ctcgtgcgct    4020
ctcctgttcc gaccctgccg cttaccggat acctgtccgc ctttctccct tcgggaagcg    4080
tggcgctttc tcatagctca cgctgtaggt atctcagttc ggtgtaggtc gttcgctcca    4140
agctgggctg tgtgcacgaa ccccccgttc agcccgaccg ctgcgcctta tccggtaact    4200
atcgtcttga gtccaacccg gtaagacacg acttatcgcc actggcagca gccactggta    4260
acaggattag cagagcgagg tatgtaggcg gtgctacaga gttcttgaag tggtggccta    4320
actacggcta cactagaagg acagtatttg gtatctgcgc tctgctgaag ccagttacct    4380
tcggaaaaag agttggtagc tcttgatccg gcaaacaaac caccgctggt agcggtggtt    4440
tttttgtttg caagcagcag attacgcgca gaaaaaaagg atctcaagaa gatcctttga    4500
tcttttctac ggggtctgac gctcagtgga acgaaaactc acgttaaggg attttggtca    4560
tgagattatc aaaaaggatc ttcacctaga tccttttaaa ttaaaaatga agttttaaat    4620
caatctaaag tatatatgag taaacttggt ctgacagtta ccaatgctta atcagtgagg    4680
cacctatctc agcgatctgt ctatttcgtt catccatagt tgcctgactc cccgtcgtgt    4740
agataactac gatacgggag ggcttaccat ctggccccag tgctgcaatg ataccgcgag    4800
acccacgctc accggctcca gatttatcag caataaacca gccagccgga agggccgagc    4860
gcagaagtgg tcctgcaact ttatccgcct ccatccagtc tattaattgt tgccgggaag    4920
ctagagtaag tagttcgcca gttaatagtt tgcgcaacgt tgttgccatt gctacaggca    4980
tcgtggtgtc acgctcgtcg tttggtatgg cttcattcag ctccggttcc caacgatcaa    5040
ggcgagttac atgatccccc atgttgtgca aaaaagcggt tagctccttc ggtcctccga    5100
tcgttgtcag aagtaagttg gccgcagtgt tatcactcat ggttatggca gcactgcata    5160
attctcttac tgtcatgcca tccgtaagat gcttttctgt gactggtgag tactcaacca    5220
agtcattctg agaatagtgt atgcggcgac cgagttgctc ttgcccggcg tcaatacggg    5280
ataataccgc gccacatagc agaactttaa aagtgctcat cattggaaaa cgttcttcgg    5340
ggcgaaaact ctcaaggatc ttaccgctgt tgagatccag ttcgatgtaa cccactcgtg    5400
```

```
cacccaactg atcttcagca tcttttactt tcaccagcgt ttctgggtga gcaaaaacag    5460
gaaggcaaaa tgccgcaaaa aagggaataa gggcgacacg gaaatgttga atactcatac    5520
tcttcctttt tcaatattat tgaagcattt atcagggtta ttgtctcatg agcggataca    5580
tatttgaatg tatttagaaa aataaacaaa taggggttcc gcgcacattt ccccgaaaag    5640
tgccac                                                               5646

<210> SEQ ID NO 8
<211> LENGTH: 20
<212> TYPE: DNA
<213> ORGANISM: Artificial Sequence
<220> FEATURE:
<223> OTHER INFORMATION: forward primer for promoter

<400> SEQUENCE: 8
cgtgcgtaaa ttaagggcat                                                  20

<210> SEQ ID NO 9
<211> LENGTH: 18
<212> TYPE: DNA
<213> ORGANISM: Artificial Sequence
<220> FEATURE:
<223> OTHER INFORMATION: reverse primer for promoter

<400> SEQUENCE: 9
cagctccttt gggtcttg                                                    18

<210> SEQ ID NO 10
<211> LENGTH: 20
<212> TYPE: DNA
<213> ORGANISM: Artificial Sequence
<220> FEATURE:
<223> OTHER INFORMATION: oligonucleotide

<400> SEQUENCE: 10
tcgagcacat ttaaatcaac                                                  20

<210> SEQ ID NO 11
<211> LENGTH: 20
<212> TYPE: DNA
<213> ORGANISM: Artificial Sequence
<220> FEATURE:
<223> OTHER INFORMATION: oligonucleotide

<400> SEQUENCE: 11
ccgggttgat ttaaatgtgc                                                  20

<210> SEQ ID NO 12
<211> LENGTH: 24
<212> TYPE: DNA
<213> ORGANISM: Artificial Sequence
<220> FEATURE:
<223> OTHER INFORMATION: oligonucleotide

<400> SEQUENCE: 12
tcgagctcat ttaaatcctc tgca                                             24

<210> SEQ ID NO 13
<211> LENGTH: 16
<212> TYPE: DNA
<213> ORGANISM: Artificial Sequence
<220> FEATURE:
<223> OTHER INFORMATION: oligonucleotide

<400> SEQUENCE: 13
```

```
gaggatttaa atgagc                                                     16

<210> SEQ ID NO 14
<211> LENGTH: 20
<212> TYPE: DNA
<213> ORGANISM: Artificial Sequence
<220> FEATURE:
<223> OTHER INFORMATION: oligonucleotide

<400> SEQUENCE: 14
ggatttgtca cgtccaacct                                                 20

<210> SEQ ID NO 15
<211> LENGTH: 20
<212> TYPE: DNA
<213> ORGANISM: Artificial Sequence
<220> FEATURE:
<223> OTHER INFORMATION: oligonucleotide

<400> SEQUENCE: 15
attggcaatt gtgatagccc                                                 20

<210> SEQ ID NO 16
<211> LENGTH: 2953
<212> TYPE: DNA
<213> ORGANISM: Hordeum vulgare
<220> FEATURE:
<221> NAME/KEY: promoter
<222> LOCATION: (1)..(2953)

<400> SEQUENCE: 16
aaatgtgaat gtggaatgtg caaaagttgc ttcctggact tgttgttctg gtctctcgct     60
ttctggtgca tgaaattaga aatatacagt tcctccatgt aatattttta gcttcctttt    120
ggttcaaagc tcttgtaagt tcgattgacg gctgctttga tggaaatcga tgaggtggct    180
cattttatct aaattcttat gagtagtatt tttgattttc ttaagttggg aactaaaaac    240
acgttttttt actaagtttt ggaaactggg cacaacggag tcgagatttt aaacattagc    300
tccaacatac atataaaaaa tatgcataaa tgtagaaaat aaacttatta ccggaagtgc    360
ctaatgacac acctcgagca tgctggcgga agggagcaga tgagaagctg gaccacctta    420
agactcaacc aggaccgatg acgacattca tccacgagcc acctggaaga aaacacctga    480
cttcgtcgta ctgtcacctt tgaactacag ttgcatgtcg gagacgaccc gctgcttaaa    540
ccaagtagtg tcttgaccat accagcagac atgatgaaag gaggacattg ttgcatgtac    600
tacaagatat gtgcatgcaa taccgtgagt catttgattt aaggcagggt cgattggatc    660
gccataccat tccgaacaca ccaccgtaaa tggagagtgt tgattgcaca cattctgtag    720
caacttaaaa gaatggagag tgttagaact agccgcttgc cgtagatcag atcgccgtcg    780
tacgccaaca caactataac cgaaactaga acaaaacctg cacgctacga gctaaaagca    840
agcaagctgg ctggtggatc gattgttggg ctagctagct atggaactga tgtattctgc    900
cgtccggcta gataaatctc aatcggaact acaccaaagt atagcacgca acacacgag    960 ataatcttac aggagaggag atcaagctaa gcagacgact tgtctgtgt agaaaacgat    1020 tgctttacat aacttacatc tctcaactcc tctttgacct cgtgtgcatc agttctcacc    1080
atgaccaagt atacgtatat gatatctaat aaactatgat gatgggtggc gactttcat    1140 gaaaccagcg ctccatgcat tgtgctgact tggttgagat ggataaataa ttgtaattac    1200
tactcagcca tacatcggat gatgcattag cgcttaagca tattaaaaag caaacttgaa    1260
```

-continued

```
aagtttatgc aaaatactat tcagaagcca atagatgatt atttagtaat gtgctcagag   1320
gtttcaacgt gcaagttgaa tgtgcaaacg ttgcttcctt gagtcgttgt tgtggtctgc   1380
ctttccgggg catgtaataa gtagtttacg gtagttcctg gagtatagcc cacatacttg   1440
ggctatactt ctctcagtga taaaacttct ctctgtgtac catcacgagt ttactcatag   1500
atttcttccg taactaatag tgtcaagtta tacacttata tataccttag ttttctctaa   1560
aagaaaccga tataccttac ttgatgtcct tctcttaatc tagaaaggtg ttaattataa   1620
atatttccat cttgagtgtt tgtatcctcc gtatatgttt tgattacagg ctcaaagttt   1680
caattgaagg ttttcttgat gttttttatc ccaatacatc tgggactcca acgggaatat   1740
ttacaacttg cactgagatt cgttgtattc tctgtctcct agaaatttga ggacactgtt   1800
tattttgtga agaaatgaat aagacggacg actctagggc ggtagttatg tttttatgg   1860 ggcactgaac ctttcggcct ttctgttgta attctgaata tgccttattt ttctcgcaaa   1920
aaataaagaa tatgccttgt ttttatgcag tcgtctagct ttgaatgtgt tccagtgtcg   1980
gttttggagc gagtaaataa ctttctgaat gtaagcactt gaacttgagc tatcttgtcg   2040
tgttggcttg aaactgccca gccctggacg agttctcgtt cccggagaag acgatggtgg   2100
tgctgggcag ttaggagggc atcccggtgg acatcatcca ggaggcggtg gacgtgtgcg   2160
tcgagatccc gcagctgggc gtcgtccggt cgctcaacgt ccgtgtcagc gccgccatcg   2220
ccatctggga ctacacccgc cagcagcggg cccgctcctc ctcctcgcgg taggtagctt   2280
cccgctcttc cttgttggag tgtaaatcag ccatgcttgt tgttgtaaga tgcatggacc   2340
tgaacatcca tggcaaaaac tagtcatgaa ccttagtcag gactagattg ttagatttat   2400
gaactgaatt ggtcatgacg aaaattcttt ggcaagaaaa ttttaactgc tcttgctctc   2460
catcgtccat taattaatgt cgttgcttct tccttcaagt actcaaccat ttggagagaa   2520
atttgaccag gcaactgtat atctggttga cgtaatcata tgatacgtat taggtgcgtt   2580
aatgcatgga tcgacgcgcc atgatttctt ccttgtttga cacaatcaaa actattgctc   2640 atagaaaattg ttactaagag gtctacatca catggagtac cttaatttgc ttctctattt   2700
attaaaggga aaaacgtgta tcaaagattt gaatatggct gaccacatct caaaagttta   2760
tgcagactaa tctagtcggc agccaaagac catttctatc cgttgggcgg ttccacttga   2820
ctatgtccat tactcatgag ttccacctgc tcgccatgcc tatataaaaa catacatccc   2880
cagcatgttc caaccatcac tcacccaaca aacatctcag gaatatagga gaaaacaaga   2940
cccaaaggag ctg                                                      2953
```

<210> SEQ ID NO 17
<211> LENGTH: 3116
<212> TYPE: DNA
<213> ORGANISM: Hordeum vulgare
<220> FEATURE:
<221> NAME/KEY: misc_feature
<222> LOCATION: (1)..(3116)
<223> OTHER INFORMATION: Promotor + WIR1a-Exon/Intron

<400> SEQUENCE: 17

```
aaatgtgaat gtggaatgtg caaaagttgc ttccctggact tgttgttctg gtctctcgct     60
ttctggtgca tgaaattaga aatatacagt tcctccatgt aatatttta gcttcctttt    120 ggttcaaagc tcttgtaagt tcgattgacg gctgctttga tggaaatcga tgaggtggct    180
cattttatct aaattcttat gagtagtatt tttgattttc ttaagttggg aactaaaaac    240
```

```
acgtttttt  actaagtttt  ggaaactggg  cacaacggag  tcgagatttt  aaacattagc    300
tccaacatac  atataaaaaa  tatgcataaa  tgtagaaaat  aaacttatta  ccggaagtgc    360
ctaatgacac  acctcgagca  tgctggcgga  agggagcaga  tgagaagctg  gaccacctta    420
agactcaacc  aggaccgatg  acgacattca  tccacgagcc  acctggaaga  aaacacctga    480
cttcgtcgta  ctgtcacctt  tgaactacag  ttgcatgtcg  gagacgaccc  gctgcttaaa    540
ccaagtagtg  tcttgaccat  accagcagac  atgatgaaaa  gaggacattg  ttgcatgtac    600
tacaagatat  gtgcatgcaa  taccgtgagt  catttgattt  aaggcagggt  cgattggatc    660
gccataccat  tccgaacaca  ccaccgtaaa  tggagagtgt  tgattgcaca  cattctgtag    720
caacttaaaa  gaatggagag  tgttagaact  agccgcttgc  cgtagatcag  atcgccgtcg    780
tacgccaaca  caactataac  cgaaactaga  acaaaacctg  cacgctacga  gctaaaagca    840
agcaagctgg  ctggtggatc  gattgttggg  ctagctagct  atggaactga  tgtattctgc    900
cgtccggcta  gataaatctc  aatcggaact  acaccaaagt  atagcacgca  acacacgag    960 ataatcttac  aggagaggag  atcaagctaa  gcagacgact  ttgtctgtgt  agaaaacgat   1020
tgctttacat  aacttacatc  tctcaactcc  tcttttgacct  cgtgtgcatc  agttctcacc   1080
atgaccaagt  atacgtatat  gatatctaat  aaactatgat  gatgggtggc  gacttttcat   1140
gaaaccagcg  ctccatgcat  tgtgctgact  tggttgagat  ggataaataa  ttgtaattac   1200
tactcagcca  tacatcggat  gatgcattag  cgcttaagca  tattaaaaag  caaacttgaa   1260
aagtttatgc  aaaatactat  tcagaagcca  atagatgatt  atttagtaat  gtgctcagag   1320
gtttcaacgt  gcaagttgaa  tgtgcaaacg  ttgcttcctt  gagtcgttgt  tgtggtctgc   1380
cttccggggg  catgtaataa  gtagtttacg  gtagttcctg  gagtatagcc  cacatacttg   1440
ggctatactt  ctctcagtga  taaaacttct  ctctgtgtac  catcacgagt  ttactcatag   1500
atttcttccg  taactaatag  tgtcaagtta  tacacttata  tataccttag  ttttctctaa   1560
aagaaaccga  tataccttac  ttgatgtcct  tctcttaatc  tagaaaggtg  ttaattataa   1620
atatttccat  cttgagtgtt  tgtatcctcc  gtatatgttt  tgattacagg  ctcaaagttt   1680
caattgaagg  ttttcttgat  gttttttatc  ccaatacatc  tgggactcca  acgggaatat   1740
ttacaacttg  cactgagatt  cgttgtattc  tctgtctcct  agaaatttga  ggacactgtt   1800
tattttgtga  agaaatgaat  aagacggacg  actctagggc  ggtagttatg  ttttttatgg   1860
ggcactgaac  ctttcggcct  ttctgttgta  attctgaata  tgccttatttt  ttctcgcaaa   1920 aaataaagaa  tatgccttgt  ttttatgcag  tcgtctagct  ttgaatgtgt  tccagtgtcg   1980
gttttggagc  gagtaaataa  ctttctgaat  gtaagcactt  gaacttgagc  tatcttgtcg   2040
tgttggcttg  aaactgccca  gccctggacg  agttctcgtt  cccggagaag  acgatggtgg   2100
tgctgggcag  ttaggagggc  atcccggtgg  acatcatcca  ggaggcggtg  gacgtgtgcg   2160
tcgagatccc  gcagctgggc  gtcgtccggt  cgctcaacgt  ccgtgtcagc  gccgccatcg   2220
ccatctggga  ctacacccgc  cagcagcggg  cccgctcctc  ctcctcgcgg  taggtagctt   2280
cccgctcttc  cttgttggag  tgtaaatcag  ccatgcttgt  tgttgtaaga  tgcatggacc   2340
tgaacatcca  tggcaaaaac  tagtcatgaa  ccttagtcag  gactagattg  ttagatttat   2400
gaactgaatt  ggtcatgacg  aaaattcttt  ggcaagaaaa  ttttaactgc  tcttgctctc   2460
catcgtccat  taattaatgt  cgttgcttct  tccttcaagt  actcaaccat  ttggagagaa   2520
atttgaccag  gcaactgtat  atctggttga  cgtaatcata  tgatacgtat  taggtgcgtt   2580
aatgcatgga  tcgacgcgcc  atgatttctt  ccttgtttga  cacaatcaaa  actattgctc   2640
```

-continued

```
atagaaattg ttactaagag gtctacatca catggagtac cttaatttgc ttctctattt    2700
attaaaggga aaaacgtgta tcaaagattt gaatatggct gaccacatct caaaagttta    2760
tgcagactaa tctagtcggc agccaaagac catttctatc cgttgggcgg ttccacttga    2820
ctatgtccat tactcatgag ttccacctgc tcgccatgcc tatataaaaa catacatccc    2880
cagcatgttc caaccatcac tcacccaaca aacatctcag gaatatagga gaaacaaga     2940 cccaaaggag ctgatcgaat tcctgcaggg agccacggcc gtccacgacg ccgccgcctc    3000
aggtcagtcg tcggacggtg tccgttcatt tcctccccat ttttgtaatt gattaacttg    3060
ttatacatgc tgacctcgac ctgctgaata acgtccgtcc atggtttccc gtccag        3116
```

<210> SEQ ID NO 18
<211> LENGTH: 16420
<212> TYPE: DNA
<213> ORGANISM: Artificial Sequence
<220> FEATURE:
<223> OTHER INFORMATION: Plasmid p6UGLP4GUS

<400> SEQUENCE: 18

```
tctagtagtc tgcagtgcag cgtgacccgg tcgtgcccct ctctagagat aatgagcatt      60
gcatgtctaa gttataaaaa attaccacat atttttttg tcacacttgt ttgaagtgca     120
gtttatctat ctttatacat atatttaaac tttactctac gaataatata atctatagta    180
ctacaataat atcagtgttt tagagaatca tataaatgaa cagttagaca tggtctaaag    240
gacaattgag tattttgaca acaggactct acagtttat ctttttagtg tgcatgtgtt     300 ctccttttt tttgcaaata gcttcaccta tataatactt catccatttt attagtacat     360
ccatttaggg tttagggtta atggttttta tagactaatt tttttagtac atctatttta    420
ttctatttta gcctctaaat taagaaaact aaaactctat tttagttttt ttatttaata    480
atttagatat aaaatagaat aaaataaagt gactaaaaat taaacaaata ccctttaaga    540
aattaaaaaa actaaggaaa cattttctt gtttcgagta gataatgcca gcctgttaaa     600
cgccgtcgat cgacgagtct aacgacacc aaccagcgaa ccagcagcgt cgcgtcgggc     660
caagcgaagc agacggcacg gcatctctgt cgctgcctct ggacccctct cgagagttcc    720
gctccaccgt tggacttgct ccgctgtcgg catccagaaa ttgcgtggcg gagcggcaga    780
cgtgagccgg cacggcaggc ggcctcctcc tcctctcacg gcaccggcag ctacggggga    840
ttcctttccc accgctcctt cgctttccct tcctcgcccg ccgtaataaa tagacacccc    900
ctccacaccc tcttttcccca acctcgtgtt gttcggagcg cacacacaca caaccagatc    960
tcccccaaat ccacccgtcg gcacctccgc ttcaaggtac gccgctcgtc ctccccccc    1020 cccctctct accttctcta gatcggcgtt ccggtccatg gttagggccc ggtagttcta    1080
cttctgttca tgtttgtgtt agatccgtgt ttgtgttaga tccgtgctgc tagcgttcgt    1140
acacggatgc gacctgtacg tcagacacgt tctgattgct aacttgccag tgtttctctt    1200
tggggaatcc tgggatggct ctagccgttc cgcagacggg atcgatctag ataggtata     1260 catgttgatg tgggttttac tgatgcatat acatgatggc atatgcagca tctattcata    1320
tgctctaacc ttgagtacct atctattata ataaacaagt atgttttata attatttga     1380 tcttgatata cttggatgat ggcatatgca gcagctatat gtggattttt ttagccctgc    1440
cttcatacgc tatttatttg cttggtactg tttcttttgt cgatgctcac cctgttgttt    1500
ggtgttactt ctgcaggtcg agggcccgg ggggcaataa gatatgaaaa agcctgaact    1560
```

```
caccgcgacg tctgtcgaga agtttctgat cgaaaagttc gacagcgtct ccgacctgat    1620
gcagctctcg gagggcgaag aatctcgtgc tttcagcttc gatgtaggag ggcgtggata    1680
tgtcctgcgg gtaaatagct gcgccgatgg tttctacaaa gatcgttatg tttatcggca    1740
ctttgcatcg gccgcgctcc cgattccgga agtgcttgac attggggaat tcagcgagag    1800
cctgacctat tgcatctccc gccgtgcaca gggtgtcacg ttgcaagacc tgcctgaaac    1860
cgaactgccc gctgttctgc agccggtcgc ggaggccatg gatgcgatcg ctgcggccga    1920
tcttagccag acgagcgggt tcggcccatt cggaccgcaa ggaatcggtc aatacactac    1980
atggcgtgat ttcatatgcg cgattgctga tccccatgtg tatcactggc aaactgtgat    2040
ggacgacacc gtcagtgcgt ccgtcgcgca ggctctcgat gagctgatgc tttgggccga    2100
ggactgcccc gaagtccggc acctcgtgca cgcggatttc ggctccaaca atgtcctgac    2160
ggacaatggc cgcataacag cggtcattga ctggagcgag gcgatgttcg gggattccca    2220
atacgaggtc gccaacatct tcttctggag gccgtggttg gcttgtatgg agcagcagac    2280
gcgctacttc gagcggaggc atccggagct tgcaggatcg ccgcggctcc gggcgtatat    2340
gctccgcatt ggtcttgacc aactctatca gagcttggtt gacggcaatt cgatgatgc    2400 agcttgggcg cagggtcgat gcgacgcaat cgtccgatcc ggagccggga ctgtcgggcg    2460
tacacaaatc gcccgcagaa gcgcggccgt ctggaccgat ggctgtgtag aagtactcgc    2520
cgatagtgga aaccgacgcc ccagcactcg tccgagggca aaggaataga gtagatgccg    2580
accggagtcc gcaaaaatca ccagtctctc tctacaaatc tatctctctc tattttctc    2640 cagaataatg tgtgagtagt tcccagataa gggaattagg gttcttatag ggtttcgctc    2700
atgtgttgag catataagaa acccttagta tgtatttgta tttgtaaaat acttctatca    2760
ataaaatttc taattcctaa aaccaaaatc cagtgacctg caggcatgca agctgatcca    2820
ctagaggcca tggcggccgc gtagactaga attcaacttc cgttgttcac gtattgtgga    2880
taacaaggta ggatggccga gttggttatt gggtgtagtg actatttagt agaccgttct    2940
gaaaataaaa atcagaagaa aaaaaaaccg gtgaaagcat tcacaactcg atcaaagcgg    3000
agcgatcgag ccaactggcc tcaacgctcg atcgagcgag cgggacaccg accgaaggaa    3060
cgctcgatcg agcgagcggg ccacggaccg aagggcgagc gggacaccga ccgaaggaac    3120
gctcgatcga gcgagcgggc caccgaccga aggagagcga tcgtaatttt cctaacgggc    3180
acacatgtgc cagttatccc tgtccatata tatttgcatg caaatgcaca cgtatccaag    3240
atgtatatat atactgatct ctagtggggt actactatat aggacgtaca gtacggatta    3300
gcagcattga ccagtccgtt gtttatttac taactagtac tagtgcataa attaaagcaa    3360
ggaatccagc gcacgaacag aagcgcaagc ggactcctcg tgctgctgaa actgaaagcg    3420
tatactactg gaagtagacg ggcagatgat cacccaccca cgggagggag gtctcttttc    3480
ttgaacggaa tcatcaccgg cacggcacgg cacggcacgg cacacacccg cgcggagtgc    3540
ataaacacct agtactgcgc acctagctta aactcggtag gcatactagt agctctcatt    3600
gtttgcctcc ctgctgcggt ttttcaccga agttcatgcc agtccagcgt ttttgcagca    3660
gaaaagccgc cgacttcggt ttgcggtcgc gagtgaagat ccctttcttg ttaccgccaa    3720
cgcgcaatat gccttgcgag gtcgcaaaat cggcgaaatt ccatacctgt tcaccgacga    3780
cggcgctgac gcgatcaaag acgcggtgat acatatccag ccatgcacac tgatactctt    3840
cactccacat gtcggtgtac attgagtgca gcccggctaa cgtatccacg ccgtattcgg    3900
tgatgataat cggctgatgc agtttctcct gccaggccag aagttctttt tccagtacct    3960
```

```
tctctgccgt tccaaatcg ccgctttgga cataccatcc gtaataacgg ttcaggcaca    4020
gcacatcaaa gagatcgctg atggtatcgg tgtgagcgtc gcagaacatt acattgacgc    4080
aggtgatcgg acgcgtcggg tcgagtttac gcgttgcttc cgccagtggc gcgaaatatt    4140
cccgtgcacc ttgcggacgg gtatccggtt cgttggcaat actccacatc accacgcttg    4200
ggtggttttt gtcacgcgct atcagctctt taatcgcctg taagtgcgct tgctgagttt    4260
ccccgttgac tgcctcttcg ctgtacagtt cttctcggctt gttgcccgct tcgaaaccaa    4320
tgcctaaaga gaggttaaag ccgacagcag cagtttcatc aatcaccacg atgccatgtt    4380
catctgccca gtcgagcatc tcttcagcgt aagggtaatg cgaggtacgg taggagttgg    4440
ccccaatcca gtccattaat gcgtggtcgt gcaccatcag cacgttatcg aatcctttgc    4500
cacgcaagtc cgcatcttca tgacgaccaa agccagtaaa gtagaacggt ttgtggttaa    4560
tcaggaactg ttcgcccttc actgccactg accggatgcc gacgcgaagc gggtagatat    4620
cacactctgt ctggcttttg gctgtgacgc acagttcata gagataacct tcacccggtt    4680
gccagaggtg cggattcacc acttgcaaag tcccgctagt gccttgtcca gttgcaacca    4740
cctgttgatc cgcatcacgc agttcaacgc tgacatcacc attggccacc acctgccagt    4800
caacagacgc gtggttacag tcttgcgcga catgcgtcac cacggtgata tcgtccaccc    4860
aggtgttcgg cgtggtgtag agcattacgc tgcgatggat tccggcatag ttaaagaaat    4920
catggaagta agactgcttt ttcttgccgt tttcgtcggt aatcaccatt cccggcggga    4980
tagtctgcca gttcagttcg ttgttcacac aaacggtgat acgtacactt ttcccggcaa    5040
taacatacgg cgtgacatcg gcttcaaatg gcgtatagcc gccctgatgc tccatcactt    5100
cctgattatt gacccacact ttgccgtaat gagtgaccgc atcgaaacgc agcacgatac    5160
gctggcctgc ccaacctttc ggtataaaga cttcgcgctg ataccagacg ttgcccgcat    5220
aattacgaat atctgcatcg gcgaactgat cgttaaaact gcctggcaca gcaattgccc    5280
ggctttcttg taacgcgctt tcccaccaac gctgatcaat tccacagttt tcgcgatcca    5340
gactgaatgc ccacaggccg tcgagttttt tgatttcacg ggttgggtt tctacaggac    5400 gtaacataag ggactgacca cccgggctgc aggaattcga tcagctcctt tgggtcttgt    5460
tttctcctat attcctgaga tgtttgttgg gtgagtgatg gttggaacat gctggggatg    5520
tatgttttta tataggcatg gcgagcaggt ggaactcatg agtaatggac atagtcaagt    5580
ggaaccgccc aacggataga aatggtcttt ggctgccgac tagattagtc tgcataaact    5640
tttgagatgt ggtcagccat attcaaatct ttgatacacg tttttccctt taataaatag    5700
agaagcaaat taaggtactc catgtgatgt agacctctta gtaacaattt ctatgagcaa    5760
tagttttgat tgtgtcaaac aaggaagaaa tcatggcgcg tcgatccatg cattaacgca    5820
cctaatacgg atcatatgat tacgtcaacc agatatacag ttgcctggtc aaatttctct    5880
ccaaatggtt gagtacttga aggaagaagc aacgacatta ttaatggac gatggagagc    5940 aagagcagtt aaaattttct tgccaaagaa ttttcgtcat gaccaattca gttcataaat    6000
ctaacaatct agtcctgact aaggttcatg actagttttt gccatggatg ttcaggtcca    6060
tgcatcttac aacaacaagc atggctgatt tacactccaa caaggaagag cgggaagcta    6120
cctaccgcga ggaggaggag cgggcccgct gctggcgggt gtagtcccag atggcgatgg    6180
cggcgctgac acgacgttg agcgaccgga cgacgcccag ctgcgggatc tcgacgcaca    6240
cgtccaccgc ctcctggatg atgtccaccg ggatgccctc ctaactgccc agcaccacca    6300
```

```
tcgtcttctc cgggaacgag aactcgtcca gggctgggca gtttcaagcc aacacgacaa    6360
gatagctcaa gttcaagtgc ttacattcag aaagttattt actcgctcca aaaccgacac    6420
tggaacacat tcaaagctag acgactgcat aaaaacaagg catattcttt attttttgcg    6480
agaaaaataa ggcatattca gaattacaac agaaaggccg aaaggttcag tgccccataa    6540
aaaacataac taccgcccta gagtcgtccg tcttattcat ttcttcacaa aataaacagt    6600
gtcctcaaat ttctaggaga cagagaatac aacgaatctc agtgcaagtt gtaaatattc    6660
ccgttggagt cccagatgta ttgggataaa aacatcaag aaaaccttca attgaaactt    6720
tgagcctgta atcaaaacat atacggagga tacaaacact caagatggaa atatttataa    6780
ttaacacctt tctagattaa gagaaggaca tcaagtaagg tatatcggtt tcttttagag    6840
aaaactaagg tatatataag tgtataactt gacactatta gttacggaag aaatctatga    6900
gtaaactcgt gatggtacac agagagaagt tttatcactg agagaagtat agcccaagta    6960
tgtgggctat actccaggaa ctaccgtaaa ctacttatta catgccccgg aaaggcagac    7020
cacaacaacg actcaaggaa gcaacgtttg cacattcaac ttgcacgttg aaacctctga    7080
gcacattact aaataatcat ctattggctt ctgaatagta ttttgcataa acttttcaag    7140
tttgcttttt aatatgctta agcgctaatg catcatccga tgtatggctg agtagtaatt    7200
acaattattt atccatctca accaagtcag cacaatgcat ggagcgctgg tttcatgaaa    7260
agtcgccacc catcatcata gtttattaga tatcatatac gtatacttgg tcatggtgag    7320
aactgatgca cacgaggtca agaggagtt gagagatgta agttatgtaa agcaatcgtt    7380
ttctacacag acaaagtcgt ctgcttagct tgatctcctc tcctgtaaga ttatctcgtg    7440
tgtttgcgtg ctatactttg gtgtagttcc gattgagatt tatctagccg gacggcagaa    7500
tacatcagtt ccatagctag ctagcccaac aatcgatcca ccagccagct tgcttgcttt    7560
tagctcgtag cgtgcaggtt ttgttctagt ttcggttata gttgtgttgg cgtacgacgg    7620
cgatctgatc tacggcaagc ggctagttct aacactctcc attcttttaa gttgctacag    7680
aatgtgtgca atcaacactc tccatttacg gtggtgtgtt cggaatggta tggcgatcca    7740
atcgaccctg ccttaaatca aatgactcac ggtattgcat gcacatatct tgtagtacat    7800
gcaacaatgt cctcctttca tcatgtctgc tggtatggtc aagacactac ttggtttaag    7860
cagcgggtcg tctccgacat gcaactgtag ttcaaaggtg acagtacgac gaagtcaggt    7920
gttttcttcc aggtggctcg tggatgaatg tcgtcatcgg tcctggttga gtcttaaggt    7980
ggtccagctt ctcatctgct cccttccgcc agcatgctcg aggtgtgtca ttaggcactt    8040
ccggtaataa gtttattttc tacatttatg catattttt atatgtatgt tggagctaat    8100
gtttaaaatc tcgactccgt tgtgcccagt ttccaaaact tagtaaaaaa acgtgttttt    8160
agttcccaac ttaagaaaat caaaaatact actcataaga atttagataa aatgagccac    8220
ctcatcgatt tccatcaaag cagccgtcaa tcgaacttac aagagctttg aaccaaaagg    8280
aagctaaaaa tattacatgg aggaactgta tatttctaat ttcatgcacc agaaagcgag    8340
agaccagaac aacaagtcca ggaagcaact tttgcacatt ccacattcac atttaaatcc    8400
tgagcacaat cgggctccac ccatcgcata cttcacatgt attgccagat aataatacgt    8460
gttcaacacc agcgtcaaac aaatactgca ttaccaaata atcttgtatt gtttcttttt    8520
tttaacctaa tcatatatta tttcagaata aggggaaaag aacccaaaat attgatcaat    8580
tatgagaaat acgacacagt agaaccaaaa aaaagcatgt gagatcatat cagtgtgata    8640
aaaaacaata ttttttgatta tttaaaaggt agaaatacat tcactgatta caggcacaca    8700
```

```
attacatatg ctccttttat tttataaatt aggatgcata tctaggaact caatcatgcc    8760
cttaatttac gcacgatcaa gcttgaattc ctgcagcccg ggggatccac tagtaaggcc    8820
ttaagggcca gatcttgggc ccggtacccg atcagattgt cgtttcccgc cttcggttta    8880
aactatcagt gtttgacagg atatattggc gggtaaacct aagagaaaag agcgtttatt    8940
agaataatcg atatttaaa agggcgtgaa aaggtttatc cgttcgtcca tttgtatgtg     9000
catgccaacc acagggttcc cctcgggagt gcttggcatt ccgtgcgata atgacttctg    9060
ttcaaccacc caaacgtcgg aaagcctgac gacggagcag cattccaaaa agatcccttg    9120
gctcgtctgg gtcggctaga aggtcgagtg ggctgctgtg gcttgatccc tcaacgcggt    9180
cgcggacgta gcgcagcgcc gaaaaatcct cgatcgcaaa tccgacgctg tcgaaaagcg    9240
tgatctgctt gtcgctcttt cggccgacgt cctggccagt catcacgcgc caaagttccg    9300
tcacaggatg atctggcgcg agttgctgga tctcgccttc aatccgggtc tgtggcggga    9360
actccacgaa aatatccgaa cgcagcaaga tatcgcggtg catctcggtc ttgcctgggc    9420
agtcgccgcc gacgccgttg atgtggacgc cgaaaaggat ctaggtgaag atccttttg    9480
ataatctcat gaccaaaatc ccttaacgtg agttttcgtt ccactgagcg tcagaccccg    9540
tagaaaagat caaggatct cttgagatc cttttttct gcgcgtaatc tgctgcttgc        9600
aaacaaaaaa accaccgcta ccagcggtgg tttgtttgcc ggatcaagag ctaccaactc    9660
tttttccgaa ggtaactggc ttcagcagag cgcagatacc aaatactgtt cttctagtgt    9720
agccgtagtt aggccaccac ttcaagaact ctgtagcacc gcctacatac ctcgctctgc    9780
taatcctgtt accagtggct gctgccagtg gcgataagtc gtgtcttacc gggttggact    9840
caagacgata gttaccggat aaggcgcagc ggtcgggctg aacggggggt tcgtgcacac    9900
agcccagctt ggagcgaacg acctacaccg aactgagata cctacagcgt gagctatgag    9960
aaagcgccac gcttcccgaa gggagaaagg cggacaggta tccggtaagc ggcagggtcg   10020
gaacaggaga gcgcacgagg gagcttccag ggggaaacgc ctggtatctt tatagtcctg   10080
tcgggtttcg ccacctctga cttgagcgtc gatttttgtg atgctcgtca ggggggcgga   10140
gcctatggaa aaacgccagc aacgcggcct ttttacggtt cctggccttt tgctggcctt   10200
ttgctcacat gttctttcct gcgttatccc ctgattctgt ggataaccga ttaccgcctt   10260
tgagtgagct gataccgctc gccgcagccg aacgaccgag cgcagcgagt cagtgagcga   10320
ggaagcggaa gagcgcctga tgcggtattt tctccttacg catctgtgcg gtatttcaca   10380
ccgcatatgg tgcactctca gtacaatctg ctctgatgcc gcatagttaa gccagtatac   10440
actccgctat cgctacgtga ctgggtcatg gctgcgcccc gacacccgcc aacacccgct   10500
gacgcgccct gacgggcttg tctgctcccg gcatccgctt acagacaagc tgtgaccgtc   10560
tccgggagct gcatgtgtca gaggttttca ccgtcatcac cgaaacgcgc gaggcagggg   10620
tacgtcgagg tcgatccaac ccctccgctg ctatagtgca gtcggcttct gacgttcagt   10680
gcagccgtct tctgaaaacg acatgtcgca caagtcctaa gttacgcgac aggctgccgc   10740
cctgcccttt tcctggcgtt ttcttgtcgc gtgttttagt cgcataaagt agaatacttg   10800
cgactagaac cggagacatt acgccatgaa caagagcgcc gccgctggcc tgctgggcta   10860
tgcccgcgtc agcaccgacg accaggactt gaccaaccaa cgggccgaac tgcacgcggc   10920
cggctgcacc aagctgttttt ccgagaagat caccggcacc aggcgcgacc gcccggagct   10980
ggccaggatg cttgaccacc tacgccctgg cgacgttgtg acagtgacca ggctagaccg   11040
```

```
cctggcccgc agcacccgcg acctactgga cattgccgag cgcatccagg aggccggcgc   11100
gggcctgcgt agcctggcag agccgtgggc cgacaccacc acgccggccg gccgcatggt   11160
gttgaccgtg ttcgccggca ttgccgagtt cgagcgttcc ctaatcatcg accgcacccg   11220
gagcgggcgc gaggccgcca aggcgcgagg cgtgaagttt ggcccccgcc ctaccctcac   11280
cccggcacag atcgcgcacg cccgcgagct gatcgaccag gaaggccgca ccgtgaaaga   11340
ggcggctgca ctgcttggcg tgcatcgctc gaccctgtac cgcgcacttg agcgcagcga   11400
ggaagtgacg cccaccgagg ccaggcggcg cggtgccttc cgtgaggacg cattgaccga   11460
ggccgacgcc ctggcggccg ccgagaatga acgccaagag gaacaagcat gaaaccgcac   11520
caggacggcc aggacgaacc gtttttcatt accgaagaga tcgaggcgga gatgatcgcg   11580
gccgggtacg tgttcgagcc gcccgcgcac gtctcaaccg tgcggctgca tgaaatcctg   11640
gccggtttgt ctgatgccaa gctcgcggcc tggccggcga gcttggccgc tgaagaaacc   11700
gagcgccgcc gtctaaaaag gtgatgtgta tttgagtaaa acagcttgcg tcatgcggtc   11760
gctgcgtata tgatgcgatg agtaaataaa caaatacgca aggggaacgc atgaaggtta   11820
tcgctgtact taaccagaaa ggcgggtcag gcaagacgac catcgcaacc catctagccc   11880
gcgccctgca actcgccggg gccgatgttc tgttagtcga ttccgatccc cagggcagtg   11940
cccgcgattg ggcggccgtg cgggaagatc aaccgctaac cgttgtcggc atcgaccgcc   12000
cgacgattga ccgcgacgtg aaggccatcg gccggcgcga cttcgtagtg atcgacggag   12060
cgccccaggc ggcggacttg gctgtgtccg cgatcaaggc agccgacttc gtgctgattc   12120
cggtgcagcc aagcccttac gacatatggg ccaccgccga cctggtggag ctggttaagc   12180
agcgcattga ggtcacggat ggaaggctac aagcggcctt tgtcgtgtcg cgggcgatca   12240
aaggcacgcg catcggcggt gaggttgccg aggcgctggc cgggtacgag ctgcccattc   12300
ttgagtcccg tatcacgcag cgcgtgagct acccaggcac tgccgccgcc ggcacaaccg   12360
ttcttgaatc agaacccgag ggcgacgctg cccgcgaggt ccaggcgctg gccgctgaaa   12420
ttaaatcaaa actcatttga gttaatgagg taaagagaaa atgagcaaaa gcacaaacac   12480
gctaagtgcc ggccgtccga gcgcacgcag cagcaaggct gcaacgttgg ccagcctggc   12540
agacacgcca gccatgaagc gggtcaactt tcagttgccg gcggaggatc acaccaagct   12600
gaagatgtac gcggtacgcc aaggcaagac cattaccgag ctgctatctg aatacatcgc   12660
gcagctacca gagtaaatga gcaaatgaat aaatgagtag atgaatttta gcggctaaag   12720
gaggcggcat ggaaaatcaa gaacaaccag gcaccgacgc cgtggaatgc ccatgtgtg   12780
gaggaacggg cggttggcca ggcgtaagcg gctgggttgt ctgccggccc tgcaatggca   12840
ctggaacccc caagcccgag gaatcggcgt gagcggtcgc aaaccatccg gcccggtaca   12900
aatcggcgcg cgctgggtg atgacctggt ggagaagttg aaggccggcg caggccgccca   12960
gcggcaacgc atcgaggcag aagcacgccc cggtgaatcg tggcaagcgg ccgctgatcg   13020
aatccgcaaa gaatcccggc aaccgccggc agccggtgcg ccgtcgatta ggaagccgcc   13080
caagggcgac gagcaaccag attttttcgt tccgatgctc tatgacgtgg gcacccgcga   13140
tagtcgcagc atcatggacg tggccgtttt ccgtctgtcg aagcgtgacc gacgagctgg   13200
cgaggtgatc cgctacgagc ttccagacgg gcacgtagag gtttccgcag ggccggccgg   13260
catggcgagt gtgtgggatt acgacctggt actgatggcg gtttcccatc taaccgaatc   13320
catgaaccga taccgggaag ggaagggaga caagcccggc cgcgtgttcc gtccacacgt   13380
tgcggacgta ctcaagttct gccggcgagc cgatggcgga aagcagaaag acgacctggt   13440
```

```
agaaacctgc attcggttaa acaccacgca cgttgccatg cagcgtacga agaaggccaa   13500
gaacggccgc ctggtgacgg tatccgaggg tgaagccttg attagccgct acaagatcgt   13560
aaagagcgaa accgggcggc cggagtacat cgagatcgag ctagctgatt ggatgtaccg   13620
cgagatcaca gaaggcaaga acccggacgt gctgacggtt caccccgatt acttttgat    13680
cgatcccggc atcggccgtt ttctctaccg cctggcacgc cgcgccgcag gcaaggcaga   13740
agccagatgg ttgttcaaga cgatctacga acgcagtggc agcgccggag agttcaagaa   13800
gttctgtttc accgtgcgca agctgatcgg gtcaaatgac ctgccggagt acgatttgaa   13860
ggaggaggcg gggcaggctg gcccgatcct agtcatgcgc taccgcaacc tgatcgaggg   13920
cgaagcatcc gccggttcct aatgtacgga gcagatgcta gggcaaattg ccctagcagg   13980
ggaaaaggt cgaaaggtc tctttcctgt ggatagcacg tacattggga acccaaagcc    14040
gtacattggg aaccggaacc cgtacattgg aacccaaag ccgtacattg gaaccggtc     14100
acacatgtaa gtgactgata taaagagaa aaaggcgat ttttccgcct aaaactcttt     14160
aaaacttatt aaaactctta aaacccgcct ggcctgtgca taactgtctg gccagcgcac   14220
agccgaagag ctgcaaaaag cgcctaccct tcggtcgctg cgctccctac gccccgccgc   14280
ttcgcgtcgg cctatcgcgg ccgctggccg ctcaaaaatg ctggcctac ggccaggcaa    14340
tctaccaggg cgcggacaag ccgcgccgtc gccactcgac cgccggcgcc cacatcaagg   14400
caccggtggg tatgcctgac gatgcgtgga gaccgaaacc ttgcgctcgt tcgccagcca   14460
ggacagaaat gcctcgactt cgctgctgcc caaggttgcc gggtgacgca caccgtggaa   14520
acggatgaag gcacgaaccc agtggacata agcctgttcg gttcgtaagc tgtaatgcaa   14580
gtagcgtatg cgctcacgca actggtccag aaccttgacc gaacgcagcg gtggtaacgg   14640
cgcagtggcg gttttcatgg cttgttatga ctgttttttt ggggtacagt ctatgcctcg   14700
ggcatccaag cagcaagcgc gttacgccgt gggtcgatgt tgatgttat ggagcagcaa    14760
cgatgttacg cagcagggca gtcgccctaa acaaagtta aacatcatga gggaagcggt    14820
gatcgccgaa gtatcgactc aactatcaga ggtagttggc gtcatcgagc gccatctcga   14880
accgacgttg ctggccgtac atttgtacgg ctccgcagtg gatggcggcc tgaagccaca   14940
cagtgatatt gatttgctgg ttacggtgac cgtaaggctt gatgaaacaa cgcggcgagc   15000
tttgatcaac gaccttttgg aaacttcggc ttcccctgga gagagcgaga ttctccgcgc   15060
tgtagaagtc accattgttg tgcacgacga catcattccg tggcgttatc agctaagcg    15120
cgaactgcaa tttggagaat ggcagcgcaa tgacattctt gcaggtatct tcgagccagc   15180
cacgatcgac attgatctgg ctatcttgct gacaaaagca agagaacata gcgttgcctt   15240
ggtaggtcca gcggcggagg aactctttga tccggttcct gaacaggatc tatttgaggc   15300
gctaaatgaa accttaacgc tatggaactc gccgcccgac tgggctggcg atgagcgaaa   15360
tgtagtgctt acgttgtccc gcatttggta cagcgcagta accggcaaaa tcgcgccgaa   15420
ggatgtcgct gccgactggg caatggagcg cctgccggcc cagtatcagc ccgtcatact   15480
tgaagctaga caggcttatc ttggacaaga agaagatcgc ttggcctcgc gcgcagatca   15540
gttggaagaa tttgtccact acgtgaaagg cgagatcacc aaggtagtcg gcaaataatg   15600
tctaacaatt cgttcaagcc gacgccgctt cgcggcgcgg cttaactcaa gcgttagatg   15660
cactaagcac ataattgctc acagccaaac tatcaggtca agtctgcttt tattattttt   15720
aagcgtgcat aataagccct acacaaattg ggagatatat catgaaaggc tggctttttc   15780
```

| | |
|---|---|
| ttgttatcgc aatagttggc gaagtaatcg caacatagct tgcttggtcg ttccgcgtga | 15840 |
| acgtcggctc gattgtacct gcgttcaaat actttgcgat cgtgttgcgc gcctgccggg | 15900 |
| tgcgtcggct gatctcacgg atcgactgct tctctcgcaa cgccatccga cggatgatgt | 15960 |
| ttaaaagtcc catgtggatc actccgttgc cccgtcgctc accgtgttgg ggggaaggtg | 16020 |
| cacatggctc agttctcaat ggaaattatc tgcctaaccg gctcagttct gcgtagaaac | 16080 |
| caacatgcaa gctccaccgg gtgcaaagcg gcagcggcgg caggatatat tcaattgtaa | 16140 |
| atggcttcat gtccgggaaa tctacatgga tcagcaatga gtatgatggt caatatggag | 16200 |
| aaaaagaaag agtaattacc aattttttt caattcaaaa atgtagatgt ccgcagcgtt | 16260 |
| attataaaat gaaagtacat tttgataaaa cgacaaatta cgatccgtcg tatttatagg | 16320 |
| cgaaagcaat aaacaaatta ttctaattcg gaaatcttta tttcgacgtg tctacattca | 16380 |
| cgtccaaatg ggggcttaga tgagaaactt cacgatcggc | 16420 |

<210> SEQ ID NO 19
<211> LENGTH: 16572
<212> TYPE: DNA
<213> ORGANISM: Artificial Sequence
<220> FEATURE:
<223> OTHER INFORMATION: Plasmid p6UGLP4IntronGUS

<400> SEQUENCE: 19

| | |
|---|---|
| tctagtagtc tgcagtgcag cgtgacccgg tcgtgcccct ctctagagat aatgagcatt | 60 |
| gcatgtctaa gttataaaaa attaccacat atttttttg tcacacttgt ttgaagtgca | 120 |
| gtttatctat ctttatacat atatttaaac tttactctac gaataatata atctatagta | 180 |
| ctacaataat atcagtgttt tagagaatca tataaatgaa cagttagaca tggtctaaag | 240 |
| gacaattgag tattttgaca acaggactct acagtttat cttttagtg tgcatgtgtt | 300 |
| ctcctttttt tttgcaaata gcttcaccta tataatactt catccatttt attagtacat | 360 |
| ccatttaggg tttagggtta atggttttta tagactaatt tttttagtac atctatttta | 420 |
| ttctatttta gcctctaaat taagaaaact aaaactctat tttagttttt ttatttaata | 480 |
| atttagatat aaaatagaat aaaataaagt gactaaaaat taaacaaata ccctttaaga | 540 |
| aattaaaaaa actaaggaaa cattttctt gtttcgagta gataatgcca gcctgttaaa | 600 |
| cgccgtcgat cgacgagtct aacggacacc aaccagcgaa ccagcagcgt cgcgtcgggc | 660 |
| caagcgaagc agacggcacg gcatctctgt cgctgcctct ggaccctct cgagagttcc | 720 |
| gctccaccgt tggacttgct ccgctgtcgg catccagaaa ttgcgtggcg gagcggcaga | 780 |
| cgtgagccgg cacggcaggc ggcctcctcc tcctctcacg gcaccggcag ctacggggga | 840 |
| ttcctttccc accgctcctt cgctttccct tcctcgcccg ccgtaataaa tagacacccc | 900 |
| ctccacaccc tctttcccca acctcgtgtt gttcggagcg cacacacaca caaccagatc | 960 |
| tccccccaaat ccaccgtcg gcacctccgc ttcaaggtac gccgctcgtc ctccccccc | 1020 |
| cccctctct accttctcta gatcggcgtt ccggtccatg gttagggccc ggtagttcta | 1080 |
| cttctgttca tgtttgtgtt agatccgtgt ttgtgttaga tccgtgctgc tagcgttcgt | 1140 |
| acacggatgc gacctgtacg tcagacacgt tctgattgct aacttgccag tgtttctctt | 1200 |
| tggggaatcc tgggatggct ctagccgttc cgcagacggg atcgatctag gataggtata | 1260 |
| catgttgatg tgggttttac tgatgcatat acatgatggc atatgcagca tctattcata | 1320 |
| tgctctaacc ttgagtacct atctattata ataacaagt atgttttata attatttga | 1380 |
| tcttgatata cttggatgat ggcatatgca gcagctatat gtggatttt ttagccctgc | 1440 |

```
cttcatacgc tatttatttg cttggtactg tttcttttgt cgatgctcac cctgttgttt    1500
ggtgttactt ctgcaggtcg agggccccgg ggggcaataa gatatgaaaa agcctgaact    1560
caccgcgacg tctgtcgaga agtttctgat cgaaaagttc gacagcgtct ccgacctgat    1620
gcagctctcg gagggcgaag aatctcgtgc tttcagcttc gatgtaggag ggcgtggata    1680
tgtcctgcgg gtaaatagct gcgccgatgg ttttctacaaa gatcgttatg tttatcggca    1740
ctttgcatcg gccgcgctcc cgattccgga agtgcttgac attggggaat tcagcgagag    1800
cctgacctat tgcatctccc gccgtgcaca gggtgtcacg ttgcaagacc tgcctgaaac    1860
cgaactgccc gctgttctgc agccggtcgc ggaggccatg gatgcgatcg ctgcggccga    1920
tcttagccag acgagcgggt tcggcccatt cggaccgcaa ggaatcggtc aatacactac    1980
atggcgtgat ttcatatgcg cgattgctga tccccatgtg tatcactggc aaactgtgat    2040
ggacgacacc gtcagtgcgt ccgtcgcgca ggctctcgat gagctgatgc tttgggccga    2100
ggactgcccc gaagtccggc acctcgtgca cgcggatttc ggctccaaca atgtcctgac    2160
ggacaatggc cgcataacag cggtcattga ctggagcgag gcgatgttcg gggattccca    2220
atacgaggtc gccaacatct tcttctggag gccgtggttg gcttgtatgg agcagcagac    2280
gcgctacttc gagcggaggc atccggagct tgcaggatcg ccgcggctcc gggcgtatat    2340
gctccgcatt ggtcttgacc aactctatca gagcttggtt gacggcaatt tcgatgatgc    2400
agcttgggcg cagggtcgat gcgacgcaat cgtccgatcc ggagccggga ctgtcgggcg    2460
tacacaaatc gcccgcagaa gcgcggccgt ctggaccgat ggctgtgtag aagtactcgc    2520
cgatagtgga aaccgacgcc ccagcactcg tccgagggca aaggaataga gtagatgccg    2580
accggagtcc gcaaaaatca ccagtctctc tctacaaatc tatctctctc tattttctc    2640 cagaataatg tgtgagtagt tcccagataa gggaattagg gttcttatag ggtttcgctc    2700
atgtgttgag catataagaa acccttagta tgtatttgta tttgtaaaat acttctatca    2760
ataaaatttc taattcctaa aaccaaaatc cagtgacctg caggcatgca agctgatcca    2820
ctagaggcca tggcggccgc gtagactaga attcaacttc cgttgttcac gtattgtgga    2880
taacaaggta ggatggccga gttggttatt gggtgtagtg actatttagt agaccgttct    2940
gaaaataaaa atcagaagaa aaaaaaaccg gtgaaagcat tcacaactcg atcaaagcgg    3000
agcgatcgag ccaactggcc tcaacgctcg atcgagcgag cgggacaccg accgaaggaa    3060
cgctcgatcg agcgagcggg ccacggaccg aagggcgagc gggacaccga ccgaaggaac    3120
gctcgatcga gcgagcgggc caccgaccga aggagagcga tcgtaatttt cctaacgggc    3180
acacatgtgc cagttatccc tgtccatata tatttgcatg caaatgcaca cgtatccaag    3240
atgtatatat atactgatct ctagtggggt actactatat aggacgtaca gtacggatta    3300
gcagcattga ccagtccgtt gtttatttac taactagtac tagtgcataa attaaagcaa    3360
ggaatccagc gcacgaacag aagcgcaagc ggactcctcg tgctgctgaa actgaaagcg    3420
tatactactg gaagtagacg ggcagatgat cacccaccca cgggagggag gtctcttttc    3480
ttgaacggaa tcatcaccgg cacggcacgg cacggcacgg cacacacccg cgcggagtgc    3540
ataaacacct agtactgcgc acctagctta aactcggtag gcatactagt agctctcatt    3600
gtttgcctcc ctgctgcggt ttttcaccga agttcatgcc agtccagcgt ttttgcagca    3660
gaaaagccgc cgactcggt ttgcggtcgc gagtgaagat ccctttcttg ttaccgccaa    3720
cgcgcaatat gccttgcgag gtcgcaaaat cggcgaaatt ccatacctgt tcaccgacga    3780
```

```
cggcgctgac gcgatcaaag acgcggtgat acatatccag ccatgcacac tgatactctt    3840
cactccacat gtcggtgtac attgagtgca gcccggctaa cgtatccacg ccgtattcgg    3900
tgatgataat cggctgatgc agtttctcct gccaggccag aagttctttt tccagtacct    3960
tctctgccgt ttccaaatcg ccgctttgga cataccatcc gtaataacgg ttcaggcaca    4020
gcacatcaaa gagatcgctg atggtatcgg tgtgagcgtc gcagaacatt acattgacgc    4080
aggtgatcgg acgcgtcggg tcgagtttac gcgttgcttc cgccagtggc gcgaaatatt    4140
cccgtgcacc ttgcggacgg gtatccggtt cgttggcaat actccacatc accacgcttg    4200
ggtggttttt gtcacgcgct atcagctctt taatcgcctg taagtgcgct tgctgagttt    4260
ccccgttgac tgcctcttcg ctgtacagtt ctttcggctt gttgcccgct tcgaaaccaa    4320
tgcctaaaga gaggttaaag ccgacagcag cagtttcatc aatcaccacg atgccatgtt    4380
catctgccca gtcgagcatc tcttcagcgt aagggtaatg cgaggtacgg taggagttgg    4440
ccccaatcca gtccattaat gcgtggtcgt gcaccatcag cacgttatcg aatcctttgc    4500
cacgcaagtc cgcatcttca tgacgaccaa agccagtaaa gtagaacggt tgtggttaa    4560 tcaggaactg ttcgcccttc actgccactg accggatgcc gacgcgaagc gggtagatat    4620
cacactctgt ctggcttttg gctgtgacgc acagttcata gagataacct tcacccggtt    4680
gccagaggtg cggattcacc acttgcaaag tcccgctagt gccttgtcca gttgcaacca    4740
cctgttgatc cgcatcacgc agttcaacgc tgacatcacc attggccacc acctgccagt    4800
caacagacgc gtggttacag tcttgcgcga catgcgtcac cacggtgata tcgtccaccc    4860
aggtgttcgg cgtggtgtag agcattacgc tgcgatggat tccggcatag ttaaagaaat    4920
catggaagta agactgcttt ttcttgccgt tttcgtcggt aatcaccatt cccggcggga    4980
tagtctgcca gttcagttcg ttgttcacac aaacggtgat acgtacactt ttcccggcaa    5040
taacatacgg cgtgacatcg gcttcaaatg gcgtatagcc gccctgatgc tccatcactt    5100
cctgattatt gacccacact ttgccgtaat gagtgaccgc atcgaaacgc agcacgatac    5160
gctggcctgc ccaacctttc ggtataaaga cttcgcgctg ataccagacg ttgcccgcat    5220
aattacgaat atctgcatcg gcgaactgat cgttaaaact gcctggcaca gcaattgccc    5280
ggctttcttg taacgcgctt tcccaccaac gctgatcaat tccacagttt cgcgatcca    5340 gactgaatgc ccacaggccg tcgagttttt tgatttcacg ggttggggtt tctacaggac    5400
gtaacataag ggactgacca cccgggggtgc ctggacggga aaccatggac ggacgttatt    5460
cagcaggtcg aggtcagcat gtataacaag ttaatcaatt acaaaaatgg ggaggaaatg    5520
aacggacacc gtccgacgac tgacctgagg cggcggcgtc gtggacggcc gtggctccct    5580
gcaggaattc gatcagctcc tttgggtctt gttttctcct atattcctga atgtttgtt    5640 gggtgagtga tggttggaac atgctgggga tgtatgtttt tatataggca tggcgagcag    5700
gtggaactca tgagtaatgg acatagtcaa gtggaaccgc ccaacggata gaaatggtct    5760
ttggctgccg actagattag tctgcataaa cttttgagat gtggtcagcc atattcaaat    5820
ctttgataca cgttttttccc tttaataaat agagaagcaa attaaggtac tccatgtgat    5880
gtagacctct tagtaacaat ttctatgagc aatagttttg attgtgtcaa acaaggaaga    5940
aatcatggcg cgtcgatcca tgcattaacg cacctaatac gtatcatatg attacgtcaa    6000
ccagatatac agttgcctgg tcaaatttct ctccaaatgg ttgagtactt gaaggaagaa    6060
gcaacgacat taattaatgg acgatggaga gcaagagcat ttaaaatttt cttgccaaag    6120
aattttcgtc atgaccaatt cagttcataa atctaacaat ctagtcctga ctaaggttca    6180
```

```
tgactagttt ttgccatgga tgttcaggtc catgcatctt acaacaacaa gcatggctga   6240
tttacactcc aacaaggaag agcgggaagc tacctaccgc gaggaggagg agcgggcccg   6300
ctgctggcgg gtgtagtccc agatggcgat ggcggcgctg acacgacgt tgagcgaccg    6360 gacgacgccc agctgcggga tctcgacgca cacgtccacc gcctcctgga tgatgtccac   6420
cgggatgccc tcctaactgc ccagcaccac catcgtcttc tccgggaacg agaactcgtc   6480
cagggctggg cagtttcaag ccaacacgac aagatagctc aagttcaagt gcttacattc   6540
agaaagttat ttactcgctc caaaaccgac actggaacac attcaaagct agacgactgc   6600
ataaaaacaa ggcatattct ttattttttg cgagaaaaat aaggcatatt cagaattaca   6660
acagaaaggc cgaaaggttc agtgccccat aaaaaacata actaccgccc tagagtcgtc   6720
cgtcttattc atttcttcac aaaataaaca gtgtcctcaa atttctagga gacagagaat   6780
acaacgaatc tcagtgcaag ttgtaaatat tcccgttgga gtcccagatg tattgggata   6840
aaaaacatca agaaaacctt caattgaaac tttgagcctg taatcaaaac atatacggag   6900
gatacaaaca ctcaagatgg aaatatttat aattaacacc tttctagatt aagagaagga   6960
catcaagtaa ggtatatcgg tttctttag agaaaactaa ggtatatata agtgtataac    7020
ttgacactat tagttacgga agaaatctat gagtaaactc gtgatggtac acagagagaa   7080
gttttatcac tgagagaagt atagcccaag tatgtgggct atactccagg aactaccgta   7140
aactacttat tacatgcccc ggaaaggcag accacaacaa cgactcaagg aagcaacgtt   7200
tgcacattca acttgcacgt tgaaacctct gagcacatta ctaaataatc atctattggc   7260
ttctgaatag tattttgcat aaacttttca gtttgctttt taatatgct taagcgctaa    7320 tgcatcatcc gatgtatggc tgagtagtaa ttacaattat ttatccatct caaccaagtc   7380
agcacaatgc atggagcgct ggtttcatga aaagtcgcca cccatcatca tagtttatta   7440
gatatcatat acgtatactt ggtcatggtg agaactgatg cacacgaggt caaagaggag   7500
ttgagagatg taagttatgt aaagcaatcg ttttctacac agacaaagtc gtctgcttag   7560
cttgatctcc tctcctgtaa gattatctcg tgtgtttgcg tgctatactt tggtgtagtt   7620
ccgattgaga tttatctagc cggacggcag aatacatcag ttccatagct agctagccca   7680
acaatcgatc caccagccag cttgcttgct tttagctcgt agcgtgcagg ttttgttcta   7740
gtttcggtta tagttgtgtt ggcgtacgac ggcgatctga tctacggcaa gcggctagtt   7800
ctaacactct ccattctttt aagttgctac agaatgtgtg caatcaacac tctccattta   7860
cggtggtgtg ttcggaatgg tatggcgatc caatcgaccc tgccttaaat caaatgactc   7920
acggtattgc atgcacatat cttgtagtac atgcaacaat gtcctccttt catcatgtct   7980
gctggtatgg tcaagacact acttggttta agcagcgggt cgtctccgac atgcaactgt   8040
agttcaaagg tgacagtacg acgaagtcag gtgttttctt ccaggtggct cgtggatgaa   8100
tgtcgtcatc ggtcctggtt gagtcttaag gtggccagc ttctcatctg ctcccttccg    8160
ccagcatgct cgaggtgtgt cattaggcac ttccggtaat aagtttattt tctacattta   8220
tgcatatttt ttatatgtat gttggagcta atgtttaaaa tctcgactcc gttgtgccca   8280
gtttccaaaa cttagtaaaa aaacgtgttt ttagttccca acttaagaaa atcaaaaata   8340
ctactcataa gaatttagat aaaatgagcc acctcatcga tttccatcaa agcagccgtc   8400
aatcgaactt acaagagctt tgaaccaaaa ggaagctaaa aatattacat ggaggaactg   8460
tatatttcta atttcatgca ccagaaagcg agagaccaga acaacaagtc caggaagcaa   8520
```

```
cttttgcaca ttccacattc acatttaaat cctgagcaca atcgggctcc acccatcgca   8580
tacttcacat gtattgccag ataataatac gtgttcaaca ccagcgtcaa acaaatactg   8640
cattaccaaa taatcttgta ttgtttcttt tttttaacct aatcatatat tatttcagaa   8700 taagggaaa agaacccaaa atattgatca attatgagaa atacgacaca gtagaaccaa    8760
aaaaaagcat gtgagatcat atcagtgtga taaaaaacaa tatttttgat tatttaaaag   8820
gtagaaatac attcactgat tacaggcaca caattacata tgctccttt atttttataaa   8880 ttaggatgca tatctaggaa ctcaatcatg cccttaattt acgcacgatc aagcttgaat   8940
tcctgcagcc cggggatcc actagtaagg ccttaagggc cagatcttgg gcccggtacc    9000
cgatcagatt gtcgtttccc gccttcggtt taaactatca gtgtttgaca ggatatattg   9060
gcgggtaaac ctaagagaaa agagcgttta ttagaataat cggatattta aaagggcgtg   9120
aaaaggttta tccgttcgtc catttgtatg tgcatgccaa ccacagggtt ccctcgggga   9180
gtgcttggca ttccgtgcga taatgacttc tgttcaacca cccaaacgtc ggaaagcctg   9240
acgacggagc agcattccaa aaagatccct tggctcgtct gggtcggcta aaggtcgag    9300 tgggctgctg tggcttgatc cctcaacgcg gtcgcgacg tagcgcagcg ccgaaaaatc    9360
ctcgatcgca aatccgacgc tgtcgaaaag cgtgatctgc ttgtcgctct ttcggccgac   9420
gtcctggcca gtcatcacgc gccaaagttc cgtcacagga tgatctggcg cgagttgctg   9480
gatctcgcct tcaatccggg tctgtggcgg gaactccacg aaaatatccg aacgcagcaa   9540
gatatcgcgg tgcatctcgg tcttgcctgg gcagtcgccg ccgacgccgt tgatgtggac   9600
gccgaaaagg atctaggtga agatcctttt tgataatctc atgaccaaaa tcccttaacg   9660
tgagttttcg ttccactgag cgtcagaccc cgtagaaaag atcaaaggat cttcttgaga   9720
tccttttttt ctgcgcgtaa tctgctgctt gcaaacaaaa aaccaccgc taccagcggt    9780 ggtttgtttg ccggatcaag agctaccaac tctttttccg aaggtaactg gcttcagcag   9840
agcgcagata ccaaatactg ttcttctagt gtagccgtag ttaggccacc acttcaagaa   9900
ctctgtagca ccgcctacat acctcgctct gctaatcctg ttaccagtgg ctgctgccag   9960
tggcgataag tcgtgtctta ccgggttgga ctcaagacga tagttaccgg ataaggcgca  10020
gcggtcgggc tgaacggggg gttcgtgcac acagcccagc ttggagcgaa cgacctacac  10080
cgaactgaga tacctacagc gtgagctatg agaaagcgcc acgcttcccg aagggagaaa  10140
ggcggacagg tatccggtaa gcggcagggt cggaacagga gagcgcacga gggagcttcc  10200
agggggaaac gcctggtatc tttatagtcc tgtcgggttt cgccacctct gacttgagcg  10260
tcgatttttg tgatgctcgt cagggggggcg gagcctatgg aaaaacgcca gcaacgcggc  10320 cttttacgg ttcctggcct tttgctggcc ttttgctcac atgttctttc ctgcgttatc    10380
ccctgattct gtggataacc gattaccgcc tttgagtgag ctgataccgc tcgccgcagc  10440
cgaacgaccg agcgcagcga gtcagtgagc gaggaagcgg aagagcgcct gatgcggtat  10500
tttctcctta cgcatctgtg cggtatttca caccgcatat ggtgcactct cagtacaatc  10560
tgctctgatg ccgcatagtt aagccagtat acactccgct atcgctacgt gactgggtca  10620
tggctgcgcc ccgacacccg ccaacacccg ctgacgcgcc ctgacgggct tgtctgctcc  10680
cggcatccgc ttacagacaa gctgtgaccg tctccgggag ctgcatgtgt cagaggtttt  10740
caccgtcatc accgaaacgc gcgaggcagg ggtacgtcga ggtcgatcca accctccgc   10800 tgctatagtg cagtcggctt ctgacgttca gtgcagccgt cttctgaaaa cgacatgtcg  10860
cacaagtcct aagttacgcg acaggctgcc gccctgccct tttcctggcg ttttcttgtc  10920
```

```
gcgtgtttta gtcgcataaa gtagaatact tgcgactaga accggagaca ttacgccatg   10980
aacaagagcg ccgccgctgg cctgctgggc tatgcccgcg tcagcaccga cgaccaggac   11040
ttgaccaacc aacgggccga actgcacgcg gccggctgca ccaagctgtt ttccgagaag   11100
atcaccggca ccaggcgcga ccgcccggag ctggccagga tgcttgacca cctacgccct   11160
ggcgacgttg tgacagtgac caggctagac cgcctggccc gcagcacccg cgacctactg   11220
gacattgccg agcgcatcca ggaggccggc gcgggcctgc gtagcctggc agagccgtgg   11280
gccgacacca ccacgccggc cggccgcatg gtgttgaccg tgttcgccgg cattgccgag   11340
ttcgagcgtt ccctaatcat cgaccgcacc cggagcgggc gcgaggccgc caaggcgcga   11400
ggcgtgaagt ttggcccccg ccctaccctc accccggcac agatcgcgca cgcccgcgag   11460
ctgatcgacc aggaaggccg caccgtgaaa gaggcggctg cactgcttgg cgtgcatcgc   11520
tcgaccctgt accgcgcact tgagcgcagc gaggaagtga cgcccaccga ggccaggcgg   11580
cgcggtgcct tccgtgagga cgcattgacc gaggccgacg ccctggcggc cgccgagaat   11640
gaacgccaag aggaacaagc atgaaaccgc accaggacgg ccaggacgaa ccgttttttca   11700
ttaccgaaga gatcgaggcg gagatgatcg cggccgggta cgtgttcgag ccgcccgcgc   11760
acgtctcaac cgtgcggctg catgaaatcc tggccggttt gtctgatgcc aagctcgcgg   11820
cctggccggc gagcttggcc gctgaagaaa ccgagcgccg ccgtctaaaa aggtgatgtg   11880
tatttgagta aaacagcttg cgtcatgcgg tcgctgcgta tatgatgcga tgagtaaata   11940
aacaaatacg caaggggaac gcatgaaggt tatcgctgta cttaaccaga aaggcgggtc   12000
aggcaagacg accatcgcaa cccatctagc ccgcgccctg caactcgccg gggccgatgt   12060
tctgttagtc gattccgatc cccagggcag tgcccgcgat tgggcggccg tgcgggaaga   12120
tcaaccgcta accgttgtcg gcatcgaccg cccgacgatt gaccgcgacg tgaaggccat   12180
cggccggcgc gacttcgtag tgatcgacgg agcgccccag gcggcggact ggctgtgtc    12240
cgcgatcaag gcagccgact tcgtgctgat tccggtgcag ccaagcccctt acgacatatg   12300
ggccaccgcc gacctggtgg agctggttaa gcagcgcatt gaggtcacgg atggaaggct   12360
acaagcggcc tttgtcgtgt cgcgggcgat caaaggcacg cgcatcggcg gtgaggttgc   12420
cgaggcgctg gccgggtacg agctgcccat tcttgagtcc cgtatcacgc agcgcgtgag   12480
ctacccaggc actgccgccg ccggcacaac cgttcttgaa tcagaacccg agggcgacgc   12540
tgcccgcgag gtccaggcgc tggccgctga aattaaatca aaactcattt gagttaatga   12600
ggtaaagaga aaatgagcaa agcacaaac acgctaagtg ccggccgtcc gagcgcacgc    12660
agcagcaagc tgcaacgtt ggccagcctg gcagacacgc cagccatgaa gcgggtcaac     12720
tttcagttgc cggcggagga tcacaccaag ctgaagatgt acgcggtacg ccaaggcaag   12780
accattaccg agctgctatc tgaatacatc gcgcagctac cagagtaaat gagcaaatga   12840
ataaatgagt agatgaattt tagcggctaa aggaggcggc atggaaaatc aagaacaacc   12900
aggcaccgac gccgtggaat gccccatgtg tggaggaacg ggcggttggc caggcgtaag   12960
cggctgggtt gtctgccggc cctgcaatgg cactggaacc cccaagcccg aggaatcggc   13020
gtgagcggtc gcaaaccatc cggcccggta caaatcggcg cggcgctggg tgatgacctg   13080
gtggagaagt tgaaggccgc gcaggccgcc cagcggcaac gcatcgaggc agaagcacgc   13140
cccggtgaat cgtggcaagc ggccgctgat cgaatccgca aagaatcccg gcaaccgccg   13200
gcagccggtg cgccgtcgat taggaagccg cccaagggcg acgagcaacc agattttttc   13260
```

```
gttccgatgc tctatgacgt gggcacccgc gatagtcgca gcatcatgga cgtggccgtt    13320
ttccgtctgt cgaagcgtga ccgacgagct ggcgaggtga tccgctacga gcttccagac    13380
gggcacgtag aggtttccgc agggccggcc ggcatggcga gtgtgtggga ttacgacctg    13440
gtactgatgg cggtttccca tctaaccgaa tccatgaacc gataccggga agggaaggga    13500
gacaagcccg gccgcgtgtt ccgtccacac gttgcggacg tactcaagtt ctgccggcga    13560
gccgatggcg gaaagcagaa agacgacctg gtagaaacct gcattcggtt aaacaccacg    13620
cacgttgcca tgcagcgtac gaagaaggcc aagaacggcc gcctggtgac ggtatccgag    13680
ggtgaagcct tgattagccg ctacaagatc gtaaagagcg aaaccgggcg gccggagtac    13740
atcgagatcg agctagctga ttggatgtac cgcgagatca cagaaggcaa gaacccggac    13800
gtgctgacgg ttcaccccga ttacttttg atcgatcccg gcatcggccg ttttctctac    13860
cgcctggcac gccgcgccgc aggcaaggca gaagccagat ggttgttcaa gacgatctac    13920
gaacgcagtg gcagcgccgg agagttcaag aagttctgtt tcaccgtgcg caagctgatc    13980
gggtcaaatg acctgccgga gtacgatttg aaggaggagg cggggcaggc tggcccgatc    14040
ctagtcatgc gctaccgcaa cctgatcgag ggcgaagcat ccgccggttc ctaatgtacg    14100
gagcagatgc tagggcaaat tgccctagca ggggaaaaag gtcgaaaagg tctcttttcct    14160 gtggatagca cgtacattgg gaacccaaag ccgtacattg gaaccggaa cccgtacatt    14220 gggaacccaa agccgtacat tgggaaccgg tcacacatgt aagtgactga tataaaagag    14280
aaaaaaggcg attttccgc ctaaaactct ttaaaactta ttaaaactct taaaacccgc    14340
ctggcctgtg cataactgtc tggccagcgc acagccgaag agctgcaaaa agcgcctacc    14400
cttcggtcgc tgcgctccct acgccccgcc gcttcgcgtc ggcctatcgc ggccgctggc    14460
cgctcaaaaa tggctggcct acggccaggc aatctaccag ggcgcggaca agccgcgccg    14520
tcgccactcg accgccggcg cccacatcaa ggcaccggtg gtatgcctg acgatgcgtg    14580 gagaccgaaa ccttgcgctc gttcgccagc caggacagaa atgcctcgac ttcgctgctg    14640
cccaaggttg ccgggtgacg cacaccgtgg aaacggatga aggcacgaac ccagtggaca    14700
taagcctgtt cggttcgtaa gctgtaatgc aagtagcgta tgcgctcacg caactggtcc    14760
agaaccttga ccgaacgcag cggtggtaac ggcgcagtgg cggttttcat ggcttgttat    14820
gactgttttt ttggggtaca gtctatgcct cgggcatcca agcagcaagc gcgttacgcc    14880
gtgggtcgat gtttgatgtt atggagcagc aacgatgtta cgcagcaggg cagtcgccct    14940
aaaacaaagt taaacatcat gagggaagcg gtgatcgccg aagtatcgac tcaactatca    15000
gaggtagttg gcgtcatcga gcgccatctc gaaccgacgt tgctggccgt acatttgtac    15060
ggctccgcag tggatggcgg cctgaagcca cacagtgata ttgatttgct ggttacggtg    15120
accgtaaggc ttgatgaaac aacgcggcga gctttgatca cgacctttt ggaaacttcg    15180 gcttcccctg gagagagcga gattctccgc gctgtagaag tcaccattgt tgtgcacgac    15240
gacatcattc cgtggcgtta tccagctaag cgcgaactgc aatttggaga atggcagcgc    15300
aatgacattc ttgcaggtat cttcgagcca gccacgatcg acattgatct ggctatcttg    15360
ctgacaaaag caagagaaca tagcgttgcc ttggtaggtc cagcggcgga ggaactcttt    15420
gatccggttc ctgaacagga tctatttgag gcgctaaatg aaaccttaac gctatggaac    15480
tcgccgcccg actgggctgg cgatgagcga aatgtagtgc ttacgttgtc ccgcatttgg    15540
tacagcgcag taaccggcaa aatcgcgccg aaggatgtcg ctgccgactg ggcaatggag    15600
cgcctgccgg cccagtatca gcccgtcata cttgaagcta gacaggctta tcttggacaa    15660
```

```
-continued gaagaagatc gcttggcctc gcgcgcagat cagttggaag aatttgtcca ctacgtgaaa   15720
ggcgagatca ccaaggtagt cggcaaataa tgtctaacaa ttcgttcaag ccgacgccgc   15780
ttcgcggcgc ggcttaactc aagcgttaga tgcactaagc acataattgc tcacagccaa   15840
actatcaggt caagtctgct tttattattt ttaagcgtgc ataataagcc ctacacaaat   15900
tgggagatat atcatgaaag gctggctttt tcttgttatc gcaatagttg gcgaagtaat   15960
cgcaacatag cttgcttggt cgttccgcgt gaacgtcggc tcgattgtac ctgcgttcaa   16020
atactttgcg atcgtgttgc gcgcctgccc ggtgcgtcgg ctgatctcac ggatcgactg   16080
cttctctcgc aacgccatcc gacggatgat gtttaaaagt cccatgtgga tcactccgtt   16140
gccccgtcgc tcaccgtgtt gggggaagg tgcacatggc tcagttctca atggaaatta   16200
tctgcctaac cggctcagtt ctgcgtagaa accaacatgc aagctccacc gggtgcaaag   16260
cggcagcggc ggcaggatat attcaattgt aaatggcttc atgtccggga aatctacatg   16320
gatcagcaat gagtatgatg gtcaatatgg agaaaaagaa agagtaatta ccaattttt    16380 ttcaattcaa aaatgtagat gtccgcagcg ttattataaa atgaaagtac attttgataa   16440
aacgacaaat tacgatccgt cgtatttata ggcgaaagca ataaacaaat tattctaatt   16500
cggaaatctt tatttcgacg tgtctacatt cacgtccaaa tgggggctta gatgagaaac   16560
ttcacgatcg gc                                                       16572
```

US 7,834,243 B2

PROMOTER FOR EPIDERMIS-SPECIFIC, PATHOGEN-INDUCIBLE TRANSGENIC EXPRESSION IN PLANTS

RELATED APPLICATIONS

This application is a national stage application (under 35 U.S.C. 371) of PCT/EP2006/062747 filed May 30, 2006, which claims benefit of German application 102005025656.2 filed Jun. 3, 2005.

SUBMISSION ON COMPACT DISC

The contents of the following submission on compact discs are incorporated herein by reference in its entirety: two copies of the Sequence Listing (COPY 1 and COPY 2) and a computer readable form copy of the Sequence Listing (CRF COPY), all on compact disc, each containing: file name: Sequence List-13477-00010-US, date recorded: Nov. 29, 2007, size: 98 KB.

The present invention relates to promoter regions, under whose control transgenes can be epidermis-specifically and pathogen-inducibly expressed in plants. Furthermore, the invention relates to recombinant nucleic acid molecules comprising said promoter regions, and to transgenic plants and plant cells, which have been transformed by means of said nucleic acid molecules, as well as to methods for their generation. Furthermore, the present invention relates to nucleic acid molecules comprising a promoter according to the present invention, and to nucleic acid sequences or transgenes, which are capable of mediating pathogen resistance, as well as to plants and plant cells transformed by means of said nucleic acid molecules, and to methods for their generation. The invention also relates to the use of the promoter region according to the present invention for assaying pathogen-induced signal transduction pathways in plant cells.

BACKGROUND OF THE INVENTION

Those DNA regions of a gene which are located upstream of the transcription initiation point and by which the initiation point and the initiation frequency of the transcription and thus the expression level and the expression pattern of the controlled gene are determined, are in general referred to as promoters. RNA polymerase and specific transcription factors activating the RNA polymerase bind to the promoters in order to initiate transcription together with the basal transcription complex. The effectiveness of the promoters is often enhanced and regulated by additional DNA sequences, the enhancer sequences, whose position, contrarily to the position of the promoters, is not fixed. These regulatory elements can be located upstream, downstream, or in an intron of the gene to be expressed.

In recombinant DNA technology, promoters are inserted into expression vectors in order to control the expression of a transgene, which is normally not the gene naturally regulated by the promoter. Of substantial significance herein is the specificity of the promoter, which determines at which point in time, in which types of tissues, and at which intensity a gene transferred by means of genetic engineering is expressed.

In plant breeding, recombinant DNA technology is often used for conferring specific advantageous properties to useful plants, which is supposed to lead to a higher yield, for example by means of increased pathogen resistance, or to improved properties of the harvest products. Herein, it is often desirable that the transferred gene be not expressed ubiquitously, but only in those tissues, where the transgenic activity is desired, as the presence of the transgenic product can have a negative effect on normal physiological processes in some tissues. Thus, it could, for example, be shown that the overexpression of an anionic peroxidase under the control of the 35S promoter leads to wilting of transgenic tobacco plants, as less root growth occurs and therefore also less root mass is developed (Lagrimini et al. (1997) Plant Mol Biol. 33 (5), S. 887-895). The overexpression of the spi 2 peroxidase under the control of the ubiquitin promoter leads to reduced epicotyl development and reduced longitudinal growth in comparison with control plants (Elfstrand, M. et al. (2001) Plant Cell Reports 20 (7), S. 596-603). Irrespective of negative effects on physiological processes, it is often supposed to be prevented in resistance breeding that the transgenic product is also present in the harvested plant parts.

Therefore, promoters functioning either tissue-specifically or inducibly have been isolated during the past years. Tissue-specific promoters are, for example, seed-, tuber-, and fruit-specific promoters. The inducible promoters can be activated, for example, by means of chemical induction, light induction, or other stimuli.

It is also desirable to specifically modulate gene expression in the epidermis. The epidermis is the terminal tissue of the above-ground organs of higher plants. As such, the tasks of the epidermis are, on the one hand, to allow water and nutrient exchange of the plant and, on the other hand, to prevent the intrusion of pathogens into the plant. These functions can be specifically modulated by means of altered gene expression in the epidermis with the aid of suitable promoters and genes controlled by the latter.

Epidermis-specific promoters have already been described in dicotyledonous plants. It could thus be shown that the promoter of the CER6-(CUT1-) gene from Arabidopsis, which codes for a condensing enzyme in wax synthesis, can cause the epidermis-specific expression of a β-glucuronidase reporter gene (Hooker et al. (2002) Plant Physiol. 129(4): 1568-1580; Kunst et al. (2000) Biochem. Soc. Trans. 28(6): 651-654).

However, only few suitable epidermis-specific promoters in monocotyledonous plants, which are particularly well suitable for the expression of transgenes in monocotyledons, in particular in poaceae (sweet grasses), have been identified up to now. Recently, a promoter has been described which is composed of the promoter of the GSTA1 gene and the intron of the WIR1a gene and has a constitutive epidermis-specific activity (DE 103 46 611 A1).

As only few suitable promoters for epidermis-specific transgenic expression have been known hitherto, constitutive promoters like the ubiquitin promoter from maize were mostly used in order to express proteins in the epidermis (see, for example, Oldach et al. (2001): Mol Plant Microbe Interact. 14(7): 832-838). However, this can lead to undesired side effects in the transgenic plants due to the presence of the transgenic product in tissues or organs other than the epidermis, as is described above.

It is therefore a problem underlying the present invention to provide means allowing an epidermis-specific and pathogen-inducible gene expression in monocotyledons, preferably in cereal plants.

This problem is solved by providing the embodiments characterized in the patent claims.

DETAILED DESCRIPTION OF THE INVENTION

Figure 1:
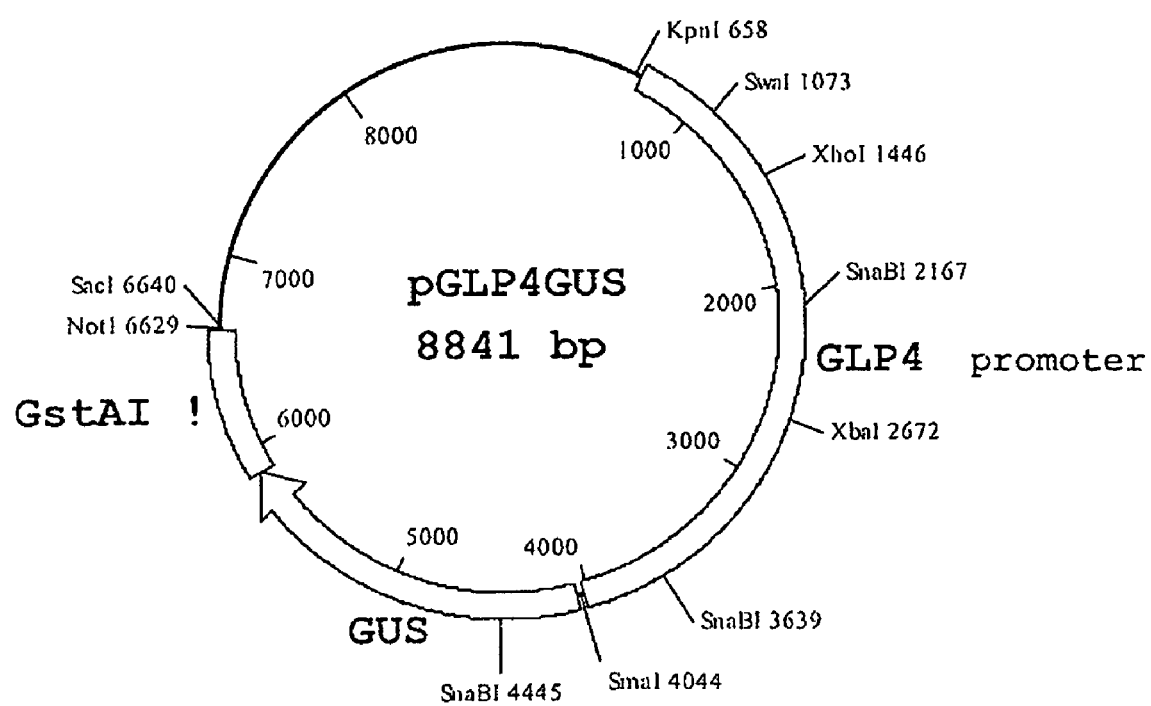
FIG. 1 depicts the vector map of pGLP4GUS.

Thus, the present invention relates to a pathogen-inducible promoter region having a specifity for the plant epidermis, which is selected from the group consisting of
 a) promoter regions comprising the nucleic acid sequence given in SEQ ID NO: 1 or 16,
 b) promoter regions comprising a functional part of the nucleic acid sequence given in SEQ ID NO: 1 or 16, and
 c) promoter regions having a sequence which hybridizes under stringent conditions with the nucleic acid sequence given in SEQ ID NO: 1 or 16.

Preferably, the promoter region according to the present invention comprises an additional sequence which originates from the intron of the WIR1a gene and is selected from the group consisting of
 a) sequences comprising the nucleic acid sequence given in SEQ ID NO: 2, and
 b) sequences hybridizing under stringent conditions with the nucleic acid sequence given in SEQ ID NO: 2.

The additional sequence having SEQ ID NO: 2 can be located both at the 5' and at the 3' end of the nucleic acid sequence given in SEQ ID NO: 1 or 16. Preferably, it is located at the 3' end of the nucleic acid sequence given in SEQ ID NO: 1 or 16. In case the additional sequence is present, the activity of the promoter according to the present invention is enhanced.

Between the first and the second sequence there can be further untranslated sequences having a length of 10 bp to 1,000 bp, preferably of 20 bp to 800 bp, particularly preferably of 30 bp to 500 bp, and most preferably between 40 bp and 300 bp.

Particularly preferably, the promoter region according to the present invention is a promoter region selected from the group consisting of
 a) promoter regions comprising the nucleic acid sequence given in SEQ ID No. 3 or 17;
 b) promoter regions comprising a functional part of the nucleic acid sequence given in SEQ ID No. 3 or 17 or
 c) promoter regions having a sequence, which hybridizes under stringent conditions with the nucleic acid sequence given in SEQ ID No. 3 or 17.

Within the scope of the present invention, a promoter region is understood to be a nucleic acid sequence comprising the regulatory sequences required for the expression of a coding sequence. Regulatory sequences form that part of a gene, which determines the expression of a coding sequence, i.e. in particular the expression level and pattern. The regulatory sequences have at least one sequence motif, where the specific transcription factors and the RNA polymerase bind to, assemble to form the transcription complex, and effectively initiate the transcription of the nucleic acid sequence controlled by the promoter region.

Within the scope of the present invention, the term "epidermis-specific" is understood to denote that a nucleic acid sequence, which is under the control of the promoter region according to the present invention, is expressed in the shoot epidermis of plants. In the sense of the present invention, epidermis-specificity is, in particular, also given, if the promoter region according to the present invention favors the expression of a foreign gene in the epidermis in comparison to other cell types and causes a significantly increased, like at least double, preferably at least 5-fold, particularly preferably at least 10-fold, and most preferably at least 50-fold, expression in the epidermis in comparison to other cell types. The expression level can be determined by means of conventional in situ detection techniques.

The term "plant epidermis" is known to the person skilled in the art. Complementary information can be found in any book on plant anatomy or plant physiology, like, for example, in Strasburger, Lehrbuch der Botanik, 35. edition 2002, Spektrum Akademischer Verlag.

Within the scope of the present invention, the term "pathogen-inducible" is understood to denote that the expression of a nucleic acid sequence, which is under the control of the promoter region according to the present invention, is induced by contacting the plant or the plant cell with a pathogen. In particular, the pathogen inducibility in the sense of the present invention is also given in case the promoter region according to the present invention significantly increases, like at least double, preferably at least 5-fold, particularly preferably at least 10-fold, and most preferably 50-fold, the expression of a foreign gene in the plant/plant cell in comparison to plants/plant cells which are not in contact with a pathogen. The expression level can be determined by means of conventional in situ detection techniques.

In principle, the pathogens enhancing the activity of the promoter region according to the present invention can be any pathogens; preferably they are *Blumeria graminis*, *Rynchosporium secalis* or *Cochliobolus sativus*.

The present invention also relates to promoter regions having the functional parts of the sequence according to the present invention and causing in plants an epidermis-specific and pathogen-inducible expression of a coding nucleic acid sequence that is controlled by them.

In this context, a "functional part" is understood to denote sequences, which the transcription complex, despite a slightly deviating nucleic acid sequence, can still bind to and cause epidermis-specific and pathogen-inducible expression. Functional parts of a promoter sequence also comprise such promoter variants, whose promoter activity is lessened or enhanced in comparison to the wild-type.

In particular, a functional part is, of course, also understood to denote natural or artificial variants of the sequence of the promoter region given in SEQ ID NO 1, 3, 16 or 17. Mutations comprise substitutions, additions, deletions, substitutions, and/or insertions of one or more nucleotide residue/s. Within the scope of the present invention, functional parts of the promoter regions comprise naturally occurring variants of SEQ ID NO 1, 3, 16 or 17 as well as artificial nucleotide sequences, for example obtained by means of chemical synthesis. The "functional part" has an epidermis-specific and pathogen-inducible promoter activity of 10%, 20%, 30% or 40%, preferably 50%, 60% or 70%, particularly preferably 80%, 90% or 100% and most preferably of 120%, 150% or 200% or more of the activity of the wild type promoter sequence.

By means of deletion experiments it was found that the sequence motifs responsible for pathogen-inducibility are located all over the entire promoter sequence according to SEQ ID NO: 1, wherein it is assumed that there are in particular enhancer motifs located in the 5' region.

The promoter activity of variants of the promoter region can be measured with the aid of reporter genes whose coding sequence is under the control of the promoter region to be assayed. Suitable reporter genes are, for example, the β-glucuronidase (GUS) gene from *E. coli*, a fluorescence gene like, for example, the Green Fluorescence Protein (GFP) gene from *Aequoria victoria*, the luziferase gene from *Photinus pyralis* or the β-galaktosidase (lacZ) gene from *E. coli*. Absolute promoter activity is determined by means of comparison with a wild type plant. Tissue or cell specifity can easily be determined by means of comparing the expression rates of the above-mentioned reporter genes in the respective tissues or cells. Inducibility can easily be determined by means of comparing the expression rates of the above-mentioned reporter genes in treated and untreated plants.

The present invention also relates to promoter regions having a nucleic acid sequence hybridizing under stringent conditions with the nucleic acid sequences given in SEQ ID NO: 1, 2, 3, 16 or 17. In the context of the present invention, the term "hybridization under stringent conditions" is understood to denote that the hybridization in vitro is performed under conditions that are sufficiently stringent to ensure a specific hybridization. Such stringent hybridization conditions are known to the person skilled in the art and can be taken from the literature (Sambrook et al. (2001), Molecular Cloning: A Laboratory Manual, $3^{rd}$ edition, Cold Spring Harbor Laboratory Press, Cold Spring Harbor, N.Y.).

In general, "specifically hybridize" means that a molecule preferentially binds to a specific nucleotide sequence under stringent conditions, if said sequence is present in the form of a complex mixture of (for example total) DNA or RNA. The term "stringent conditions" generally denotes conditions, under which a nucleic acid sequence will preferentially bind to its target sequence and to a considerably smaller extent or not at all to other sequences. Stringent conditions are partially sequence-dependent and will be different under different circumstances. Longer sequences specifically hybridize at higher temperatures. In general, stringent conditions are selected in such a way that the temperature lies about 5° C. below the thermal melting point $(T_m)$ for the specific sequence at a defined ionic strength and a defined pH value. $T_m$ is the temperature (under defined ionic strength, pH value, and nucleic acid concentration), at which 50% of the molecules complementary to the target sequence hybridize to the target sequence in a state of equilibrium. Typically, stringent conditions are conditions, under which the salt concentration is at least about 0.01 to 1.0 M sodium ion concentration (or another salt) at a pH value of between 7.0 and 8.3 and the temperature is at least 30° C. for short molecules (i.e. for example 10 to 50 nucleotides). In addition, stringent conditions can be achieved by means of adding destabilizing agents, like for example formamide.

Suitable stringent hybridization conditions are, for example, also described in Sambrook et al., vide supra. Thus, hybridization can, for example, occur under the following conditions:

hybridization buffer: 2×SSC, 10×Denhardt's solution (Ficoll 400+PEG+BSA; ratio 1:1:1), 0.1% SDS, 5 mM EDTA, 50 mM $Na_2HPO_4$, 250 µg/ml herring sperm DNA; 50 µg/ml tRNA or 0.25 M sodium phosphate buffer pH 7.2, 1 mM EDTA, 7% SDS at a hybridization temperature of 65° C. to 68° C.

washing buffer: 0.2×SSC, 0.1% SDS at a washing temperature of 65° C. to 68° C.

Preferably, such promoter variants have a sequence identity of at least 50%, preferably at least 70%, particularly preferably at least 90%, and most preferably at least 95% to the promoter sequence given in SEQ ID NO 1, 3, 16 or 17 or parts thereof, in relation to the total DNA sequence shown in SEQ ID NO 1, 3, 16 or 17.

Preferably, the sequence identity of such promoter sequences is determined by means of comparison with the nucleic acid sequence given in SEQ ID NO 1, 3, 16 or 17. In case two nucleic acid sequences of different lengths are compared to each other, the sequence identity preferably relates to the percentage of the nucleotide residues of the shorter sequence, which are identical to the corresponding nucleotide residues of the longer sequence.

Sequence identities are conventionally determined via different alignment programs, like for example CLUSTAL. In general, the person skilled in the art has at his disposal suitable algorithms for determining the sequence identity, for example also the program which is accessible under at the ncbi.nlm.nih.gov/BLAST website (for example the link "standard nucleotide-nucleotide BLAST [blastn]").

The present invention also relates to chimeric genes of the promoter region according to the present invention and of a coding sequence, whose expression, which is naturally not regulated by the promoter region according to the present invention, in the chimeric gene is regulated by the promoter region according to the present invention, in operative linkage as well as to recombinant nucleic acid molecules containing said chimeric gene.

The term "nucleic acid sequence, whose expression is regulated by the promoter region according to the present invention" means that the expression of the nucleic acid sequence under the control of the promoter region according to the present invention in those cells and under those conditions, where the promoter region is active, can be increased by at least the factor five, preferably at least the factor 10, and particularly preferably at least the factor 50 in comparison to wild-type cells.

The nucleic acid sequence, whose expression is regulated by the nucleic acid sequence according to the present invention, can be the coding region of a transgene, for example a resistance gene, whose gene product is desired in the epidermis. By means of expression of the transgene, the content of the gene product encoded by it can be increased by at least the factor 2, preferably by at least the factor 5, particularly preferably by at least the factor 10, and most preferably by at least the factor 50.

However, the promoter region according to the present invention can also be used in RNAi constructs for RNA interference in order to achieve epidermis-specific and pathogen-inducible silencing of specific genes, whose gene products are supposed to be present in the epidermis to a smaller extent than usual or not at all and whose expression is not supposed to be induced by affection of the plant with a pathogen. Of course, the latter can also be achieved by means of classic antisense or co-suppression constructs with the use of the promoter regions according to the present invention. By means of the silencing constructs, the expression of the endogenous gene is decreased by at least 50%, preferably by at least 70%, particularly preferably by at least 90%, and most preferably by at least 95%.

In a construct which is supposed to be used for RNA interference, there are usually palindromic DNA sequences, which form double-stranded RNA subsequent to transcription. By means of the dicer enzyme, said double-stranded RNA is processed to form shorter RNA pieces, which bind to an endogenous RNA and cause its degradation with the aid of the RISC (RNA-induced silencing complex) (Hannon (2002) Nature, 418: 244-251).

The effect of the gene silencing constructs on the expression of the endogenous gene can be detected by means of conventional molecular biological methods, which are known to the person skilled in the art. Thus, Northern blot and RT-PCR methods are available for examining the RNA level; the protein can be detected by means of Western blot analyses, immunofluorescences, or, provided that the protein is an enzyme, by means of enzyme assays.

Within the scope of the present invention, the term "transgene" summarizes those genes, whose gene products are supposed to be provided in the epidermis in a pathogen-inducible manner or are supposed to be suppressed in gene silencing.

Preferably, the nucleic acid sequence, whose expression is under the control of the promoter according to the present invention, is a nucleic acid sequence which mediates pathogen resistance, as the epidermis is the first barrier which has to be surmounted by a pathogen when intruding into the plant.

In a chimeric gene or in a recombinant expression vector, "operatively linked to" is understood to denote that the nucleotide sequence of interest is bound to the regulatory sequence/s in such a way as to allow the expression of the nucleotide sequence and that both sequences are bound to each other in such a way as to fulfill the predicted function assigned to said sequence.

Within the scope of the present invention, the term "recombinant nucleic acid molecule" is understood to denote a vector, which contains a chimeric gene according to the present invention or a promoter region according to the present invention and which can cause the promoter-dependent expression of the nucleic acid sequence, which is under the control of the promoter region according to the present invention, in plant cells and plants. In a preferred embodiment, a recombinant nucleic acid molecule according to the present invention additionally contains transcriptional termination sequences. Herein, "transcriptional termination sequences" are understood to denote DNA sequences, which are located at the downstream end of a coding sequence and which cause the RNA polymerase to terminate the transcription.

Furthermore, the invention relates to methods for generating transgenic plants with epidermis-specific and pathogen-inducible expression of a nucleic acid sequence, which is regulated by the promoter region according to the present invention, comprising the following steps:

a) generating a recombinant nucleic acid molecule, in which the promoter region according to the present invention is present in operative linkage with a coding sequence, b) transferring the nucleic acid molecule from a) to plant cells and c) regenerating entirely transformed plants and, if desired, propagating the plants.

For preparing the introduction of foreign genes into higher plants and their cells, respectively, a large number of cloning vectors containing a replication signal for *E. coli* and a marker gene for selecting transformed bacteria cells are available. Examples for such vectors are pBR322, pUC series, M13mp series, pACYC184, and so on. The chimeric gene can be introduced into the vector at a suitable restriction interface. The plasmid obtained is then used for transforming *E. coli* cells. Transformed *E. coli* cells are cultivated in a suitable medium and are subsequently harvested and lysed and the plasmid is re-obtained. Restriction analyses, gel electrophoreses, and further biochemical-molecular biological methods are generally used as analysis methods for characterizing the plasmid DNA obtained. Subsequent to each manipulation, the plasmid DNA can be cleaved and DNA fragments obtained therefrom can be linked with other DNA sequences.

As has already been mentioned, a variety of techniques for introducing DNA into a plant host cell are available, wherein the person skilled in the art is capable of determining without any difficulties the method suitable in each case. Said techniques comprise transformation of plant cells with T-DNA using *Agrobacterium tumefaciens* or *Agrobacterium rhizogenes* as transformation medium, fusion of protoplasts, injection, electroporation, direct gene transfer of isolated DNA into protoplasts, introduction of DNA by means of biolistic methods as well as further possibilities, which have been well established for several years now and which belong to the standard repertoire of the person skilled in the art of plant molecular biology and plant biotechnology, respectively. The biolistic gene transfer method is, in particular, used in monocotyledonous plants. Here, the person skilled in the art can find useful information on the conduction, for example in Vasil et al. (1992) Bio/Technology, 10: 667-674; Vasil et al. (1993) Bio/Technology, 11: 1153-1158; Nehra et al. (1994) Plant J. 5: 285-297; Becker et al. (1994) Plant J., 5: 299-307; Altpeter et al. (1996) Plant Cell Reports 16: 12-17; Ortiz et al. (1996) Plant Cell Reports 15: 877-81; Rasco-Gaunt et al. (2001) J. Exp. Bot. 52: 865-874.

In the case of injection and electroporation of DNA into plant cells, no specific demands per se are made on the plasmids used. This also applies to direct gene transfer. Simple plasmids, like for example pUC derivatives, can be used.

However, if whole plants are supposed to be regenerated from cells transformed in this manner, the presence of a selectable marker gene is recommendable. Standard selection markers are known to the person skilled in the art and selecting a suitable marker does not pose a problem.

According to the method of introducing the desired genes into the plant cell, further DNA sequences may be required. If, for example, the Ti or Ri plasmid is used for transforming the plant cell, at least the right border, though often the right and left borders, of the T-DNA contained in the Ti or Ri plasmid, have to be joined with the genes, which are supposed to be introduced, in order to form a flanking region. In case agrobacteria are used for transformation, the DNA which is supposed to be introduced has to be cloned into specific plasmids, actually either into an intermediate or into a binary vector. Due to sequences which are homologous to sequences in the T-DNA the intermediate vectors can be integrated into the Ti or Ri plasmid of the agrobacteria by means of homologous recombination. Said plasmid also contains the vir region that is necessary for the transfer of the T-DNA. However, intermediate vectors cannot replicate in agrobacteria. By means of a helper plasmid, the intermediate vector can be transferred to *Agrobacterium tumefaciens* (conjugation). Binary vectors, however, can replicate in both *E. coli* and in agrobacteria. They contain a selection marker gene and a linker or polylinker, which are framed by the right and left T-DNA border region. They can be transformed directly into the agrobacteria. The agrobacterium serving as a host cell should contain a plasmid carrying the chimeric gene within the T-DNA, which is transferred into the plant cell. Additional T-DNA can be present. The agrobacterium transformed in such a way is used for the transformation of plant cells. The use of T-DNA for the transformation of plant cells has been intensely examined and sufficiently described in commonly known survey articles and manuals on plant transformation.

In the case of monocotyledonous plants, altered protocols must be applied for effective agrobacterium-mediated gene transfer, as they are, for example, described in Cheng et al.

(1997) Plant Physiol. 115: 971-980; Khanna and Daggard (2003) Plant Cell Reports 21: 429-436; Wu et al. (2003) Plant Cell Reports 21: 659-668; Hu et al. (2003) Plant Cell Reports 21: 1010-1019. For the transfer of the DNA into the plant cell, plant explants can advisably be cultivated with *Agrobacterium tumefaciens* or *Agrobacterium rhizogenes*. Whole plants can then be regenerated from the infected plant material (e.g. pieces of leaves, segments of stems, roots, but also protoplasts or suspension-cultivated plant cells) in a suitable medium, which may contain antibiotics or biocides for the selection of transformed cells.

Once the DNA introduced is integrated in the genome of the plant cell, it is normally stable there and is also maintained in the offspring of the originally transformed cell. The DNA introduced normally contains a selection marker, which mediates to the transformed plant cells resistance against a biocide or an antibiotic like kanamycin, G 418, bleomycin, hygromycin, methotrexate, glyphosate, streptomycin, sulfonylurea, gentamycin or phosphinotricin and others. The individually selected marker should therefore allow the selection of transformed cells against cells lacking the DNA introduced. To this end, alternative markers like nutritive markers or screening markers (like GFP, green fluorescent protein), are also suitable. Selection markers can, of course, also be entirely omitted, which, however, is accompanied by a comparatively high screening necessity. In case marker-free transgenic plants are desired, the person skilled in the art also has at his disposal strategies, which allow removing the marker gene later on, for example co-transformation or sequence-specific recombinases.

Regeneration of the transgenic plants from transgenic plant cells is conducted according to conventional regeneration methods using known nutritive media. The plants obtained in this manner can then be examined by means of conventional methods, including molecular biological methods like PCR, blot analyses for presence and tissue specificity of the nucleic acid sequence introduced, whose expression is controlled by the promoter according to the present invention, or for RNAs and proteins influenced by said nucleic acid sequence.

Furthermore, the invention relates to transgenic plants containing a nucleic acid sequence regulated by the promoter region according to the present invention and epidermis-specifically and pathogen-inducibly expressing said nucleic acid sequence.

Preferably, the plants according to the present invention are monocotyledons, in particular cereal plants like rye, maize, and oats, particularly preferably wheat or barley, as well as transgenic parts of said plants and their transgenic propagation material, like protoplasts, plant cells, calli, seeds, tubers or cuttings, as well as the transgenic offspring of said plants. However, the promoter region according to the present invention can also be used in other poaceae (sweet grasses), like for example feed grasses, for generating corresponding plants exhibiting epidermis-specific and pathogen-inducible expression of transgenes.

Under the control of the epidermis-specific promoter according to the present invention pathogen resistance genes are preferably expressed under the control of the promoter according to the present invention.

Bacteria, viruses, animal pathogens and fungi, which infect plants and thereby negatively influence the metabolism of the plant, are, inter alia, referred to as plant pathogens. Preferably, a resistance gene under the control of the promoter sequence according to the present invention mediates resistance to fungal pathogens like for example mildew. It must be assumed, however, that the genes expressed under the control of the sequence according to the present invention also effect a resistance to further pathogens.

Fungal pathogens or fungoid pathogens (like for example chromista) preferably originate from the group consisting of Plasmodiophoramycota, Oomycota, Ascomycota, Chytridiomycetes, Zygomycetes, Basidiomycota and Deuteromycetes (fungi imperfecti). In an exemplary, but not restricting manner, the fungal pathogens given in Table 1 and the diseases associated therewith are to be mentioned.

TABLE 1

| Fungal plant diseases | |
|---|---|
| Disease | Pathogen |
| Brown rust | *Puccinia recondita* |
| Yellow rust | *P. striiformis* |
| Powdery mildew | *Erysiphe graminis/Blumeria graminis* |
| Glume blotch | *Septoria nodorum* |
| Blotch | *Septoria tritici* |
| Head fusarioses | *Fusarium* spp. |
| Stem break | *Pseudocercosporella herpotrichoides* |
| Loose smut (*Ustilago nuda*) | *Ustilago* spp. |
| Common bunt | *Tilletia caries* |
| Take-all patch | *Gaeumannomyces graminis* |
| Anthracnose leaf blight | *Colletotrichum graminicola* (telomorphic: |
| Anthracnose stalk rot | *Glomerella graminicola Politis*); *Glomerella tucumanensis* (anamorphic: *Glomerella falcatum* Went) |
| *Aspergillus* ear and kernel rot | *Aspergillus flavus* |
| Banded leaf and sheath spot ("root killer") | *Rhizoctonia solani* Kuhn = *Rhizoctonia microsclerotia* J. Matz (telomorphic: *Thanatephorus cucumeris*) |
| Black bundle disease | *Acremonium strictum* W. Gams = *Cephalosporium acremonium* Auct. non Corda |
| Black kernel rot | *Lasiodiplodia theobromae* = *Botryodiplodia theobromae* |
| Borde blanco | *Marasmiellus* sp. |
| Brown spot (black spot, stalk rot) | *Physoderma maydis* |
| *Cephalosporium* kernel rot | *Acremonium strictum* = *Cephalosporium acremonium* |

TABLE 1-continued

| Fungal plant diseases | |
|---|---|
| Disease | Pathogen |
| Charcoal rot | *Macrophomina phaseolina* |
| *Corticium* ear rot | *Thanatephorus cucumeris* = *Corticium sasakii* |
| *Curvularia* leaf spot | *Curvularia clavata, C. eragrostidis,* = *C. maculans* (telomorphic: *Cochliobolus eragrostidis*), *Curvularia inaequalis, C. intermedia* (telomorphic: *Cochliobolus intermedius*), *Curvularia lunata* (telomorphic: *Cochliobolus lunatus*), *Curvularia pallescens* (telomorphic: *Cochliobolus pallescens*), *Curvularia senegalensis, C. tuberculata* (telomorphic: *Cochliobolus tuberculatus*) |
| *Didymella* leaf spot | *Didymella exitalis* |
| *Diplodia* ear rot and stalk rot | *Diplodia frumenti* (telomorphic: *Botryosphaeria festucae*) |
| *Diplodia* ear rot, stalk rot, seed rot and seedling blight | *Diplodia maydis* = *Stenocarpella maydis* |
| *Diplodia* leaf spot or streak | *Stenocarpella macrospora* = *Diplodia macrospora* |
| Brown stripe downy mildew | *Sclerophthora rayssiae* var. *zeae* |
| Crazy top downy mildew | *Sclerophthora macrospora* = *Sclerospora macrospora* |
| Green ear downy mildew (*graminicola* downy mildew) | *Sclerospora graminicola* |
| Java downy mildew | *Peronosclerospora maydis* = *Sclerospora maydis* |
| Philippine downy mildew | *Peronosclerospora philippinensis* = *Sclerospora philippinensis* |
| *Sorghum* downy mildew | *Peronosclerospora sorghi* = *Sclerospora sorghi* |
| Spontaneum downy mildew | *Peronosclerospora spontanea* = *Sclerospora spontanea* |
| Sugarcane downy mildew | *Peronosclerospora sacchari* = *Sclerospora sacchari* |
| Dry ear rot (cob, kernel and stalk rot) | *Nigrospora oryzae* (telomorphic: *Khuskia oryzae*) |
| Ear rots, minor | *Alternaria alternata* = *A. tenuis, Aspergillus glaucus, A. niger, Aspergillus* spp., *Botrytis cinerea* (telomorphic: *Botryotinia fuckeliana*), *Cunninghamella* sp., *Curvularia pallescens, Doratomyces stemonitis* = *Cephalotrichum stemonitis, Fusarium culmorum, Gonatobotrys simplex, Pithomyces maydicus, Rhizopus microsporus Tiegh., R. stolonifer* = *R. nigricans, Scopulariopsis brumptii* |
| Ergot (horse's tooth) | *Claviceps gigantea* (anamorphic: *Sphacelia* sp.) |
| Eyespot | *Aureobasidium zeae* = *Kabatiella zeae* |
| *Fusarium* ear and stalk rot | *Fusarium subglutinans* = *F. moniliforme* var. *subglutinans* |
| *Fusarium* kernel, root and stalk rot, seed rot and seedling blight | *Fusarium moniliforme* (telomorphic: *Gibberella fujikuroi*) |
| *Fusarium* stalk rot, seedling root rot | *Fusarium avenaceum* (telomorphic: *Gibberella avenacea*) |
| *Gibberella* ear and stalk rot | *Gibberella zeae* (anamorphic: *Fusarium graminearum*) |
| Gray ear rot | *Botryosphaeria zeae* = *Physalospora zeae* (anamorphic: *Macrophorma zeae*) |
| Gray leaf spot (*Cercospora* leaf spot) | *Cercospora sorghi* = *C. sorghi* var. *maydis, C. zeae-maydis* |
| *Helminthosporium* root rot | *Exserohilum pedicellatum* = *Helminthosporium pedicellatum* (telomorphic: *Setosphaeria pedicellata*) |
| *Hormodendrum* ear rot (*Cladosporium* rot) | *Cladosporium cladosporioides* = *Hormodendrum cladosporioides, C. herbarum* (telomorphic: *Mycosphaerella tassiana*) |
| *Hyalothyridium* leaf spot | *Hyalothyridium maydis* |
| Late wilt | *Cephalosporium maydis* |

TABLE 1-continued

| Fungal plant diseases | |
|---|---|
| Disease | Pathogen |
| Leaf spots, minor | *Alternaria alternata, Ascochyta maydis, A. tritici, A. zeicola, Bipolaris victoriae = Helminthosporium vicoriae* (telomorphic: *Cochliobolus victoriae*), *C. sativus* (anamorphic: *Bipolaris sorokiniana = H. sorokinianum = H. sativum*), *Epicoccum nigrum, Exserohilum prolatum = Drechslera prolata* (telomorphic: *Setosphaeria prolata*) *Graphium penicillioides, Leptosphaeria maydis, Leptothyrium zeae, Ophiosphaerella herpotricha*, (anamorphic: *Scolecosporiella* sp.), *Paraphaeosphaeria michotii, Phoma* sp., *Septoria zeae, S. zeicola, S. zeina* |
| Northern corn leaf blight (white blast, crown stalk rot, stripe) | *Setosphaeria turcica* (anamorphic: *Exserohilum turcicum = Helminthosporium turcicum*) |
| Northern corn leaf spot *Helminthosporium* ear rot (race 1) | *Cochliobolus carbonum* (anamorphic: *Bipolaris zeicola = Helminthosporium carbonum*) |
| *Penicillium* ear rot (blue eye, blue mold) | *Penicillium* spp., *P. chrysogenum, P. expansum, P. oxalicum* |
| *Phaeocytostroma* stalk rot and root rot | *Phaeocytostroma ambiguum = Phaeocytosporella zeae* |
| *Phaeosphaeria* leaf spot | *Phaeosphaeria maydis = Sphaerulina maydis* |
| *Physalospora* ear rot (*Botryosphaeria* ear rot) | *Botryosphaeria festucae = Physalospora zeicola* (anamorphic: *Diplodia frumenti*) |
| Purple leaf sheath | Hemiparasitic bacteria and *fungi* |
| *Pyrenochaeta* stalk rot and root rot | *Phoma terrestris = Pyrenochaeta terrestris* |
| *Pythium* root rot | *Pythium* spp., *P. arrhenomanes, P. graminicola* |
| *Pythium* stalk rot | *Pythium aphanidermatum = P. butleri L.* |
| Red kernel disease (ear mold, leaf and seed rot) | *Epicoccum nigrum* |
| *Rhizoctonia* ear rot (*sclerotial* rot) | *Rhizoctonia zeae* (telomorphic: *Waitea circinata*) |
| *Rhizoctonia* root rot and stalk rot | *Rhizoctonia solani, Rhizoctonia zeae* |
| Root rots, minor | *Alternaria alternata, Cercospora sorghi, Dictochaeta fertilis, Fusarium acuminatum* (telomorphic: *Gibberella acuminata*), *F. equiseti* (telomorphic: *G. intricans*), *F. oxysporum, F. pallidoroseum, F. poae, F. roseum, G. cyanogena* (anamorphic: *F. sulphureum*), *Microdochium bolleyi, Mucor* sp., *Periconia circinata, Phytophthora cactorum, P. drechsleri, P. nicotianae* var. *parasitica, Rhizopus arrhizus* |
| *Rostratum* leaf spot (*Helminthosporium* leaf disease, ear and stalk rot) | *Setosphaeria rostrata* (anamorphic: *Exserohilum rostratum = Helminthosporium rostratum*) |
| Rust, common corn | *Puccinia sorghi* |
| Rust, southern corn | *Puccinia polysora* |
| Rust, tropical corn | *Physopella pallescens, P. zeae = Angiopsora zeae* |
| *Sclerotium* ear rot (southern blight) | *Sclerotium rolfsii* Sacc. (telomorphic: *Athelia rolfsii*) |
| Seed rot-seedling blight | *Bipolaris sorokiniana, B. zeicola = Helminthosporium carbonum, Diplodia maydis, Exserohilum pedicillatum, Exserohilum turcicum = Helminthosporium turcicum, Fusarium avenaceum, F. culmorum, F. moniliforme, Gibberella zeae* (anamorphic: *F. graminearum*), *Macrophomina phaseolina, Penicillium* spp., *Phomopsis* sp., *Pythium* spp., *Rhizoctonia solani, R. zeae, Sclerotium rolfsii, Spicaria* sp. |
| *Selenophoma* leaf spot | *Selenophoma* sp. |
| Sheath rot | *Gaeumannomyces graminis* |
| Shuck rot | *Myrothecium gramineum* |
| Silage mold | *Monascus purpureus, M ruber* |
| Smut, common | *Ustilago zeae = U. maydis* |
| Smut, false | *Ustilaginoidea virens* |
| Smut, head | *Sphacelotheca reiliana = Sporisorium holcisorghi* |
| Southern corn leaf blight and stalk rot | *Cochliobolus heterostrophus* (anamorphic: *Bipolaris maydis = Helminthosporium maydis*) |
| Southern leaf spot | *Stenocarpella macrospora = Diplodia macrospora* |
| Stalk rots, minor | *Cercospora sorghi, Fusarium episphaeria, F. merismoides, F. oxysporum Schlechtend, F. poae, F. roseum, F. solani* (telomorphic: *Nectria haematococca*), *F. tricinctum, Mariannaea elegans, Mucor* sp., *Rhopographus zeae, Spicaria* sp. |

TABLE 1-continued

Fungal plant diseases

| Disease | Pathogen |
|---|---|
| Storage rots | *Aspergillus* spp., *Penicillium* spp. and other *fungi* |
| Tar spot | *Phyllachora maydis* |
| *Trichoderma* ear rot and root rot | *Trichoderma viride* = *T. lignorum* (telomorphic: *Hypocrea* sp.) |
| White ear rot, root and stalk rot | *Stenocarpella maydis* = *Diplodia zeae* |
| Yellow leaf blight | *Ascochyta ischaemi*, *Phyllosticta maydis* (telomorphic: *Mycosphaerella zeae-maydis*) |
| Zonate leaf spot | *Gloeocercospora sorghi* |

Particularly preferable is a resistance to

Plasmodiophoromycetes like *Plasmodiophora brassicae* (clubroot of crucifers), *Spongospora subterranea* (powdery scab of potato tubers), *Polymyxa graminis* (root disease of cereals and grasses)

Oomycetes like *Bremia lactucae* (downy mildew of lettuce), *Peronospora* (downy mildew) in snapdragon (*P. antirrhini*), onion (*P. destructor*), spinach (*P. effusa*), soy bean (*P. manchurica*), tobacco (blue mold; *P. tabacina*) alfalfa and clover (*P. trifolium*), *Pseudoperonospora humuli* (downy mildew of hop), *Plasmopara* (downy mildew of grapes) (*P. viticola*) and sunflower (*P. halstedii*), *Sclerophtohra macrospora* (downy mildew of cereals and grasses), *Pythium* (seed rot, seedling damping-off, and root rot and all types of plants, for example black root disease of beet caused by *P. debaryanum*), *Phytophthora infestans* (potato light blight, tomato late blight, etc.), *Albugo* spec. (white rust on cruciferous plants);

Ascomycetes like *Microdochium nivale* (snow mold of rye and wheat), *Fusarium graminearum, Fusarium culmorum* (head blight, in particular of wheat), *Fusarium oxysporum* (fusarium wilt of tomato), *Blumeria graminis* (powdery mildew of barley (f.sp. *hordei*) and wheat (f.sp. *tritici*)), *Erysiphe pisi* (pea mildew), *Nectria galligena* (Nectria canker of fruit trees), *Unicnula necator* (grapevine powdery mildew), *Pseudopeziza tracheiphila* (grapevine red fire disease), *Claviceps purpurea* (ergot in, for example, rye and grasses), *Gaeumannomyces graminis* (black leg disease of wheat, rye and other grasses), *Magnaporthe grisea* (rice blast disease), *Pyrenophora graminea* (leaf stripe disease of barley), *Pyrenophora teres* (leaf stripe disease of barley), *Pyrenophora tritici-repentis* (tan spot disease (Septoria leaf spot) of wheat), *Venturia inaequalis* (apple scab disease), *Sclerotinia sclerotium* (white mold, stem canker of rape), *Pseudopeziza medicaginis* (leaf spot diseases of lucerne, white and red clover);

Basidiomycetes like *Typhula incarnata* (typhula snow mold of barley, rye, and wheat), *Ustilago maydis* (corn smut), *Ustilago nuda* (loose smut of barley), *Ustilago tritici* (loose smut of wheat and spelt), *Ustilago avenae* (loose smut of oat), *Rhizoctonia solani* (root killer of potatoes), *Sphacelotheca* spp. (head smut of sorghum), *Melampsora lini* (rust of flax), *Puccinia graminis* (stem rust of wheat, barley, rye, oat), *Puccinia recondita* (brown rust of wheat), *Puccinia dispersa* (brown rust of rye), *Puccinia hordei* (brown rust of barley), *Puccinia coronata* (crown rust of oat), *Puccinia striiformis* (yellow rust of wheat, barley, rye, and numerous grasses), *Uromyces appendiculatus* (bean rust), *Sclerotium rolfsii* (root and stem rots of many plants);

Deuteromycetes (Fungi imperfecti) like *Septoria nodorum* (glume blotch) of wheat (*Septoria tritici*), *Pseudocercosporella herpotrichoides* (stem break disease in wheat, barley, and rye), *Rynchosporium secalis* (scald disease in rye and barley), *Alternaria solani* (early blight of potato and tomato), *Phoma betae* (black rot of beet), *Cercospora beticola* (Cercospora leaf spot of beet), *Alternaria brassicae* (dark leaf spot of rape, cabbage and other cruciferous plants), *Verticillium dahliae* (Verticillium wilt and stalk rot of rape), *Colletotrichum lindemuthianum* (bean anthracnose), *Phoma lingam*— phoma stem canker (black leg disease of cabbage; crown and stem canker of rape), *Botrytis cinerea* (gray mold diseases of grapevine, strawberry, tomato, hop, etc.).

is effected.

Most preferably, the plants produced by means of the method according to the present invention are resistant to *Phytophthora infestans* (late blight of tomato, root and foot rot of tomato, etc.), *Microdochium nivale* (formerly *Fusarium nivale*; snow mold of rye and wheat), *Fusarium graminearum, Fusarium culmorum* (head blight of wheat), *Fusarium oxysporum* (*Fusarium* wilt of tomato), *Blumeria graminis* (powdery mildew of barley (f. sp. *hordei*) and wheat (f. sp. *tritici*)), *Magnaporthe grisea* (rice blast disease), *Sclerotinia sclerotium* (white mold, stem canker of rape), *Septoria nodorum* and *Septoria tritici* (glume blotch of wheat), *Alternaria brassicae* (dark leaf spot of rape, cabbage and other cruciferous plants), *Phoma lingam* (phoma stem canker, black leg disease of cabbage; crown and stem canker of rape).

In an exemplary, yet not limiting manner the pathogens listed in Table 2 as well as the diseases associated therewith are to be mentioned as bacterial pathogens.

TABLE 2

Bacterial diseases

| Disease | Pathogen |
|---|---|
| Bacterial leaf blight and stalk rot | *Pseudomonas avenae* subsp. *avenae* |
| Bacterial leaf spot | *Xanthomonas campestris pv. holcicola* |
| Bacterial stalk rot | *Enterobacter dissolvens* = *Erwinia dissolvens* |

TABLE 2-continued

Bacterial diseases

| Disease | Pathogen |
| --- | --- |
| Bacterial stalk and top rot | *Erwinia carotovora* subsp. *carotovora*, *Erwinia chrysanthemi* pv. *zeae* |
| Bacterial stripe | *Pseudomonas andropogonis* |
| Chocolate spot | *Pseudomonas syringae* pv. *coronafaciens* |
| Goss's bacterial wilt and blight (leaf freckles and wilt) | *Clavibacter michiganensis* subsp. *nebraskensis* = *Corynebacterium michiganense* pv.*andnebraskense* |
| Holcus spot | *Pseudomonas syringae* pv. *syringae* |
| Purple leaf sheath | Hemiparasitic bacteria |
| Seed rot-seedling blight | *Bacillus subtilis* |
| Stewart's disease (bacterial wilt) | *Pantoea stewartii* = *Erwinia stewartii* |
| Corn stunt (achapparramiento, maize stunt, Mesa Central or Rio Grande maize stunt) | *Spiroplasma kunkelii* |

Particularly preferably, the transgenic plants produced according to the present invention are resistant to the following pathogenic bacteria:

*Corynebacterium sepedonicum* (bacterial ring rot of potato), *Erwinia carotovora* (black leg rot of potato), *Erwinia amylovora* (fire blight of pear, apple, quince), *Streptomyces scabies* (common scab of potato), *Pseudomonas syringae* pv. *tabaci* (wild fire disease of tobacco), *Pseudomonas syringae* pv. *phaseolicola* (halo blight disease of dwarf bean), *Pseudomonas syringae* pv. *tomato* (bacterial speck of tomato), *Xanthomonas campestris* pv. *malvacearum* (angular leaf spot of cotton) and *Xanthomonas campestris* pv. *oryzae* (bacterial blight of rice and other grasses).

The term "viral pathogens" includes all plant viruses, like for example tobacco or cucumber mosaic virus, ringspot virus, necrosis virus, maize dwarf mosaic virus, etc.

In an exemplary, yet not limiting manner the pathogens listed in Table 3 as well as the diseases associated therewith are to be mentioned as bacterial pathogens.

TABLE 3

Viral diseases

| Disease | Pathogen |
| --- | --- |
| American wheat striate (wheat striate mosaic) | American wheat striate mosaic virus (AWSMV) |
| Barley stripe mosaic | Barley stripe mosaic virus (BSMV) |
| Barley yellow dwarf | Barley yellow dwarf virus (BYDV) |
| Brome mosaic | Brome mosaic virus (BMV) |
| Cereal chlorotic mottle | Cereal chlorotic mottle virus (CCMV) |
| Corn chlorotic vein banding (Braizilian maize mosaic) | Corn chlorotic vein banding virus (CCVBV) |
| Corn lethal necrosis | Virus complex from Maize chlorotic mottle virus (MCMV) and Maize dwarf mosaic virus (MDMV) A or B or Wheat streak mosaic virus(WSMV) |
| Cucumber mosaic | Cucumber mosaic virus (CMV) |
| Cynodon chlorotic streak | Cynodon chlorotic streak virus (CCSV) |
| Johnsongrass mosaic | Johnsongrass mosaic virus (JGMV) |
| Maize bushy stunt | Mycoplasma-like organism (MLO) associated |
| Maize chlorotic dwarf | Maize chlorotic dwarf virus (MCDV) |
| Maize chlorotic mottle | Maize chlorotic mottle virus (MCMV) |
| Maize dwarf mosaic | Maize dwarf mosaic virus (MDMV) strains A, D, E and F |
| Maize leaf fleck | Maize leaf fleck virus (MLFV) |
| Maize line | Maize line virus (MLV) |
| Maize mosaic (corn leaf stripe, enanismo rayado) | Maize mosaic virus (MMV) |
| Maize mottle and chlorotic stunt | Maize mottle and chlorotic stunt virus |
| Maize pellucid ringspot | Maize pellucid ringspot virus (MPRV) |
| Maize raya gruesa | Maize raya gruesa virus (MRGV) |
| maize rayado fino (fine striping disease) | Maize rayado fino virus (MRFV) |
| Maize red leaf and red stripe | Mollicute |
| Maize red stripe | Maize red stripe virus (MRSV) |
| Maize ring mottle | Maize ring mottle virus (MRMV) |
| Maize rio IV | Maize rio cuarto virus (MRCV) |
| Maize rough dwarf (nanismo ruvido) | Maize rough dwarf virus (MRDV) (Cereal tillering disease virus) |

TABLE 3-continued

Viral diseases

| Disease | Pathogen |
| --- | --- |
| Maize sterile stunt | Maize sterile stunt virus (strains of barley yellow striate virus) |
| Maize streak | Maize streak virus (MSV) |
| Maize stripe (maize chlorotic stripe, maize hoja blanca) | Maize stripe virus |
| Maize stunting | Maize stunting virus |
| Maize tassel abortion | Maize tassel abortion virus (MTAV) |
| Maize vein enation | Maize vein enation virus (MVEV) |
| Maize wallaby ear | Maize wallaby ear virus (MWEV) |
| Maize white leaf | Maize white leaf virus |
| Maize white line mosaic | Maize white line mosaic virus (MWLMV) |
| Millet red leaf | Millet red leaf virus (MRLV) |
| Northern cereal mosaic | Northern cereal mosaic virus (NCMV) |
| Oat pseudorosette (zakuklivanie) | Oat pseudorosette virus |
| Oat sterile dwarf | Oat sterile dwarf virus (OSDV) |
| Rice black-streaked dwarf | Rice black-streaked dwarf virus (RBSDV) |
| Rice stripe | Rice stripe virus (RSV) |
| Sorghum mosaic | Sorghum mosaic virus (SrMV) (also: sugarcane mosaic virus (SCMV) strains H, I and M) |
| Sugarcane Fiji disease | Sugarcane Fiji disease virus (FDV) |
| Sugarcane mosaic | Sugarcane mosaic virus (SCMV) strains A, B, D, E, SC, BC, Sabi and MB (formerly MDMV-B) |
| Wheat spot mosaic | Wheat spot mosaic virus (WSMV) |

The transgenic plants produced according to the present invention can also be resistant to animal pests like insects and nematodes. Insects, like for example beetles, caterpillars, lice, or mites are to be mentioned in an exemplary, yet not limiting manner.

Preferably, the plants produced according to the present invention are resistant to insects of the species of *Coleoptera, Diptera, Hymenoptera, Lepidoptera, Mallophaga, Homoptera, Hemiptera, Orthoptera, Thysanoptera. Dermaptera, Isoptera, Anoplura, Siphonaptera, Trichoptera*, etc. Insects of the following species are particularly preferred: *Coleoptera* and *Lepidoptera*, like, for example, the European Corn Borer (ECB), *Diabrotica barberi* (northern corn rootworm), *Diabrotica undecimpunctata* (southern corn rootworm), *Diabrotica virgifera* (western corn rootworm), *Agrotis ipsilon* (black cutworm), *Crymodes devastator* (glassy cutworm), *Feltia ducens* (dingy cutworm), *Agrotis gladiaria* (claybacked cutworm), *Melanotus* spp., *Aeolus mellillus* (wireworm), *Aeolus mancus* (wheat wireworm), *Horistonotus uhlerii* (sand wireworm), *Sphenophorus maidis* (maize billbug), *Sphenophorus zeae* (timothy billbug), *Sphenophorus parvulus* (bluegrass billbug), *Sphenophorus callosus* (southern corn billbug), *Phyllogphaga* spp. (white grubs), *Anuraphis maidiradicis* (corn root aphid), *Delia platura* (seedcorn maggot), *Colaspis brunnea* (grape colaspis), *Stenolophus lecontei* (seedcorn beetle) and *Clivinia impressifrons* (lender seedcorn beetle).

Furthermore, there are to be mentioned: the cereal leaf beetle (*Oulema melanopus*), the frit fly (*Oscinella frit*), wireworms (*Agrotis lineatus*), and aphids (like for example the bird cherry-oat aphid *Rhopalosiphum padi*, the grain aphid *Sitobion avenae*).

The pathogens listed in table 4 as well as the diseases associated therewith are to be mentioned as nematode pests in an exemplary, yet not limiting manner.

TABLE 4

Parasitic nematodes

| Damage | Pathogenic nematodes |
| --- | --- |
| Awl | *Dolichodorus* spp., *D. heterocephalus* |
| Bulb and stem nematode, beet eelworm ("Bulb and stem"; Europe) | *Ditylenchus dipsaci* |
| Burrowing | *Radopholus similis* |
| Cereal cyst nematode ("Cyst") | *Heterodera avenae, H. zeae, Punctodera chalcoensis* |
| Dagger | *Xiphinema* spp., *X. americanum, X. mediterraneum* |
| False root-knot | *Nacobbus dorsalis* |
| Lance, Columbia | *Hoplolaimus columbus* |
| Lance | *Hoplolaimus* spp., *H. galeatus* |
| Lesion | *Pratylenchus* spp., *P. brachyurus, P. crenatus, P. hexincisus, P. neglectus, P. penetrans, P. scribneri, P. thornei, P. zeae* |
| Needle | *Longidorus* spp., *L. breviannulatus* |
| Ring | *Criconemella* spp., *C. ornata* |
| Root-knot nematode ("Root-knot") | *Meloidogyne* spp., *M. chitwoodi, M. incognita, M. javanica* |

TABLE 4-continued

Parasitic nematodes

| Damage | Pathogenic nematodes |
| --- | --- |
| Spiral | *Helicotylenchus* spp. |
| Sting | *Belonolaimus* spp., *B. longicaudatus* |
| Stubby-root | *Paratrichodorus* spp., *P. christiei, P. minor, Quinisulcius acutus, Trichodorus* spp. |
| Stunt | *Tylenchorhynchus dubius* |

Traditionally, the above-mentioned as well as further fungal plant diseases are antagonized by the use of fungicides having the known disadvantages like dispersion in groundwater and accumulation in the food chain.

However, during the last few years various genes have been identified that are capable of mediating resistance to a specific or to several pathogens. The term "mediating pathogen resistance", as used herein, is understood to denote that plants in which the expression of said genes is increased are less susceptible to infection with specific pathogens as compared to plants in which the expression of said genes is normal. Among the genes mediating pathogen resistance are also those genes whose expression is switched on by infection with a pathogen.

Among said resistance genes are peroxidases and oxalate oxidases. The oxalate oxidases, which belong to the family of germinoid proteins, catalyze the oxidation of oxalate, thereby producing hydrogen peroxide. Hydrogen peroxide acts microbicidally and is capable of enhancing lignification of the cell walls, thereby preventing the intrusion of pests. At low concentrations, it is furthermore capable of inducing hypersensitive cell death. The peroxidases use either molecular oxygen or hydrogen peroxide to oxidize and thereby detoxify cellular substrates. A peroxidase suitable for over-expression in wheat and barley is TaPERO (Accession Number X56011; Altpeter et al. (2005) Plant Molecular Biology 57: 271-283; DE 103 46 611 A1).

Pathogens which the expression of the oxalate oxidases and peroxidases in the epidermis of plants is capable of mediating resistance to, include, for example: downy mildew, *Fusarium* spp., *Rynchosporium secalis* and *Pyrenophora teres*.

Further genes capable of mediating resistance to pathogens are chitinases, Ag-AFP, GSTA1 and WIR1a.

By means of pathogen-inducible expression of the nucleotide sequence coding for said enzymes in the epidermis of transgenic plants with the aid of the promoter region according to the present invention, it is possible to obtain plants having an increased pathogen resistance.

In contrast to the genes mediating pathogen resistance, there are also plant innate genes, which enhance the intrusion of a pathogen. Among those is the Mlo gene (Accession Number AF361933), which codes for a seven-transmembrane receptor, which seems to enhance the intrusion of the mildew fungus into the epidermis. In this case it is useful to interfere with the expression of the Mlo gene in order to prevent the intrusion of fungi into the plant. This can, for example, be performed with the aid of the above-described RNAi method. The suitability of interfering with the expression of the Mlo gene for preventing the intrusion of the mildew fungus into the plant has been shown in vitro with leaf segments from barley, which were bombarded with tungsten particles that had been coated with Mlo dsRNA (Schweizer et al. (2000) The Plant Journal 24 (6): 895-903).

Further plant genes which are capable of mediating the interaction of a pathogen with the plant and thereby enhancing the intrusion of the pathogen into the plant are, for example, amino acid or sugar transporters or invertases. Said genes are also suitable as starting points for gene silencing.

The present invention thus relates to a method for producing pathogen-resistant plants, comprising the steps:
 a) generating a recombinant nucleic acid molecule, in which the promoter according to the present invention is present in operative linkage with a nucleic acid sequence mediating pathogen resistance,
 b) transferring the recombinant nucleic acid molecule from a) to plant cells and
 c) regenerating entirely transformed plants and, if desired, propagating the plants.

Preferably, the nucleic acid sequence mediating pathogen resistance is the coding region of a peroxidase or oxalate oxidase gene or a sequence interfering with the endogenous Mlo RNA.

The promoter sequence according to the present invention can also be used for assaying pathogen-induced signal transduction pathways in plants. To this end, a recombinant nucleic acid molecule comprising a reporter gene, which is under the control of the promoter region according to the present invention, together with a further recombinant nucleic acid molecule, which inhibits the expression of an endogenous gene or expresses a mutant of the endogenous gene, can be introduced into plant cells and the transformed plant cells can be inoculated with a suitable pathogen. After a suitable incubation period, the expression of the reporter gene in the plant cells can be determined and compared to the expression of the reporter gene in a plant cell, which, as a control, was transformed only with the reporter construct. If the expression of the reporter gene is inhibited as compared to the control, the inhibited endogenous gene is a positive regulator of the pathogen-induced signal pathway. In contrast, the inhibited gene is a negative regulator of the signal transduction pathway, if the expression of the reporter gene is increased as compared to the control.

Suitable methods for inhibiting the expression of the endogenous gene include antisense methods, RNAi or TILLING. The TILLING method is a strategy of so-called reverse genetics, which combines the production of high densities of point mutations in mutagenized plant collections, for example by means of chemical mutagenesis with ethylmethanesulfonate (EMS), with fast systematic identification of mutations in target sequences. First, the target sequence is amplified via PCR in DNA pools of mutagenized M2 populations. Denaturing and annealing reactions of the heteroallelic PCR products allow the formation of heteroduplexes, wherein one DNA strand originates from the mutated and the other strand from the wild type PCR product. At the site of the point mutation, a so-called mismatch occurs, which can be identified either via denaturing HPLC (DHPLC, McCallum et al., 2000, Plant Physiol., 123: 439-442) or via the CelI mismatch detection system (Oleykowsky et al, 1998, Nucl. Acids Res. 26: 4597-4602). CelI is an endonuclease recognizing mismatches in heteroduplex DNA and cleaving the DNA specifically at these sites. The fission products can then be separated and detected via automated sequencing gel electrophoresis (Colbert et al., 2001, vide supra). Subsequently to identifying target gene-specific mutations in a pool, individual DNA samples are correspondingly analyzed in order to isolate the plant bearing the mutation.

Suitable proteins, whose function in pathogen induction can be assayed with the aid of the promoter region according to the present invention, are, for example, MAP kinases or phosphatases.

Of course it is also possible to assay pathogen-induced signal transduction with the aid of chemical substances, whose target proteins are known. To this end, plant cells can be transfected with a recombinant nucleic acid molecule comprising the promoter region according to the present invention and inoculated with a suitable pathogen. The chemical substance whose effect on signal transduction is supposed to be assayed can be added to the plants either before, during, or after the inoculation. For evaluation, the activity of the reporter gene in cells that had been treated with the chemical substance can be compared to the activity of the reporter gene in untreated cells.

The following examples serve for illustrating the present invention and are not supposed to be understood as limiting.

FIGURES

1. Vector map of pGLP4GUS

2. Vector map of pGLP4IntronGUS

3. Vector map of pGUS

4. Vector map of pIntronGUS

5. Schematic representation of the reporter constructs used for transient transformation The reporter constructs consist of fusions of the given promoter sequences (black arrow) with the β-glucuronidase reporter (GUS) and the transcriptional terminator of the GSTA1 and 35S gene (GSTA1 and 35S), respectively. For modulating the promoter activity, a cassette consisting of the exon1 intron1 from the WIR1 gene from wheat (I) is inserted. The reporter constructs are depicted schematically together with the standardizing construct (p35SGFP), which allows the expression of the green fluorescent protein from Aequorea victoria under the control of the CaMV 35S promoter.

6. Vector map of p6UGLP4GUS

7. Vector map of p6UGLP4IntronGUS

8. Pathogen-inducible GUS expression in the leaves of transgenic barley plants

EXAMPLES

1. Subcloning

For identifying HvGLP4 genes including the promoter, the BAC clone 418E01 (Druka et al. PNAS 99(2): 850-55) was taken from a barley BAC library (Yu et. al. (2000) TAG 101: 1093-99) and the corresponding gene region was subcloned for sequencing and annotation.

For gene and promoter identification, individual clones were subcloned in two steps. First, the BAC DNA of an individual clone was isolated by means of a Qiagen column (Maxi-Kit; Qiagen; isolation according to the manufacturer's protocol). By means of shearing (Hydroshear: Genomic Solutions), 5-10 kbp fragments of said BAC DNA were generated and the emerging ends were filled up with Klenow to form smooth ends (reaction according to the manufacturer's protocol). Selecting the fragment lengths was performed via an 0.8% agarose gel in 0.5% TBE. The corresponding fragment length region was cut out of the gel and the DNA was eluted from the agarose gel with the aid of the Qiagen Extraction Kit (elution according to the manufacturer's protocol). The 5-10 kbp fragments eluted were ligated into a pBluescript II SK(–) vector linearized with EcoRV having smooth dephosphorylated ends (restriction and dephosphorylation according to the manufacturer's instructions) and chemically-thermically transformed into highly competent E. coli cells. Subsequently, the transformants were arbitrarily arranged with the aid of a picking robot (Qpick, Genetix) and transferred into microtiter plates containing LB medium.

The subfragment bearing the gene of interest and maximizing the length of the potential promoter was selected by means of PCR (see under 2.). The subfragment selected was again sheared into 1-2 kbp fragments, ligated, transformed and the clones were stored in microtiter plates (see above). From the picked clones, 96 colonies were arbitrarily selected and sequenced with the TempliPhi protocol (Amersham Biosciences), according to the manufacturer's instructions. The sequences were assembled. The sequence information obtained was used for annotating the coding exons as compared to cDNA sequences of HvGLP4 in order to determine the HvGLP4 genes located on the BAC subclone as well as their potential promoters.

2. PCR Amplification of the Sequences of Interest from the BAC Clone

Due to its high sensitivity, PCR was chosen for detecting the wanted DNA sequence. Analysis was conducted in 20 µl reaction volume. The reaction setup consisted of 10 mM Tris HCl, pH 9.0; 50 mM KCl; 0.1% Triton X-100, 0.2 mM dNTP; 2 mM $MgCl_2$, 0.6 µM oligonucleotide and Taq polymerase each (concentration in the reaction setup: ~1 U $µl^{-1}$). Either 10 ng BAC pool DNA or 2 µl bacteria culture (for colony PCR) were used per reaction setup. Available HvGLP4 cDNA sequences served as a basis for deriving the oligonucleotides 5'-GGA TTT GTC ACG TCC AAC CT-3' (SEQ ID NO: 14) and 5'-ATT GGC AAT TGT GAT AGC CC-3' (SEQ ID NO: 15).

The BAC DNA to be amplified as well as the primers were provided and subsequently mixed with the PCR reaction setup. For mortifying and lysing the bacteria in a colony PCR, the sample was heated to 95° C. for 5 min before adding the PCR reaction mixture. For denaturing the double-stranded DNA, an initial step of 5 min at 95° C. was used. The touchdown PCR reaction was performed in the steps 30 s 95° C., 30 s 60 to 55° C., and 60 s 72° C. for the first 10 cycles. Herein, the temperature was lowered by 0.5° C. (60 to 55° C.) with each cycle. Further 30 cycles were performed in the steps 30 s 95° C.; 30 s 55° C. and 60 s 72° C. For terminal chain elongation, incubation for 5 min at 72° C. was conducted before the reaction mixture was cooled down to a temperature of 20° C., which was then held constant. Due to the short reaction product of 189 bp that was expected, analysis of the PCR amplificates was performed with 2.5% agarose gels in 0.5×TBE buffer.

3. Generation of the Constructs Used a) Intermediate Vector pSKGLP4 (Cloning the Promoter According to the Present Invention in pBluescript II SK (+))

The promoter sequence according to the present invention (3334 bp) was amplified using the primers 5'-CGTGCG-TAAATTAAGGGCAT-3' (forward) (SEQ ID NO: 8) and 5'-CAGCTCCTTTGGGTCTTG-3' (reverse) (SEQ ID NO: 9) from the genomic GLP4 clone (418e1-c9) by means of PCR. The 5' end of the reverse primer was positioned 5 by upstream of the GLP4 starting codon. The GLP4 promoter fragment was purified via agarose gel electrophoresis and phosphorylated by means of T4 polynucleotide kinase. The vector pBluescript II SK (+) was cut with EcoRV at the multiple cloning site and was ligated with the blunt ends of the GLP4 promoter fragment. In this undirected ligation, products bearing the GLP4 promoter fragment in both orientations are obtained. The resulting plasmid (pSKGLP4), which bore the forward primer sequence adjacent to the HindIII interface of the pBluescript II SK (+) vector, was used for constructing the reporter vectors pGLP4GUS and pGLP4IntronGUS due to the position of restriction interfaces (KpnI, PstI and SmaI).

b) Reporter Vector pGLP4GUS (GUS Expression Under the Control of the Promoter According to the Present Invention)

The GLP4 promoter sequence according to the present invention was cut out of the intermediate vector pSKGLP4 by means of KpnI and SmaI restriction cleavage. The fragment having a length of 3396 bp was ligated into the pPS18 vector (DE 103 46 611 A1), which was cut with KpnI/SmaI and purified via agarose gel electrophoresis. By means of substituting the WIR1a gene fragment containing the GstAI promoter and intron with the GLP4 promoter sequence, a transcriptional fusion was obtained, in which the expression of the GUS reporter gene is controlled by the GLP4 promoter. The sequence of the resulting plasmid is given in SEQ ID NO: 4 and the structure of the plasmid is depicted in FIG. 1.

c) Reporter Vector pGLP4IntronGUS (GUS Expression Under the Control of the Promoter According to the Present Invention and Modulated by an Intron-Containing WIR1a Gene Fragment)

Figure 2:
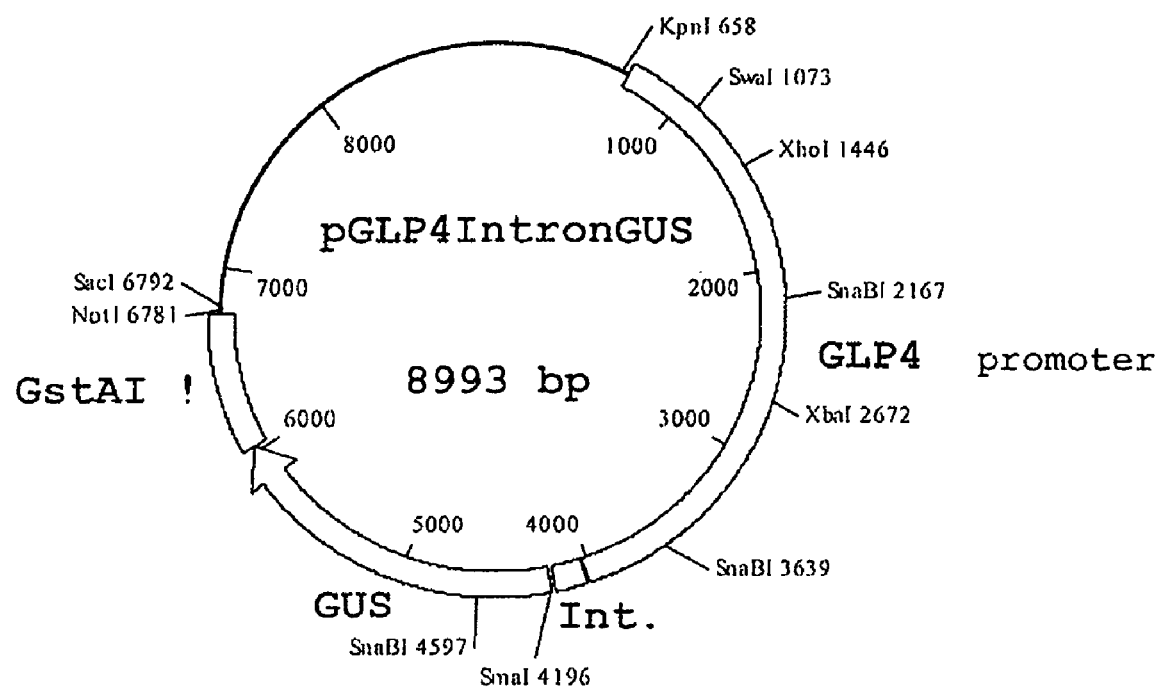
FIG. 2 depicts the vector map of pGLP4IntronGUS.

The GLP4 promoter sequence according to the present invention was cut out of the intermediate vector pSKGLP4 by means of KpnI and PstI restriction cleavage. The fragment having a length of 3392 bp was ligated into the pPS18 vector, which was cut with KpnI/PstI and purified via agarose gel electrophoresis. By means of substituting the GstAI promoter sequence with the GLP4 promoter sequence, a transcriptional fusion of the intron-containing WIR1a gene fragment with the GUS reporter gene was obtained, which is controlled by the GLP4 promoter. The sequence of the resulting plasmid is given in SEQ ID NO: 5 and the structure of the plasmid is depicted in FIG. 2.

d) Reporter Vector pGUS (GUS Reporter Gene Without Promoter, Control Plasmid)

Figure 3:
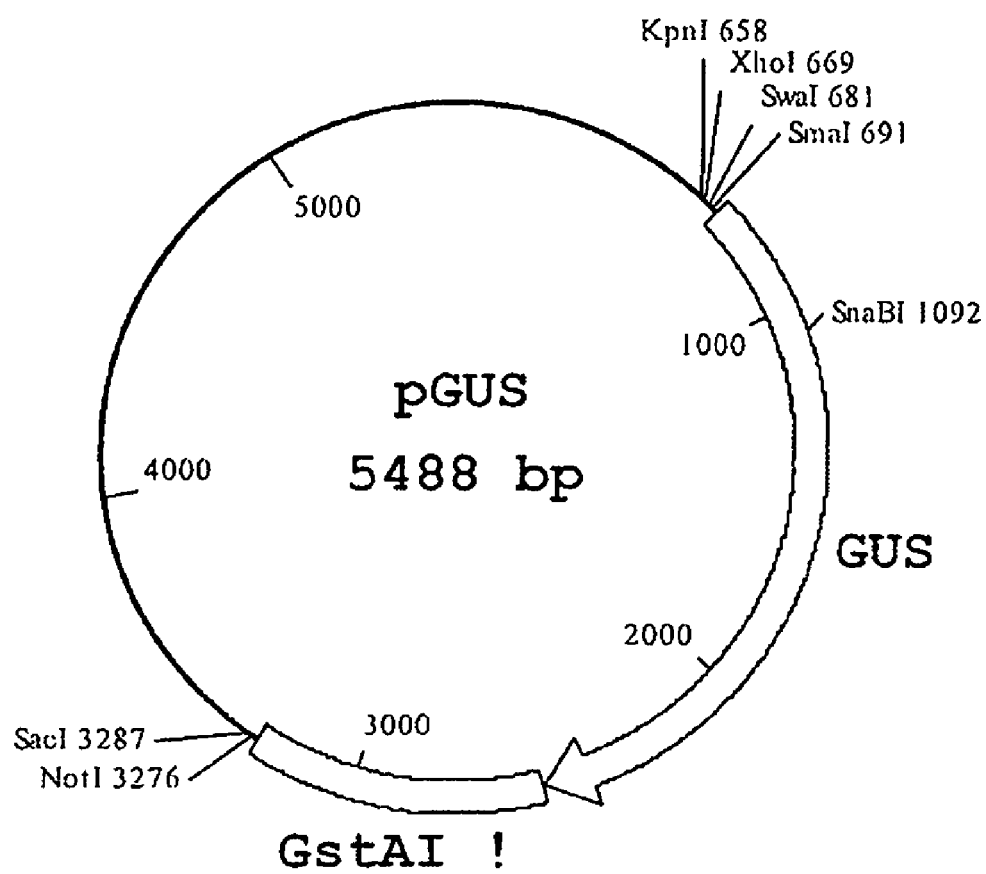
FIG. 3 depicts the vector map of pGUS.

The pPS18 vector, which was opened with XhoI/XmaI, was purified via agarose gel electrophoresis and was ligated with a double-stranded oligonucleotide (5'-TCGAGCA-CATTTAAATCAAC-3' (SEQ ID NO: 10) plus 5'-CCGGGT-TGATTTAAATGTGC-3' (SEQ ID NO: 11)). In the control plasmid (pGUS), the GUS reporter gene is present without promoter. The sequence of the resulting plasmid is given in SEQ ID NO: 6 and the structure of the plasmid is depicted in FIG. 3.

e) Reporter Vector pIntronGUS (GUS Reporter Gene Without Promoter with Intron-Containing WIR1a Gene Fragment, Control Plasmid)

Figure 4:
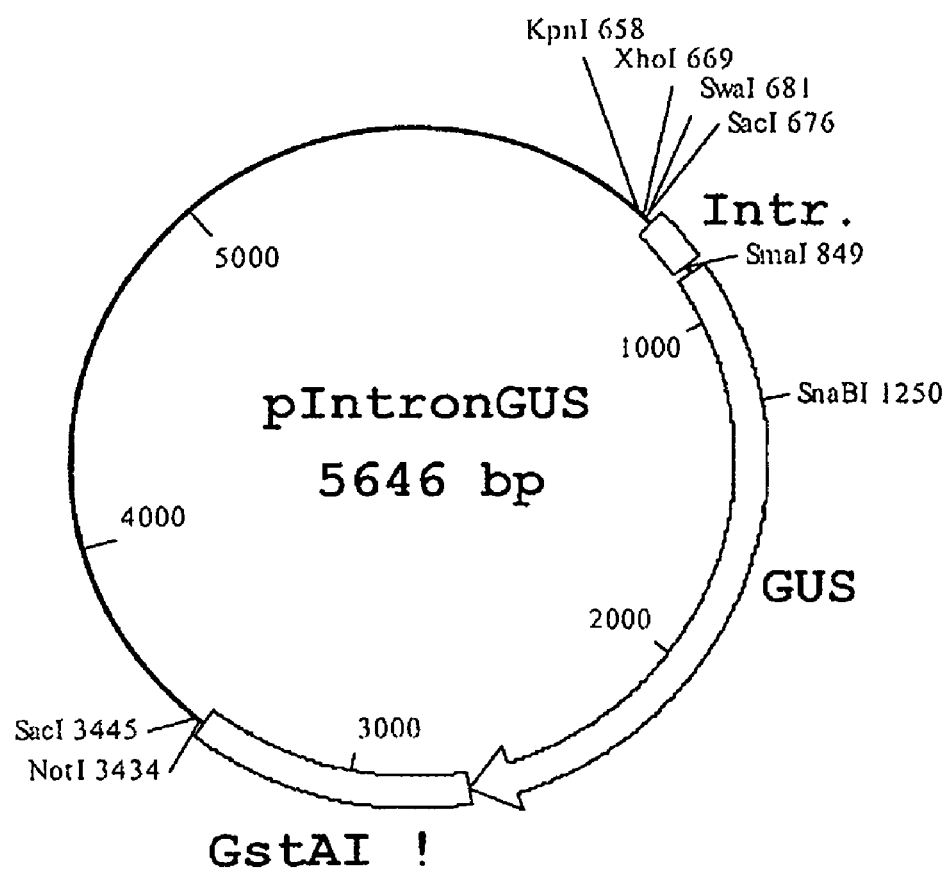
FIG. 4 depicts the vector map of pintronGUS.

The pPS18 vector, which was opened with XhoI/PstI, was purified via agarose gel electrophoresis and was ligated with a double-stranded oligonucleotide (5'-TCGAGCTCATT-TAAATCCTCTGCA-3' SEQ ID NO: 12)plus 5'-GAGGATT-TAAATGAGC-3' (SEQ ID NO: 13)). In the resulting control plasmid (pIntronGUS), the intron-containing WIR1a gene sequence without GstAI promoter is fused with the GUS reporter gene. The sequence of the resulting plasmid is given in SEQ ID NO: 7 and the structure of the plasmid is depicted in FIG. 4.

Figure 5:
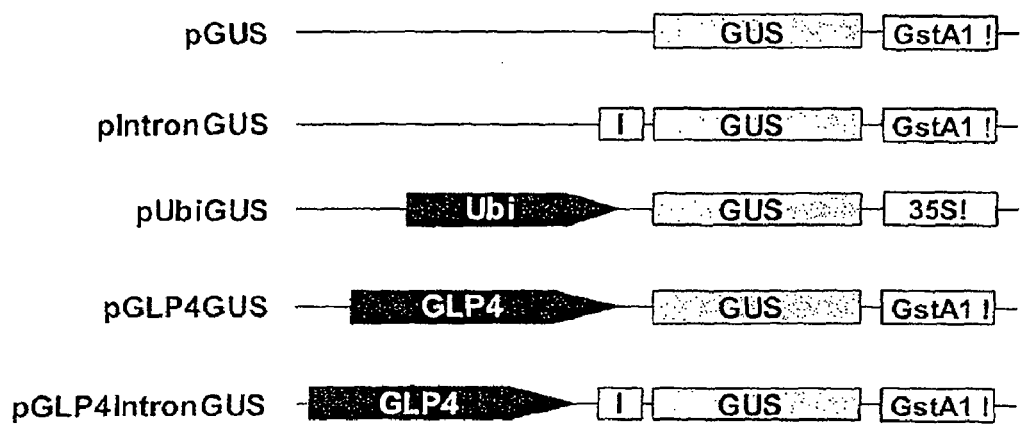
FIG. 5 provides a schematic representation of the reporter constructs used for transient transformation.
Figure 5:

4. Transient Expression of the Reporter Vectors in Barley Leaves by Means of Particle Bombardment The reporter constructs used for transformation are schematically depicted in FIG. 5. They were introduced into barley leaves by means of a "gene gun" (Bio-Rad, Model PDS-1000/He, Hepta-Adapter) via biolistic transformation according to Douchkov et al. (2005) Mol. Plant Microbe Interact. 18: 755-761. For the coating with DNA, 2.18 mg gold particles (1.0 µm diameter, particle density 25 mg ml$^{-1}$ in 50% (v/v) glycerin) were mixed with 7 µg supercoiled DNA and spiked with 1 M Ca(NO$_3$)$_2$ pH 10 per shot, so that the final concentration of Ca(NO$_3$)$_2$ was 0.5 M. Subsequent to centrifuging and washing with 70% (v/v) ethanol, the particles were resuspended in 96% (v/v) ethanol and arranged on the 7 macro carriers. In a vacuum (3.6×10$^3$ Pa), by means of a helium pressure wave of 7.6×10$^6$ Pa, the particles were introduced into 7 leaf segments of 7 days old wild type barley plants (Golden Promise) in each case. For bombardment, the leaf segments were laid into a petri dish on 0.5% (w/v) phyto agar, which was spiked 20 µg ml$^{-1}$ benzimidazole. Subsequent to bombardment, the leaves were incubated for 4 h at −20° C. in indirect daylight.

5. Inoculation of the Leaf Segments with Mildew Spores

The bombarded leaves were transferred to polycarbonate dishes with 1% (w/v) phyto agar containing 20 µg ml$^-$benzimidazole. Infection with mildew spores was performed in an inoculation tower by means of shaking spores of highly infected wheat leaves into the tower. After 5 min, the dishes were removed from the tower, sealed and incubated at +20° C. in indirect daylight for 60 h.

6. Detection of Green Fluorescent Protein (GFP)

The number of GFP-expressing epidermal cells of bombarded leaves was determined 24 h subsequent to transformation by means of incident light fluorescence microscopy. To this end, a Zeiss Axioplan Imaging 2 microscope with a set of filters No. 10 and 100-fold magnification was used: excitation window 450-490 nm; emission window bypass 515-565 nm. Expression of the constitutively expressed GFP served for standardizing the expression.

7. Histochemical Detection of the GUS Expression

The leaves were infiltrated under vacuum with the GUS detection solution (10 mM EDTA, 1.4 mM K$_3$[Fe(CN)$_6$], 1.4 mM K$_4$[Fe(CN)$_6$], 0.1% (v/v) Triton X-100, 20% (v/v) methanol, 1 mg/ml 3-bromo-4-chloro-3-indolyl-β-D-glucuronic acid, 100 mM Na phosphate buffer, pH 7.0) and incubated overnight at +37° C. Subsequent to removing the detection solution, the leaves were discolored with a solution of 7.5% (w/v) trichloroacetic acid and 50% (v/v) methanol for 15 min at +20° C. The light microscopic detection of the GUS expression was performed with a Zeiss Axiolab microscope at 100-fold magnification. The content of cells exhibiting GUS expression is colored blue.

A quantitative comparison of the GUS expression in the leaves transformed with the different reporter constructs, which had either been infected or not infected with mildew, is depicted in the following Table 5, which shows the results from two independent experiments with 14 leaves.

TABLE 5

| GUS-positive epidermal cells | | |
|---|---|---|
| Construct | Control | Inoculated |
| pGUS | 0 | 0 |
| pIntronGUS | 0 | 0 |
| pUbiGUS | 197 | 804 |
| pGLP4GUS | 0 | 35 |
| pGLP4IntronGUS | 0 | 79 |

It shows that the promoter according to the present invention, in contrast to the ubiquitin promoter, is only active in epidermal cells that have been inoculated with mildew, but not in uninoculated control cells. By means of fusing the promoter region according to the present invention with the intron of the WIR1a gene, it is possible to increase the expression of the reporter gene by more than double.

8. Generating Binary Vectors for Transforming Plants a) p6UGLP4GUS (GUS Expression Under the Control of the Promoter According to the Present Invention)

The expression cassette from the vector pGLP4GUS, which is controlled by the promoter according to the present invention, was cloned into the binary vector (p6U available from "DNA-Cloning-Service", Hamburg, Germany) by means of SfiI restriction interfaces. As the cassette from pGLP4GUS has no SfiI restriction interfaces, it was initially cloned between the two SfiI restriction interfaces of the intermediate vector pNOS-AB-M ("DNA-Cloning-Service", Hamburg, Germany).

For generating the intermediate vector pNOS-AB-M GLP4GUS, the expression cassette having a length of 5945 bp and consisting of the promoter sequence according to the present invention, the GUS reporter sequence and the GstA1 transcription terminator was cut out of the reporter vector pGLP4GUS by means of HindIII/NotI restriction cleavage and was purified via agarose gel electrophoresis. The cassette was ligated into the intermediate vector pNOS-AB-M (by "DNA-Cloning-Service", Hamburg, Germany), which had been cut with HindIII/NotI and purified via agarose gel electrophoresis. The resulting plasmid pNOS-AB-M GLP4GUS bore the expression cassette flanked by two SfiI interfaces and was employed for constructing the binary vector p6UGLP4GUS.

Figure 6:
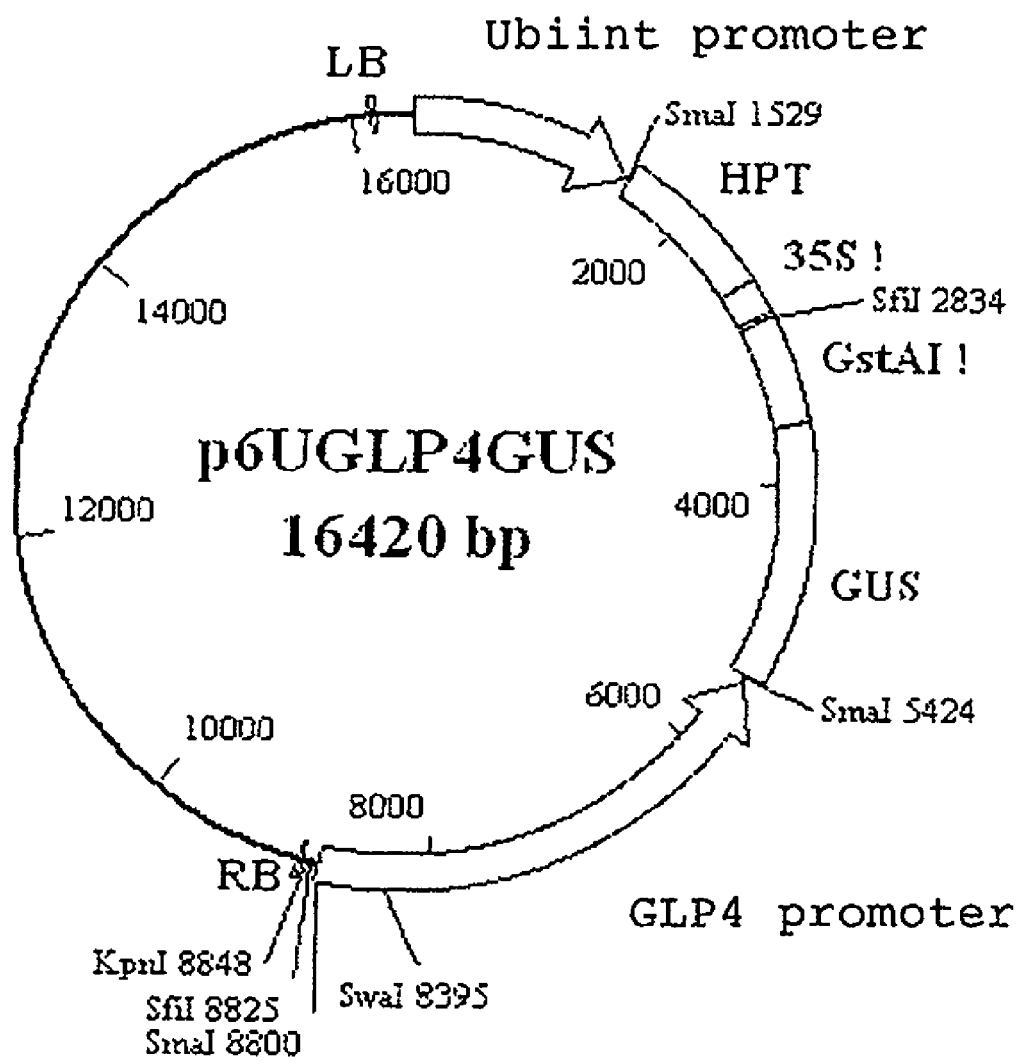
FIG. 6 depicts the vector map of p6UGLP4GUS.

The expression cassette having a length of 5991 bp and consisting of the promoter sequence according to the present invention, the GUS reporter sequence and the GstA1 transcription terminator was cut out of the intermediate vector pNOS-AB-M GLP4GUS with SfiI and was ligated with the SfiI interfaces of the binary vector p6U in a directed manner. The sequence of the resulting plasmid p6UGLP4GUS is given in SEQ ID NO: 18 and the structure of the plasmid is depicted in FIG. 6.

b) p6UGLP4IntronGUS (GUS Expression Under the Control of the Promoter According to the Present Invention and Modulated by an Intron-Containing WIR1a Gene Fragment)

The expression cassette from pGLP4IntronGUS (promoter sequence according to the present invention, intron-containing WIR1a gene fragment, GUS reporter sequence and GstA1 transcription terminator) was initially cloned into the intermediate vector pNOS-AB-M (by "DNA-Cloning-Service", Hamburg, Germany) in order to flank the expression cassette with additional SfiI restriction interfaces. The cassette was then ligated into the SfiI interface as SfiI fragment of the binary vector p6U (by "DNA-Cloning-Service", Hamburg, Germany).

For generating the intermediate vector pNOS-AB-M GLP4IntronGUS, the expression cassette having a length of 6097 bp (promoter sequence according to the present invention, intron-containing WIR1a gene fragment, GUS reporter sequence and GstA1 transcription terminator) was cut out of pGLP4IntronGUS by means of HindIII/NotI restriction cleavage and was purified via agarose gel electrophoresis. The cassette was ligated into the intermediate vector pNOS-AB-M (by "DNA-Cloning-Service", Hamburg, Germany), which was cut with HindIII/NotI and purified via agarose gel electrophoresis. The resulting plasmid pNOS-AB-M GLP4IntronGUS bore the expression cassette flanked by two SfiI interfaces and was employed for constructing the binary vector p6UGLP4IntronGUS.

Figure 7:
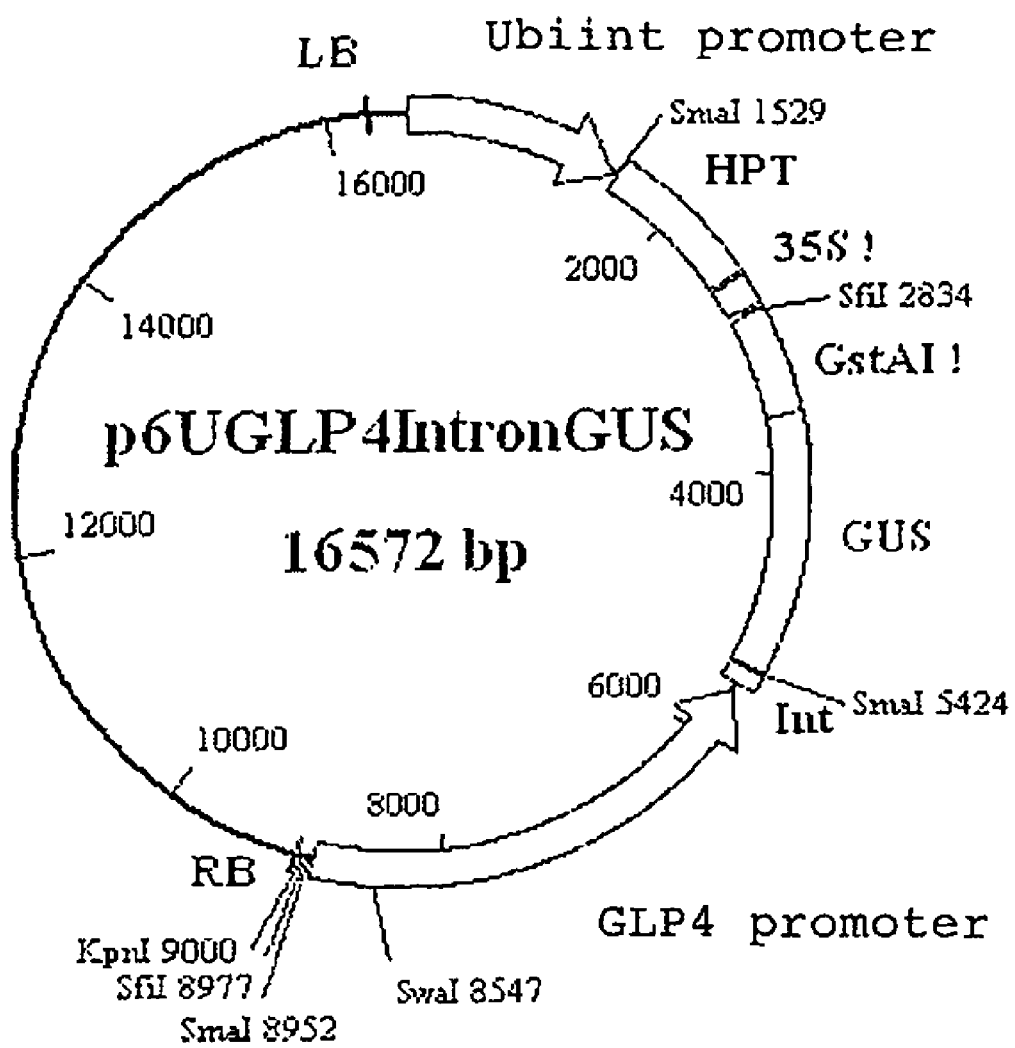
FIG. 7 depicts the vector map of p6UGLP4IntronGUS.

The expression cassette having a length of 6143 bp (promoter sequence according to the present invention, intron-containing WIR1a gene fragment, GUS reporter sequence and GstA1 transcription terminator) was cut out of the intermediate vector pNOS-AB-M GLP4IntronGUS with SfiI and was ligated with the SfiI interfaces of the binary vector p6U in a directed manner. The sequence of the resulting plasmid p6UGLP4IntronGUS is given in SEQ ID NO: 19 and the structure of the plasmid is depicted in FIG. 7.

9. Agrobacterium-Mediated Transformation of Barley Plants

Immature embryos were collected in 2.5 ml CIM (Tingay et al. (1997) Plant J. 11: 1369-1376) containing 800 mg/l cysteine and 500 µM acetosyringone. The medium was removed and 600 µl agrobacterium, which had been transformed with the respective plasmid, were added. Subsequently, a vacuum filtration for one minute at 500 mbar was performed before the embryos were left to rest for 10 minutes. After that, they were washed twice with 2.5 ml CIM containing 800 mg/l cysteine and 500 µM acetosyringone before they were cultivated for 2-3 days at 21° C. in the dark in 2.5 ml CIM containing 800 mg/l cysteine and 500 µM acetosyringone. Subsequently, the embryos were transferred to solid CIM (Trifinova et al. (2001) Plant Sci. 162: 871-880) containing 150 mg/l timentin and 50 mg/l hygromycin. Callus induction was conducted for four weeks at 24° C. in the dark. Subsequently, regeneration to K4N (Kumlehn et al. (2006)

Plant Biotechnology Journal 4: 251-261) with 150 mg/l timentin and 25 mg/l hygromycin was conducted. Further details on transforming barley can be taken from the publication by Hensel and Kumlehn, Genetic transformation of barley (Hordeum vulgare L.) by coculture of immature embryos with Agrobacteria. In: Curtis, I. S. (Ed.) Transgenic crops of the world—Essential protocols (2004), Kluwer, Dordrecht, pages 35-44.

10. Inoculating the Leaf Segments of the Transgenic Barley Plants (Golden Promise::GLP4GUS and Golden Promise::GLP4IntronGUS) with Mildew Spores Leaf segments of the transgenic barley plants (Golden Promise::GLP4GUS and Golden Promise::GLP4IntronGUS) were laid out in polycarbonate dishes on phyto agar (1% w/v) with benzimidazole (20 µg/ml). Infection with mildew spores was performed in an inoculation tower by means of shaking off spores from highly infected barley leaves. After 5 min, the dishes were sealed and incubated at +20° C. and in indirect daylight for 60 h.

11. Histochemical Detection of the GUS Expression in Transgenic Barley Plants (Golden Promise::GLP4GUS and Golden Promise::GLP4IntronGUS)

The leaves of the transgenic barley plants (Golden Promise::GLP4GUS and Golden Promise::GLP4IntronGUS) were infiltrated under vacuum with the GUS detection solution (10 mM EDTA, 1.4 mM $K_3[Fe(CN)_6]$, 1.4 mM $K_4[Fe(CN)_6]$, 0.1% (v/v) triton X-100, 20% (v/v) methanol, 1 mg/ml 3-bromo-4-chloro-3-indoxyl-β-D-glucuronic acid, 100 mM Na phosphate buffer, pH 7.0) and incubated for 24 h at +37° C. After removing the detection solution, the leaves were discolored with 7.5% (w/v) trichloroacetic acid in 50% (v/v) methanol (15 min at +20° C.) and with ethanol solutions (20%, 40%, 60% and 80%) for 30 min at 50° C. in each case. Light microscopy was performed using a Zeiss Axiolab at 100-fold magnification. The content of cells exhibiting GUS expression is colored blue.

Figure 8:
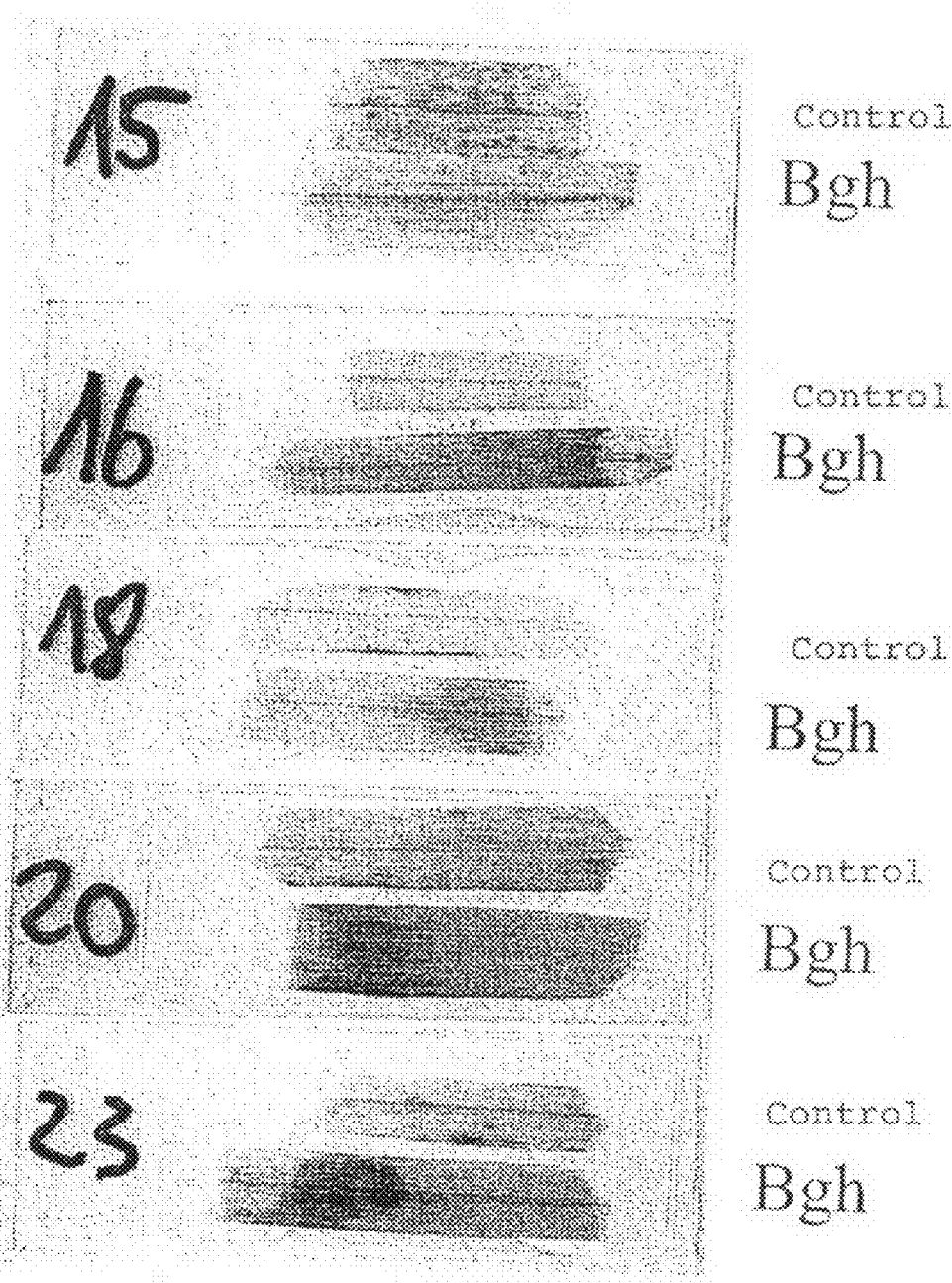
FIG. 8 demonstrates pathogen-inducible GUS expression in the leaves of transgenic barley plants. The numbers refer to the five transgenic lines that were analyzed.

The results of the GUS coloring of leaves from transgenic plants are depicted in FIG. 8. All of the five transgenic lines that were analyzed exhibited GUS expression in the leaf, which varied in intensity and was induced by mildew.

The invention claimed is:

1. An isolated pathogen-inducible promoter region with specificity for the plant epidermis, selected from the group consisting of
   a) a promoter region comprising the nucleic acid sequence given in SEQ ID NO; 1 or 16,
   b) a promoter region comprising a functional part of at least 500 contiguous bases of SEQ ID NO: 1 or 16, and
   c) a promoter region having at least 95% sequence identity to the nucleic acid sequence as set forth in SEQ ID NO: 1 or 16.

2. The promoter region according to claim 1, additionally comprising a sequence comprising the nucleic acid sequence as set forth in SEQ ID NO: 2.

3. The promoter region according to claim 2 comprising a sequence selected from the group consisting of
   a) a promoter region comprising the nucleic acid sequence as set forth in SEQ ID NO: 3 or 17,
   b) a promoter region comprising a functional part of at least 500 contiguous bases of SEQ ID NO: 3 or 17, and
   c) a promoter region having at least 95% sequence identity to the nucleic acid sequence as set forth in SEQ ID NO: 3 or 17.

4. A chimeric gene, comprising the promoter region according to claim 1 in operative linkage with a coding sequence.

5. The chimeric gene according to claim 4, wherein expression of the coding sequence leads to an increased content of a protein in the epidermis.

6. The chimeric gene according to claim 4, wherein the coding sequence originates from a reporter gene.

7. The chimeric gene according to claim 4, wherein the coding sequence originates from a resistance gene.

8. The chimeric gene according to claim 4, wherein expression of the coding sequence inhibits the expression of the corresponding endogenous coding sequence in the epidermis.

9. The chimeric gene according to claim 8, wherein the coding sequence is present in antisense orientation with respect to the promoter.

10. The chimeric gene according to claim 8, wherein the expression of the endogenous coding sequence is inhibited by RNA interference.

11. A recombinant nucleic acid molecule comprising the promoter region according to claim 1 or a chimeric gene comprising the promoter region in operative linkage with a coding sequence.

12. The recombinant nucleic acid molecule according to claim 11, additionally comprising transcriptional termination sequences.

13. A method for generating a transgenic plant with epidermis-specific, pathogen-inducible expression of a trans gene, comprising:
   a) generating the recombinant nucleic acid molecule according to claim 11,
   b) transferring the recombinant nucleic acid molecule to a plant cell; and
   c) regenerating a transformed plant and, optionally, propagating the plant.

14. A transgenic plant, plant cell, plant part or propagation material thereof, which comprises the recombinant nucleic acid molecule according to claim 11, wherein the plant part or propagation material thereof includes protoplasts, calli, seeds, tubers, seedlings, or transgenic offspring of said plant.

15. The transgenic plant according to claim 14, wherein the plant is a monocotyledonous plant.

16. The transgenic plant according to claim 15, wherein the plant is a poaceae.

17. The transgenic plant according to claim 16, wherein the plant is wheat or barley.

18. A method for epidermis-specific expression of a transgene in a plant or plant cell, comprising expressing the transgene under the control of the promoter region of claim 1.

19. The method according to claim 18, wherein the transgene is a resistance gene.

20. A method for increasing pathogen resistance in a transgenic plant, comprising:
   a) generating the recombinant nucleic acid molecule according to claim 11,
   b) transferring the recombinant nucleic acid molecule to a plant cell; and
   c) regenerating a transformed plant and, optionally, propagating said plant.

21. A transgenic plant, plant cell, plant part or propagation material thereof having increased pathogen resistance generated according to the method of claim 20, wherein the plant part or transgenic propagation material include protoplasts, calli, seeds, tubers, seedlings, or transgenic offspring of said plant.

22. The transgenic plant according to claim 21, wherein the plant is a monocotyledonous plant.

23. The transgenic plant according to claim 22, wherein the plant is a poaceae.

24. The transgenic plant according to claim 23, wherein the plant is wheat or barley.

25. The transgenic plant according to claim 21, wherein the plant exhibits an increased resistance to downy mildew.

26. A transgenic plant, plant cell, plant part or propagation material thereof, which comprises the recombinant nucleic acid molecule of claim 11, wherein the transgenic plant, plant cell, plant part or propagation material thereof has increased pathogen resistance.

27. The promoter region of claim 1, wherein the promoter region comprises the nucleic acid sequence of SEQ ID NO: 1 or 16.

28. The promoter region of claim 1, wherein the promoter region comprises a functional part of at least 500 contiguous bases of SEQ ID NO: 1 or 16.

29. The promoter region of claim 1, wherein the promoter region comprises a promoter region having at least 95% sequence identity to the nucleic acid sequence as set forth in SEQ ID NO: 1 or 16.

30. The promoter region of claim 3, wherein the promoter region comprises the nucleic acid sequence of SEQ ID NO: 3 or 17.

31. The promoter region of claim 3, wherein the promoter region comprises a functional part of at least 500 contiguous bases of SEQ ID NO: 3 or 17.

32. The promoter region of claim 3, wherein the promoter region comprises a promoter region having at least 95% sequence identity to the nucleic acid sequence of SEQ ID NO: 3 or 17.

33. A transgenic plant, plant cell, plant part or propagation material thereof, which comprises the promoter region of claim 27.

34. A transgenic plant, plant cell, plant part or propagation material thereof, which comprises the promoter region of claim 28.

35. A transgenic plant, plant cell, plant part or propagation material thereof, which comprises the promoter region of claim 29.

36. A transgenic plant, plant cell, plant part or propagation material thereof, which comprises the promoter region of claim 30.

37. A transgenic plant, plant cell, plant part or propagation material thereof, which comprises the promoter region of claim 31.

38. A transgenic plant, plant cell, plant part or propagation material thereof, which comprises the promoter region of claim 32.

\* \* \* \* \*